United States Patent
Xue et al.

(10) Patent No.: US 7,264,949 B2
(45) Date of Patent: Sep. 4, 2007

(54) GLYCEROL-3-PHOSPHATE O-ACYLTRANSFERASE PROMOTER FOR GENE EXPRESSION IN OLEAGINOUS YEAST

(75) Inventors: Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/225,354

(22) Filed: Sep. 13, 2005

(65) Prior Publication Data

US 2006/0057690 A1    Mar. 16, 2006

Related U.S. Application Data

(60) Provisional application No. 60/610,060, filed on Sep. 15, 2004.

(51) Int. Cl.
*C12P 1/00* (2006.01)
*C12P 21/04* (2006.01)

(52) U.S. Cl. .................. 435/71.2; 435/41; 435/45; 435/71.1

(58) Field of Classification Search ............ None
See application file for complete search history.

(56) References Cited

U.S. PATENT DOCUMENTS 4,937,189 A   6/1990  Davidow et al.
6,265,185 B1  7/2001  Muller et al.
2006/0035351 A1  2/2006  Zhu et al.

FOREIGN PATENT DOCUMENTS

| EP | 0 005 227 B1 | 11/1979 |
| EP | 0 220 864 B1 | 5/1987 |
| WO | WO 2004/101757 A2 | 11/2004 |
| WO | WO 2005/003310 A2 | 1/2005 |
| WO | WO 2005/049805 A2 | 6/2005 |

OTHER PUBLICATIONS

NCBI Accession CR382129, Dujon, B. Genome evolution in yeasts. Nature. Jul. 1, 2004;430(6995):35-44 (see attached search print out titled SCORE Search Result Application 11225354 and Search Result us-11-225-354-17.rge ).*
Dujon, B. Genome evolution in yeasts. Nature. Jul. 1, 2004;430(6995):35-44.*
U.S. Appl. No. 11/183,664, filed Jul. 18, 2005, Picataggio et al.
Colin Ratledge, Microbial Oils and Fats: An Assessment of Their Commercial Potential, Progress in Industrial Microbiology, vol. 16:119-206, 1982.
Madzak, Catherine et al., Heterologous protein expression and secretion in the non-conventional yeast *Yarrowia lipolytica*: a review, Journal of Biotechnology, 2004, 109, 63-81, Elsevier B.V.

* cited by examiner

*Primary Examiner*—Joseph Woitach
*Assistant Examiner*—Maria Leavitt

(57) ABSTRACT

The promoter region associated with the *Yarrowia lipolytica* glycerol-3-phosphate O-acyltransferase (gpat) gene has been found to be particularly effective for the expression of heterologous genes in oleaginous yeast. The promoter regions of the instant invention have been shown to be suitable to drive high-level expression of genes involved in the production of ω-3 and ω-6 fatty acids.

1 Claim, 6 Drawing Sheets

Figure 1:
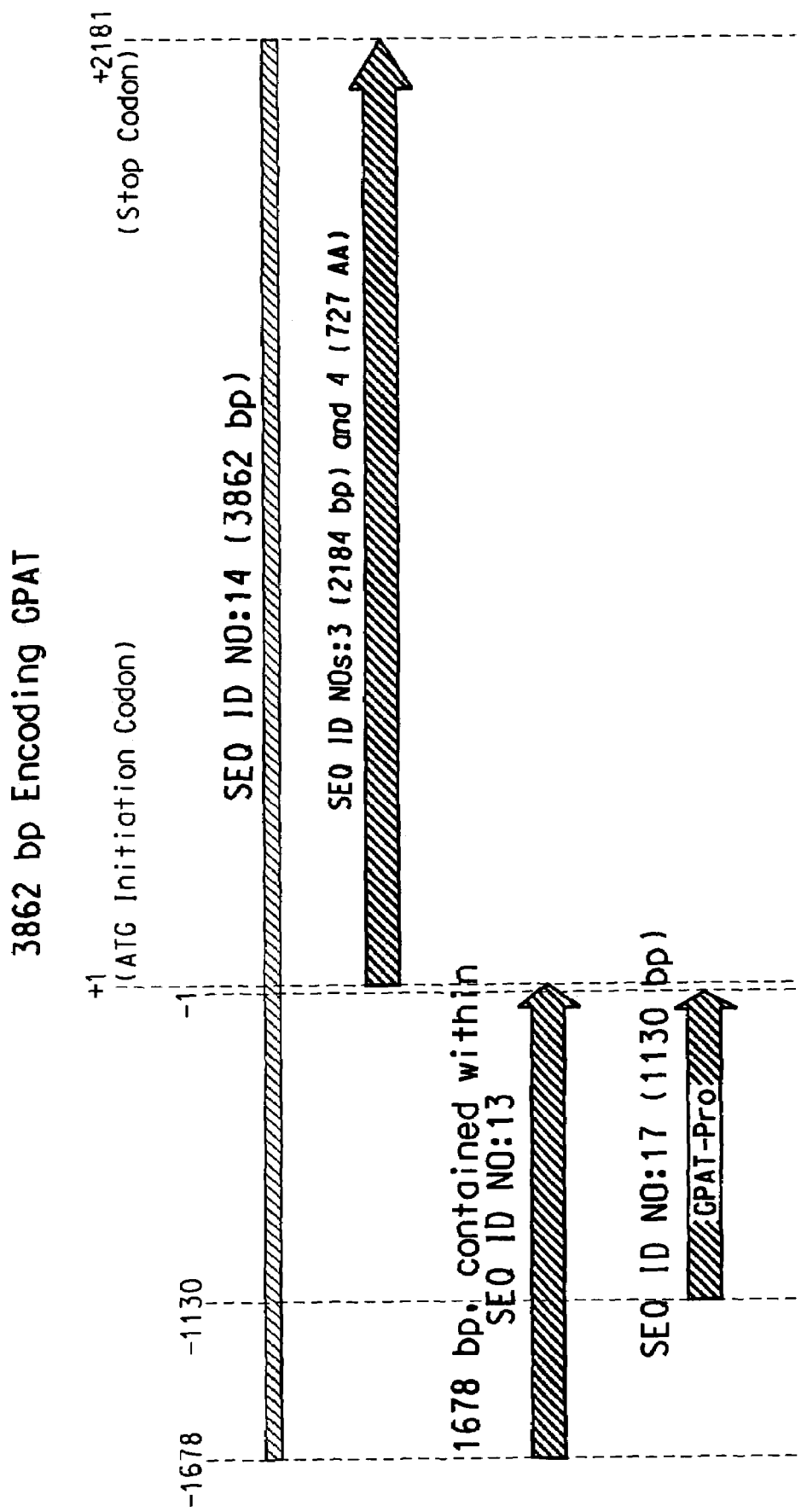

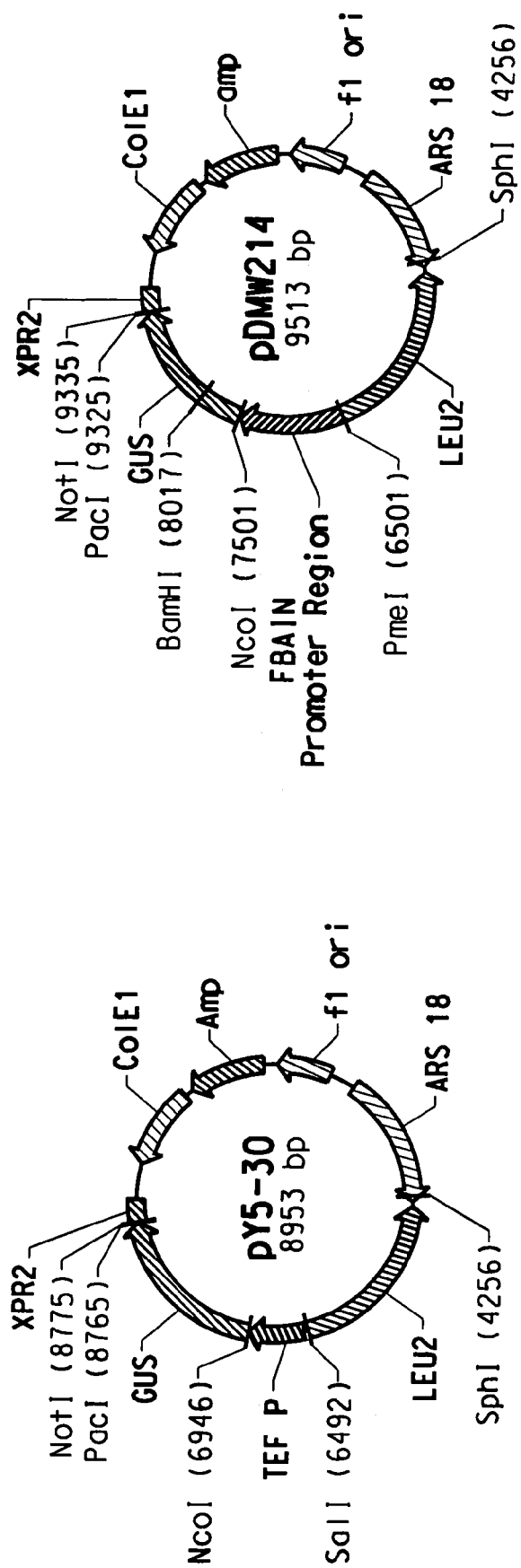
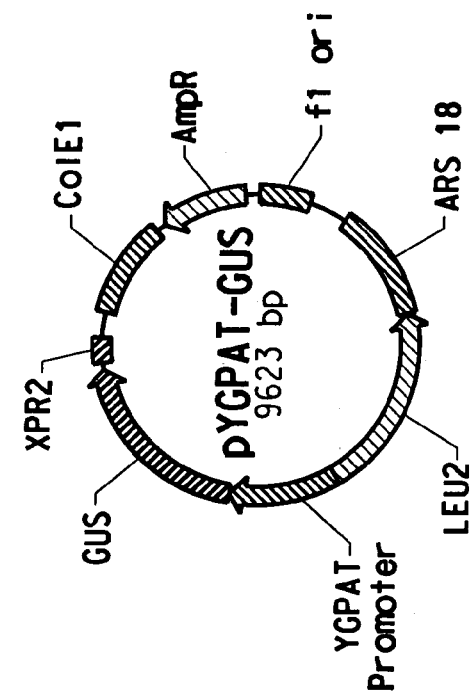
FIG. 2A
FIG. 2B
FIG. 2C

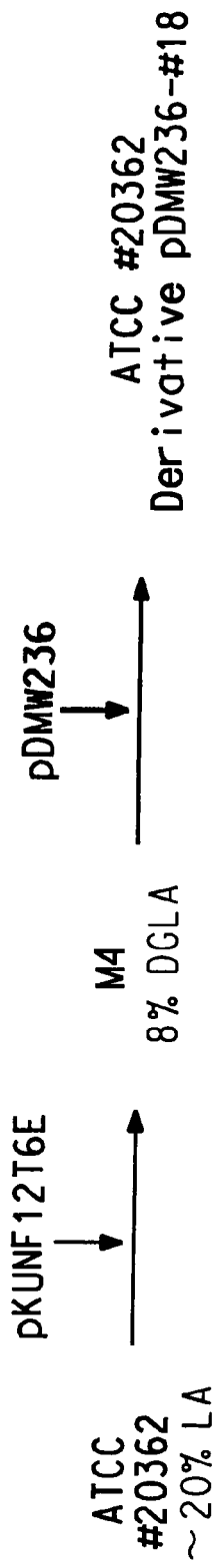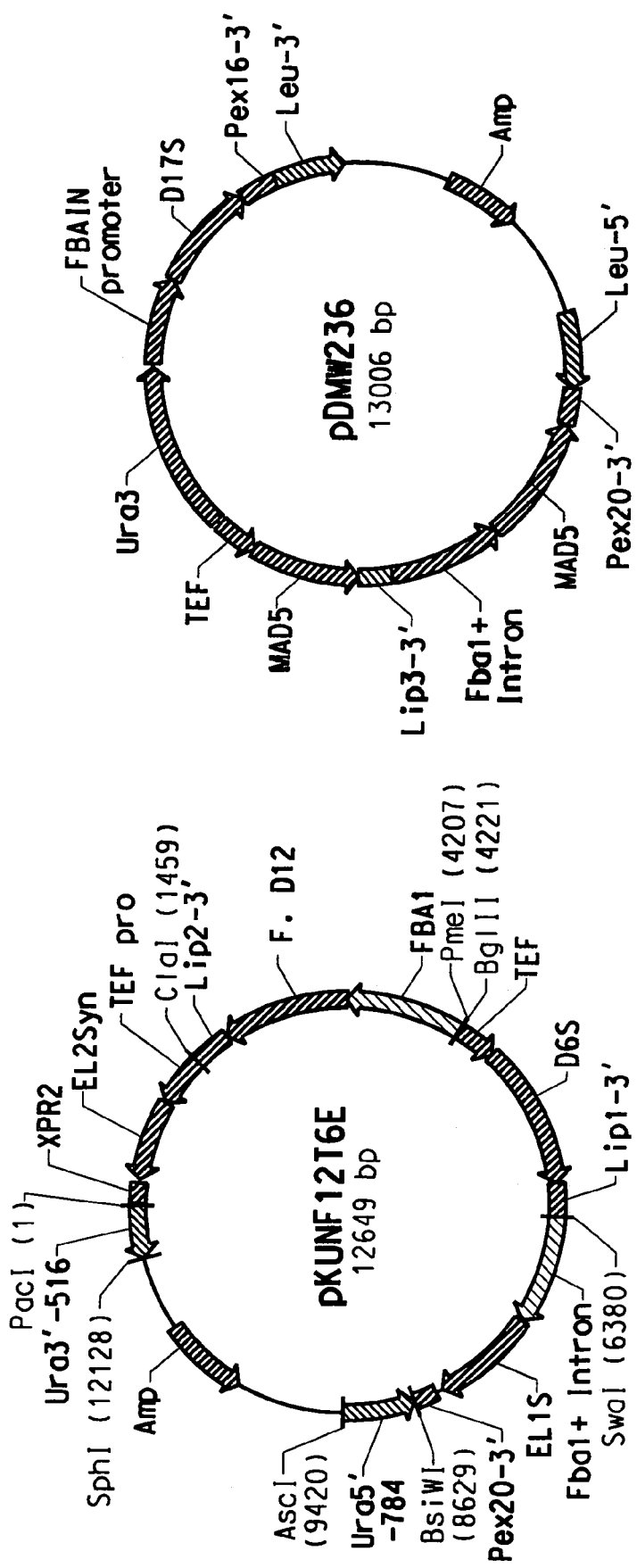
FIG. 3A
FIG. 3B
FIG. 3C

SEQUENCE LISTING

<160> NUMBER OF SEQ ID NOS: 56

<210> SEQ ID NO 1
<211> LENGTH: 750
<212> TYPE: PRT

-continued

<213> ORGANISM: Saccharomyces cerevisiae (GenBank Accession No. AJ314608)
<300> PUBLICATION INFORMATION:
<301> AUTHORS: Zheng,Z. and Zou,J.
<302> TITLE: The initial step of the glycerolipid pathway: identification of glycerol 3-phosphate/dihydroxyacetone phosphate dual substrate acyltransferases in Saccharomyces cerevisiae
<303> JOURNAL: J. Biol. Chem.
<304> VOLUME: 276
<305> ISSUE: 45
<306> PAGES: 41710-41716
<307> DATE: 2001

<400> SEQUENCE: 1

```
Met Pro Ala Pro Lys Leu Thr Glu Lys Ser Ala Ser Lys Ser Thr
1               5                   10                  15

Gln Lys Thr Thr Asn Tyr Ser Ser Ile Glu Ala Lys Ser Ile Tyr Gln
            20                  25                  30

Glu Pro Ser Ala Thr Lys Lys Ile Leu Tyr Ser Ile Ala Thr Trp Leu
            35                  40                  45

Leu Tyr Asn Ile Phe His Cys Phe Arg Glu Ile Arg Gly Arg Gly
    50                  55                  60

Ser Phe Lys Val Pro Gln Gln Gly Pro Val Ile Phe Val Ala Ala Pro
65                  70                  75                  80

His Ala Asn Gln Phe Val Asp Pro Val Ile Leu Met Gly Glu Val Lys
                85                  90                  95

Lys Ser Val Asn Arg Arg Val Ser Phe Leu Ile Ala Glu Ser Ser Leu
            100                 105                 110

Lys Gln Pro Pro Ile Gly Phe Leu Ala Ser Phe Phe Met Ala Ile Gly
            115                 120                 125

Val Val Arg Pro Gln Asp Asn Leu Lys Pro Ala Glu Gly Thr Ile Arg
    130                 135                 140

Val Asp Pro Thr Asp Tyr Lys Arg Val Ile Gly His Asp Thr His Phe
145                 150                 155                 160

Leu Thr Asp Cys Met Pro Lys Gly Leu Ile Gly Leu Pro Lys Ser Met
                165                 170                 175

Gly Phe Gly Glu Ile Gln Ser Ile Glu Ser Asp Thr Ser Leu Thr Leu
            180                 185                 190

Arg Lys Glu Phe Lys Met Ala Lys Pro Glu Ile Lys Thr Ala Leu Leu
            195                 200                 205

Thr Gly Thr Thr Tyr Lys Tyr Ala Ala Lys Val Asp Gln Ser Cys Val
    210                 215                 220

Tyr His Arg Val Phe Glu His Leu Ala His Asn Asn Cys Ile Gly Ile
225                 230                 235                 240

Phe Pro Glu Gly Gly Ser His Asp Arg Thr Asn Leu Leu Pro Leu Lys
                245                 250                 255

Ala Gly Val Ala Ile Met Ala Leu Gly Cys Met Asp Arg His Pro Asp
            260                 265                 270

Val Asn Val Lys Ile Val Pro Cys Gly Met Asn Tyr Phe His Pro His
            275                 280                 285

Lys Phe Arg Ser Arg Ala Val Val Glu Phe Gly Asp Pro Ile Glu Ile
    290                 295                 300

Pro Lys Glu Leu Val Ala Lys Tyr His Asn Ser Glu Thr Asn Arg Asp
305                 310                 315                 320

Ala Val Lys Glu Leu Leu Asp Thr Ile Ser Lys Gly Leu Gln Ser Val
                325                 330                 335

Thr Val Thr Cys Ser Asp Tyr Glu Thr Leu Met Val Val Gln Thr Ile
```

```
                    340             345             350
Arg Arg Leu Tyr Met Thr Gln Phe Ser Thr Lys Leu Pro Leu Pro Leu
        355                 360                 365

Ile Val Glu Met Asn Arg Arg Met Val Lys Gly Tyr Glu Phe Tyr Arg
370                 375                 380

Asn Asp Pro Lys Ile Ala Asp Leu Thr Lys Asp Ile Met Ala Tyr Asn
385                 390                 395                 400

Ala Ala Leu Arg His Tyr Asn Leu Pro Asp His Leu Val Glu Glu Ala
                405                 410                 415

Lys Val Asn Phe Ala Lys Asn Leu Gly Leu Val Phe Phe Arg Ser Ile
            420                 425                 430

Gly Leu Cys Ile Leu Phe Ser Leu Ala Met Pro Gly Ile Ile Met Phe
        435                 440                 445

Ser Pro Val Phe Ile Leu Ala Lys Arg Ile Ser Gln Glu Lys Ala Arg
    450                 455                 460

Thr Ala Leu Ser Lys Ser Thr Val Lys Ile Lys Ala Asn Asp Val Ile
465                 470                 475                 480

Ala Thr Trp Lys Ile Leu Ile Gly Met Gly Phe Ala Pro Leu Leu Tyr
                485                 490                 495

Ile Phe Trp Ser Val Leu Ile Thr Tyr Tyr Leu Arg His Lys Pro Trp
            500                 505                 510

Asn Lys Ile Tyr Val Phe Ser Gly Ser Tyr Ile Ser Cys Val Ile Val
        515                 520                 525

Thr Tyr Ser Ala Leu Ile Val Gly Asp Ile Gly Met Asp Gly Phe Lys
    530                 535                 540

Ser Leu Arg Pro Leu Val Leu Ser Leu Thr Ser Pro Lys Gly Leu Gln
545                 550                 555                 560

Lys Leu Gln Lys Asn Arg Arg Asn Leu Ala Glu Arg Ile Ile Glu Val
                565                 570                 575

Val Asn Asn Phe Gly Ser Glu Leu Phe Pro Asp Phe Asp Ser Ala Ala
            580                 585                 590

Leu Arg Glu Glu Phe Asp Val Ile Asp Glu Glu Glu Asp Arg Lys
        595                 600                 605

Thr Ser Glu Leu Asn Arg Arg Lys Met Leu Arg Lys Gln Lys Ile Lys
    610                 615                 620

Arg Gln Glu Lys Asp Ser Ser Pro Ile Ile Ser Gln Arg Asp Asn
625                 630                 635                 640

His Asp Ala Tyr Glu His His Asn Gln Asp Ser Asp Gly Val Ser Leu
                645                 650                 655

Val Asn Ser Asp Asn Ser Leu Ser Asn Ile Pro Leu Phe Ser Ser Thr
            660                 665                 670

Phe His Arg Lys Ser Glu Ser Ser Leu Ala Ser Thr Ser Val Ala Pro
        675                 680                 685

Ser Ser Ser Ser Glu Phe Glu Val Glu Asn Glu Ile Leu Glu Glu Lys
    690                 695                 700

Asn Gly Leu Ala Ser Lys Ile Ala Gln Ala Val Leu Asn Lys Arg Ile
705                 710                 715                 720

Gly Glu Asn Thr Ala Arg Glu Glu Glu Glu Glu Glu Glu Glu
                725                 730                 735

Glu Glu Glu Glu Glu Glu Glu Gly Lys Glu Gly Asp Ala
            740                 745                 750

<210> SEQ ID NO 2
```

-continued

```
<211> LENGTH: 743
<212> TYPE: PRT
<213> ORGANISM: Saccharomyces cerevisiae (GenBank Accession No.
       AJ311354)
<300> PUBLICATION INFORMATION:
<301> AUTHORS: Zheng,Z. and Zou,J.
<302> TITLE: The initial step of the glycerolipid pathway:
       identification of glycerol 3-phosphate/dihydroxyacetone phosphate
       dual substrate acyltransferases in Saccharomyces cerevisiae
<303> JOURNAL: J. Biol. Chem.
<304> VOLUME: 276
<305> ISSUE: 45
<306> PAGES: 41710-41716
<307> DATE: 2001

<400> SEQUENCE: 2

Met Ser Ala Pro Ala Ala Asp His Asn Ala Ala Lys Pro Ile Pro His
1               5                   10                  15

Val Pro Gln Ala Ser Arg Arg Tyr Lys Asn Ser Tyr Asn Gly Phe Val
            20                  25                  30

Tyr Asn Ile His Thr Trp Leu Tyr Asp Val Ser Val Phe Leu Phe Asn
        35                  40                  45

Ile Leu Phe Thr Ile Phe Phe Arg Glu Ile Lys Val Arg Gly Ala Tyr
    50                  55                  60

Asn Val Pro Glu Val Gly Val Pro Thr Ile Leu Val Cys Ala Pro His
65                  70                  75                  80

Ala Asn Gln Phe Ile Asp Pro Ala Leu Val Met Ser Gln Thr Arg Leu
                85                  90                  95

Leu Lys Thr Ser Ala Gly Lys Ser Arg Ser Arg Met Pro Cys Phe Val
            100                 105                 110

Thr Ala Glu Ser Ser Phe Lys Lys Arg Phe Ile Ser Phe Phe Gly His
        115                 120                 125

Ala Met Gly Gly Ile Pro Val Pro Arg Ile Gln Asp Asn Leu Lys Pro
    130                 135                 140

Val Asp Glu Asn Leu Glu Ile Tyr Ala Pro Asp Leu Lys Asn His Pro
145                 150                 155                 160

Glu Ile Ile Lys Gly Arg Ser Lys Asn Pro Gln Thr Thr Pro Val Asn
                165                 170                 175

Phe Thr Lys Arg Phe Ser Ala Lys Ser Leu Leu Gly Leu Pro Asp Tyr
            180                 185                 190

Leu Ser Asn Ala Gln Ile Lys Glu Ile Pro Asp Asp Glu Thr Ile Ile
        195                 200                 205

Leu Ser Ser Pro Phe Arg Thr Ser Lys Ser Lys Val Val Glu Leu Leu
    210                 215                 220

Thr Asn Gly Thr Asn Phe Lys Tyr Ala Glu Lys Ile Asp Asn Thr Glu
225                 230                 235                 240

Thr Phe Gln Ser Val Phe Asp His Leu His Thr Lys Gly Cys Val Gly
                245                 250                 255

Ile Phe Pro Glu Gly Gly Ser His Asp Arg Pro Ser Leu Leu Pro Ile
            260                 265                 270

Lys Ala Gly Val Ala Ile Met Ala Leu Gly Ala Val Ala Ala Asp Pro
        275                 280                 285

Thr Met Lys Val Ala Val Pro Cys Gly Leu His Tyr Phe His Arg
    290                 295                 300

Asn Lys Phe Arg Ser Arg Ala Val Leu Glu Tyr Gly Glu Pro Ile Val
305                 310                 315                 320

Val Asp Gly Lys Tyr Gly Glu Met Tyr Lys Asp Ser Pro Arg Glu Thr
                325                 330                 335
```

```
Val Ser Lys Leu Leu Lys Lys Ile Thr Asn Ser Leu Phe Ser Val Thr
        340                 345                 350

Glu Asn Ala Pro Asp Tyr Asp Thr Leu Met Val Ile Gln Ala Ala Arg
        355                 360                 365

Arg Leu Tyr Gln Pro Val Lys Val Arg Leu Pro Leu Pro Ala Ile Val
        370                 375                 380

Glu Ile Asn Arg Arg Leu Leu Phe Gly Tyr Ser Lys Phe Lys Asp Asp
385                 390                 395                 400

Pro Arg Ile Ile His Leu Lys Lys Leu Val Tyr Asp Tyr Asn Arg Lys
                405                 410                 415

Leu Asp Ser Val Gly Leu Lys Asp His Gln Val Met Gln Leu Lys Thr
                420                 425                 430

Thr Lys Leu Glu Ala Leu Arg Cys Phe Val Thr Leu Ile Val Arg Leu
        435                 440                 445

Ile Lys Phe Ser Val Phe Ala Ile Leu Ser Leu Pro Gly Ser Ile Leu
        450                 455                 460

Phe Thr Pro Ile Phe Ile Ile Cys Arg Val Tyr Ser Glu Lys Lys Ala
465                 470                 475                 480

Lys Glu Gly Leu Lys Lys Ser Leu Val Lys Ile Lys Gly Thr Asp Leu
                485                 490                 495

Leu Ala Thr Trp Lys Leu Ile Val Ala Leu Ile Leu Ala Pro Ile Leu
                500                 505                 510

Tyr Val Thr Tyr Ser Ile Leu Leu Ile Ile Leu Ala Arg Lys Gln His
                515                 520                 525

Tyr Cys Arg Ile Trp Val Pro Ser Asn Asn Ala Phe Ile Gln Phe Val
        530                 535                 540

Tyr Phe Tyr Ala Leu Leu Val Phe Thr Thr Tyr Ser Ser Leu Lys Thr
545                 550                 555                 560

Gly Glu Ile Gly Val Asp Leu Phe Lys Ser Leu Arg Pro Leu Phe Val
                565                 570                 575

Ser Ile Val Tyr Pro Gly Lys Lys Ile Glu Glu Ile Gln Thr Thr Arg
                580                 585                 590

Lys Asn Leu Ser Leu Glu Leu Thr Ala Val Cys Asn Asp Leu Gly Pro
        595                 600                 605

Leu Val Phe Pro Asp Tyr Asp Lys Leu Ala Thr Glu Ile Phe Ser Lys
        610                 615                 620

Arg Asp Gly Tyr Asp Val Ser Ser Asp Ala Glu Ser Ser Ile Ser Arg
625                 630                 635                 640

Met Ser Val Gln Ser Arg Ser Arg Ser Ser Ile His Ser Ile Gly
                645                 650                 655

Ser Leu Ala Ser Asn Ala Leu Ser Arg Val Asn Ser Arg Gly Ser Leu
        660                 665                 670

Thr Asp Ile Pro Ile Phe Ser Asp Ala Lys Gln Gly Gln Trp Lys Ser
        675                 680                 685

Glu Gly Glu Thr Ser Glu Asp Glu Asp Glu Phe Asp Glu Lys Asn Pro
        690                 695                 700

Ala Ile Val Gln Thr Ala Arg Ser Ser Asp Leu Asn Lys Glu Asn Ser
705                 710                 715                 720

Arg Asn Thr Asn Ile Ser Ser Lys Ile Ala Ser Leu Val Arg Gln Lys
                725                 730                 735

Arg Glu His Glu Lys Lys Glu
        740
```

<210> SEQ ID NO 3
<211> LENGTH: 2184
<212> TYPE: DNA
<213> ORGANISM: Yarrowia lipolytica

<400> SEQUENCE: 3

| | |
|---|---|
| atgtccgaaa ccgaccatct gctggccgcc gagcccgtgg ctgagtaccc ccagtacacg | 60 |
| ccttggccca actcccgaaa atcagtggac acggagtttt ccgcaacctc gtggatttac | 120 |
| gacttggttc tgtggatttt cacggcttgc tttgacattt ttttcagaga aatccggcca | 180 |
| cgtggtgcct tccgaatccc cagaaagggc cccgtgctgt tcgtggctgc cccccacgca | 240 |
| aaccagtttg tggaccccgt catcctcatg aaccaggtca acaggaggc cggacgacga | 300 |
| atctccttcc ttgtggccga agtccatg cgacgagctg cagtcggacg aatgcccga | 360 |
| agcatgaact caattcctgt cgtgcgagct caggacaatg caaaaaaggg agagggaaag | 420 |
| atttacgtcg acgcagagga ccccacaaag atccacggaa tcggcaccca gttcacgaag | 480 |
| cagtgcgagg tgcgaggcct cgtggtctgc tcgtcctctg tcggctcaat tgacgtggct | 540 |
| gagattgtgt ccgacactct gctcattgca agaaaggaat tcaagggccc caaagccaag | 600 |
| gaggctctca aggaatccaa cggaggaatc acatacaagt acgccgacta cgtcaaccag | 660 |
| gccacagtct accgatccgt gttcgacaaa ttgcaccatg gaggctgtgt gggtatcttc | 720 |
| ccagagggag gatctcatga ccgaaccgaa ctgctgcccc ttaaggccgg tgttgctatc | 780 |
| atggctctgg gggctctcgc agaggacccc tcttgtggtg tgcgaatcgt ccctgtggt | 840 |
| ctcaactact ccacgccta caagttccga tctcgggccg tggtggagtt tggctctcct | 900 |
| attgccattc ctccggatct cgtggagaag tacaaggcag gaggagaggc caagcgggag | 960 |
| gctgtcaaga ccgttctaga cattactgcc gctggtctca agtctgtgac tgttcaggtg | 1020 |
| caggatttcg acaccctgat gctgatccag gccattcgac gactctaccg acctcccgga | 1080 |
| aagaagattc ctctgcccat ggttgtagag ctcaaccgtc gacttgtata cgcctacaac | 1140 |
| cactacaagg acgatccccg tatcgaggag atgaagcagg agattcgaaa gtacaacaag | 1200 |
| ttcctgcagg ccatgggtct caaggaccat caggtagaga aggcccgaat ctccaagatt | 1260 |
| gagattctgg gccggcttct gtaccggtcc atcaagcttg tgttcttgtc cattggctgt | 1320 |
| ctccccggtc tgcttttgtt ttctcccatc ttcatcattt ctaagtccat ttccaaaacc | 1380 |
| aaggccaagg aggctctcaa ggcctccagt gtcaaaatca aggctaacga tgtggttgcc | 1440 |
| acttggaagg tgctggttgc aatgggtctg accccagttc tttacattct ctattcactg | 1500 |
| gttggatctg tggtgattcg aaagctcgat ctcatctcct ggttccccac aattcttctt | 1560 |
| cccggcctcg ttttaagcat catcatcaca acctcatacg ccgccctggc tatgggagag | 1620 |
| gccggtatgg acattttcaa gtctcttcga ccacttgcat tggctctcaa cccttccacc | 1680 |
| aaaaactctc tgctcaagct gcaaaatgaa cgaaagcgac ttgtgctcaa gtcttccgag | 1740 |
| ctcgttacct ctttgggccc tgagctgttc ccgacttcc ccgagaactc cattctgcag | 1800 |
| ggaagcgata agtttgagga cgaggagaac tacgaaaacg agaagcgatc gcattccaga | 1860 |
| tccacttctg ccacttctct atctgccatg agcgagggag acggtgatga gcttgttcgg | 1920 |
| gaggtccgaa agggtgctag ctacttccct gtgagtacca cttctgagga cgaagaccaa | 1980 |
| gccatctcgc gagtgggctc tgaggcatct cttgctgaca ttcctctgtt tggtatgtcc | 2040 |
| cgatcacaat ctggagcttc tctttcggaa gcctccacac acggctcttc tactggagct | 2100 |
| gatgccgagg aggctaagac ggaggtgact cgcagaattg cattggcgat ggaggaaaaa | 2160 | cgacgagagc aggatgagga ataa                                              2184

<210> SEQ ID NO 4
<211> LENGTH: 727
<212> TYPE: PRT
<213> ORGANISM: Yarrowia lipolytica
<220> FEATURE:
<221> NAME/KEY: MISC_FEATURE
<223> OTHER INFORMATION: ORF YALI-CDS1055.1 in the Genolevures database
      of Y. lipolytica ORFs (sponsored by the Center for Bioinformatics;
      http://cbi.labri.fr/Genolevures/Y_lipolytica.php)

<400> SEQUENCE: 4

Met Ser Glu Thr Asp His Leu Leu Ala Ala Glu Pro Val Ala Glu Tyr
1               5                   10                  15

Pro Gln Tyr Thr Pro Trp Pro Asn Ser Arg Lys Ser Val Asp Thr Glu
            20                  25                  30

Phe Ser Ala Thr Ser Trp Ile Tyr Asp Leu Val Leu Trp Ile Phe Thr
        35                  40                  45

Ala Cys Phe Asp Ile Phe Phe Arg Glu Ile Arg Pro Arg Gly Ala Phe
    50                  55                  60

Arg Ile Pro Arg Lys Gly Pro Val Leu Phe Val Ala Ala Pro His Ala
65                  70                  75                  80

Asn Gln Phe Val Asp Pro Val Ile Leu Met Asn Gln Val Lys Gln Glu
                85                  90                  95

Ala Gly Arg Arg Ile Ser Phe Leu Val Ala Glu Lys Ser Met Arg Arg
            100                 105                 110

Ala Ala Val Gly Arg Met Ala Arg Ser Met Asn Ser Ile Pro Val Val
        115                 120                 125

Arg Ala Gln Asp Asn Ala Lys Lys Gly Glu Gly Lys Ile Tyr Val Asp
    130                 135                 140

Ala Glu Asp Pro Thr Lys Ile His Gly Ile Gly Thr Gln Phe Thr Lys
145                 150                 155                 160

Gln Cys Glu Val Arg Gly Leu Val Val Cys Ser Ser Val Gly Ser
                165                 170                 175

Ile Asp Val Ala Glu Ile Val Ser Asp Thr Leu Leu Ile Ala Arg Lys
            180                 185                 190

Glu Phe Lys Gly Pro Lys Ala Lys Glu Ala Leu Lys Glu Ser Asn Gly
        195                 200                 205

Gly Ile Thr Tyr Lys Tyr Ala Asp Tyr Val Asn Gln Ala Thr Val Tyr
    210                 215                 220

Arg Ser Val Phe Asp Lys Leu His His Gly Gly Cys Val Gly Ile Phe
225                 230                 235                 240

Pro Glu Gly Gly Ser His Asp Arg Thr Glu Leu Leu Pro Leu Lys Ala
                245                 250                 255

Gly Val Ala Ile Met Ala Leu Gly Ala Leu Ala Glu Asp Pro Ser Cys
            260                 265                 270

Gly Val Arg Ile Val Pro Cys Gly Leu Asn Tyr Phe His Ala Tyr Lys
        275                 280                 285

Phe Arg Ser Arg Ala Val Val Glu Phe Gly Ser Pro Ile Ala Ile Pro
    290                 295                 300

Pro Asp Leu Val Glu Lys Tyr Lys Ala Gly Gly Glu Ala Lys Arg Glu
305                 310                 315                 320

Ala Val Lys Thr Val Leu Asp Ile Thr Ala Ala Gly Leu Lys Ser Val
                325                 330                 335

-continued

```
Thr Val Gln Val Gln Asp Phe Asp Thr Leu Met Leu Ile Gln Ala Ile
            340                 345                 350

Arg Arg Leu Tyr Arg Pro Pro Gly Lys Lys Ile Pro Leu Pro Met Val
        355                 360                 365

Val Glu Leu Asn Arg Arg Leu Val Tyr Ala Tyr Asn His Tyr Lys Asp
    370                 375                 380

Asp Pro Arg Ile Glu Glu Met Lys Gln Glu Ile Arg Lys Tyr Asn Lys
385                 390                 395                 400

Phe Leu Gln Ala Met Gly Leu Lys Asp His Gln Val Glu Lys Ala Arg
                405                 410                 415

Ile Ser Lys Ile Glu Ile Leu Gly Arg Leu Leu Tyr Arg Ser Ile Lys
            420                 425                 430

Leu Val Phe Leu Ser Ile Gly Cys Leu Pro Gly Leu Leu Leu Phe Ser
        435                 440                 445

Pro Ile Phe Ile Ile Ser Lys Ser Ile Ser Lys Thr Lys Ala Lys Glu
    450                 455                 460

Ala Leu Lys Ala Ser Ser Val Lys Ile Lys Ala Asn Asp Val Val Ala
465                 470                 475                 480

Thr Trp Lys Val Leu Val Ala Met Gly Leu Thr Pro Val Leu Tyr Ile
                485                 490                 495

Leu Tyr Ser Leu Val Gly Ser Val Val Ile Arg Lys Leu Asp Leu Ile
            500                 505                 510

Ser Trp Phe Pro Thr Ile Leu Leu Pro Gly Leu Val Leu Ser Ile Ile
        515                 520                 525

Ile Thr Thr Ser Tyr Ala Ala Leu Ala Met Gly Glu Ala Gly Met Asp
    530                 535                 540

Ile Phe Lys Ser Leu Arg Pro Leu Ala Leu Ala Leu Asn Pro Ser Thr
545                 550                 555                 560

Lys Asn Ser Leu Leu Lys Leu Gln Asn Glu Arg Lys Arg Leu Val Leu
                565                 570                 575

Lys Ser Ser Glu Leu Val Thr Ser Leu Gly Pro Glu Leu Phe Pro Asp
            580                 585                 590

Phe Pro Glu Asn Ser Ile Leu Gln Gly Ser Asp Lys Phe Glu Asp Glu
        595                 600                 605

Glu Asn Tyr Glu Asn Glu Lys Arg Ser His Ser Arg Ser Thr Ser Ala
    610                 615                 620

Thr Ser Leu Ser Ala Met Ser Glu Gly Asp Gly Asp Glu Leu Val Arg
625                 630                 635                 640

Glu Val Arg Lys Gly Ala Ser Tyr Phe Pro Val Ser Thr Thr Ser Glu
                645                 650                 655

Asp Glu Asp Gln Ala Ile Ser Arg Val Gly Ser Glu Ala Ser Leu Ala
            660                 665                 670

Asp Ile Pro Leu Phe Gly Met Ser Arg Ser Gln Ser Gly Ala Ser Leu
        675                 680                 685

Ser Glu Ala Ser Thr His Gly Ser Ser Thr Gly Ala Asp Ala Glu Glu
    690                 695                 700

Ala Lys Thr Glu Val Thr Arg Arg Ile Ala Leu Ala Met Glu Glu Lys
705                 710                 715                 720

Arg Arg Glu Gln Asp Glu Glu
                725

<210> SEQ ID NO 5
<211> LENGTH: 24
<212> TYPE: DNA
```

```
<213> ORGANISM: Artificial Sequence
<220> FEATURE:
<223> OTHER INFORMATION: Primer YGPAT-F
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 5
atgtcngaga cygaccayct nctn                                              24

<210> SEQ ID NO 6
<211> LENGTH: 24
<212> TYPE: DNA
<213> ORGANISM: Artificial Sequence
<220> FEATURE:
<223> OTHER INFORMATION: Primer YGPAT-R

<400> SEQUENCE: 6
ytcytcrtcy tgytctcgyc gytt                                              24

<210> SEQ ID NO 7
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 7
gtaatacgac tatagggcac gcgtggtcga cggcccgggc tggt                        44

<210> SEQ ID NO 8
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 8 accagccc                                                                 8

<210> SEQ ID NO 9
<211> LENGTH: 22
<212> TYPE: DNA
<213> ORGANISM: Artificial Sequence
<220> FEATURE:
<223> OTHER INFORMATION: Primer Adaptor-1

<400> SEQUENCE: 9
gtaatacgac tcactatagg gc                                                22

<210> SEQ ID NO 10
<211> LENGTH: 23
```

```
<212> TYPE: DNA
<213> ORGANISM: Artificial Sequence
<220> FEATURE:
<223> OTHER INFORMATION: Primer YGPAT-5R-1

<400> SEQUENCE: 10
gtcaaagcaa gcccgtgaaa atc                                           23

<210> SEQ ID NO 11
<211> LENGTH: 19
<212> TYPE: DNA
<213> ORGANISM: Artificial Sequence
<220> FEATURE:
<223> OTHER INFORMATION: Nested Adaptor Primer 2

<400> SEQUENCE: 11
actatagggc acgcgtggt                                                19

<210> SEQ ID NO 12
<211> LENGTH: 20
<212> TYPE: DNA
<213> ORGANISM: Artificial Sequence
<220> FEATURE:
<223> OTHER INFORMATION: Primer YGPAT-5R-2

<400> SEQUENCE: 12
gtcgtaaatc cacgaggttg                                               20

<210> SEQ ID NO 13
<211> LENGTH: 1781
<212> TYPE: DNA
<213> ORGANISM: Yarrowia lipolytica

<400> SEQUENCE: 13
atccagacga cggcatggga gaacggattg gttttttttt gagttcatca tgtcctgcca     60
acccactgaa aacagggtcc gatgcggaat gatggctttt tactgtagtc agtgtctttt    120
acagaaatac accccagcc atcatatatc ctctccaggc atggaccact gggtacactc     180
gtgacgtgtc ataatcactg agccagtata cgaacaaaat acaatcctgc catcgtactc    240
actcaaacaa ccgtgttcaa taaggaagct gggccagaca gctgaaatgt accaaccagt    300
cgaggtgaag cacagaacaa gaagacacaa accacgatct ttacaagaat gtactgtagt    360
acatacagca cgagtagtgt acgaagtttt tgtcagacac gtgacttgct cgtaaattag    420
ccaatatgac acaccgccaa ggacctcgga tgcgtgcggt gcgtgcggtg cgtgcggtgt    480
gtgcggtgcg tgcgtatgta ccccactctg tgtcgatcag ccgacagtga tgttccggaa    540
gtgcggtaca acttttcttg tcgacctgag ataccgaggt gcgcaggggg atcaactttt    600
gtgtctcaga gggacccaag tgcgtacgga gagtacagta catactgtag ctaacggtag    660
caggcgaact actggtacat acctcccccg gaatatgtac aggcataatg cgtatctgtg    720
ggacatgtgg tcgttgcgcc attatgtaag cagcgtgtac tcctctgact gtccatatgg    780
tttgctccat ctcaccctca tcgttttcat tgttcacagg cggccacaaa aaaactgtct    840
tctctccttc tctcttcgcc ttagtctact cggaccagtt ttagtttagc ttggcgccac    900
tggataaatg agacctcagg ccttgtgatg aggaggtcac ttatgaagca tgttaggagg    960
tgcttgtatg gatagagaag cacccaaaat aataagaata ataataaaac aggggggcgtt   1020 gtcatttcat atcgtgtttt caccatcaat acacctccaa acaatgccct tcatgtggcc   1080
agccccaata ttgtcctgta gttcaactct atgcagctcg tatcttattg agcaagtaaa   1140
```

| | |
|---|---|
| actctgtcag ccgatattgc ccgacccgcg acaagggtca acaaggtggt gtaaggcctt | 1200 |
| cgcagaagtc aaaactgtgc caaacaaaca tctagagtct ctttggtgtt tctcgcatat | 1260 |
| atttaatcgg ctgtcttacg tatttggcct cggtaccgga ctaatttcgg atcatcccca | 1320 |
| atacgctttt tcttcgcagc tgtcaacagt gtccatgatc tatccaccta aatgggtcat | 1380 |
| atgaggcgta taattcgtg gtgctgataa taattcccat atatttgaca caaaacttcc | 1440 |
| cccctagac atacatctca caatctcact tcttgtgctt ctgtcacaca tctcctccag | 1500 |
| ctgacttcaa ctcacacctc tgccccagtt ggtctacagc ggtataaggt ttctccgcat | 1560 |
| agaggtgcac cactcctccc gatacttgtt tgtgtgactt gtgggtcacg acatatatat | 1620 |
| ctacacacat tgcgccaccc tttggttctt ccagcacaac aaaaacacga cacgctaaat | 1680 |
| gtccgaaacc gaccatctgc tggccgccga gcccgtggct gagtaccccc agtacacgcc | 1740 |
| ttggcccaac tcccgaaaat cagtggacac ggagttttcc g | 1781 |

<210> SEQ ID NO 14
<211> LENGTH: 3862
<212> TYPE: DNA
<213> ORGANISM: Yarrowia lipolytica

<400> SEQUENCE: 14

| | |
|---|---|
| atccagacga cggcatggga gaacggattg gttttttttt gagttcatca tgtcctgcca | 60 |
| acccactgaa aacagggtcc gatgcggaat gatggctttt tactgtagtc agtgtctttt | 120 |
| acagaaatac accccagcc atcatatatc ctctccaggc atggaccact gggtacactc | 180 |
| gtgacgtgtc ataatcactg agccagtata cgaacaaaat acaatcctgc catcgtactc | 240 |
| actcaaacaa ccgtgttcaa taaggaagct gggccagaca gctgaaatgt accaaccagt | 300 |
| cgaggtgaag cacagaacaa gaagacacaa accacgatct ttacaagaat gtactgtagt | 360 |
| acatacagca cgagtagtgt acgaagtttt tgtcagacac gtgacttgct cgtaaattag | 420 |
| ccaatatgac acaccgccaa ggacctcgga tgcgtgcggt gcgtgcggtg cgtgcggtgt | 480 |
| gtgcggtgcg tgcgtatgta ccccactctg tgtcgatcag ccgacagtga tgttccggaa | 540 |
| gtgcggtaca acttttcttg tcgacctgag ataccgaggt tgcgcagggg atcaacttt | 600 |
| gtgtctcaga gggacccaag tgcgtacgga gagtacagta catactgtag ctaacggtag | 660 |
| caggcgaact actggtacat acctcccccg gaatatgtac aggcataatg cgtatctgtg | 720 |
| ggacatgtgg tcgttgcgcc attatgtaag cagcgtgtac tcctctgact gtccatatgg | 780 |
| tttgctccat ctcaccctca tcgttttcat tgttcacagg cggccacaaa aaaactgtct | 840 |
| tctctccttc tctcttcgcc ttagtctact cggaccagtt ttagtttagc ttggcgccac | 900 |
| tggataaatg agacctcagg ccttgtgatg aggaggtcac ttatgaagca tgttaggagg | 960 |
| tgcttgtatg gatagagaag cacccaaaat aataagaata ataataaaac aggggcgtt | 1020 |
| gtcatttcat atcgtgtttt caccatcaat acacctccaa acaatgccct tcatgtggcc | 1080 |
| agccccaata ttgtcctgta gttcaactct atgcagctcg tatcttattg agcaagtaaa | 1140 |
| actctgtcag ccgatattgc ccgacccgcg acaagggtca acaaggtggt gtaaggcctt | 1200 |
| cgcagaagtc aaaactgtgc caaacaaaca tctagagtct ctttggtgtt tctcgcatat | 1260 |
| atttaatcgg ctgtcttacg tatttggcct cggtaccgga ctaatttcgg atcatcccca | 1320 |
| atacgctttt tcttcgcagc tgtcaacagt gtccatgatc tatccaccta aatgggtcat | 1380 |
| atgaggcgta taattcgtg gtgctgataa taattcccat atatttgaca caaaacttcc | 1440 |
| cccctagac atacatctca caatctcact tcttgtgctt ctgtcacaca tctcctccag | 1500 |

-continued

```
ctgacttcaa ctcacacctc tgccccagtt ggtctacagc ggtataaggt ttctccgcat    1560
agaggtgcac cactcctccc gatacttgtt tgtgtgactt gtgggtcacg acatatatat    1620
ctacacacat tgcgccaccc tttggttctt ccagcacaac aaaaacacga cacgctaaat    1680
gtccgaaacc gaccatctgc tggccgccga gcccgtggct gagtaccccc agtacacgcc    1740
ttggcccaac tcccgaaaat cagtggacac ggagttttcc gcaacctcgt ggatttacga    1800
cttggttctg tggattttca cggcttgctt tgacattttt ttcagagaaa tccggccacg    1860
tggtgccttc cgaatcccca gaaagggccc cgtgctgttc gtggctgccc ccacgcaaa    1920 ccagtttgtg gaccccgtca tcctcatgaa ccaggtcaaa caggaggccg gacgacgaat    1980
ctccttcctt gtggccgaga agtccatgcg acgagctgca gtcggacgaa tggcccgaag    2040
catgaactca attcctgtcg tgcgagctca ggacaatgca aaaagggag agggaaagat    2100 ttacgtcgac gcagaggacc ccacaaagat ccacggaatc ggcacccagt tcacgaagca    2160
gtgcgaggtg cgaggcctcg tggtctgctc gtcctctgtc ggctcaattg acgtggctga    2220
gattgtgtcc gacactctgc tcattgcaag aaaggaattc aagggcccca agccaaggaa    2280
ggctctcaag gaatccaacg gaggaatcac atacaagtac gccgactacg tcaaccaggc    2340
cacagtctac cgatccgtgt tcgacaaaat gcaccatgga ggctgtgtgg gtatcttccc    2400
agagggagga tctcatgacc gaaccgaact gctgcccctt aaggccggtg ttgctatcat    2460
ggctctgggg gctctcgcag aggacccctc ttgtggtgtg cgaatcgtcc cctgtggtct    2520
caactacttc cacgcctaca agttccgatc tcgggccgtg gtggagtttg gctctcctat    2580
tgccattcct ccggatctcg tggagaagta caaggcagga ggagaggcca agcgggaggc    2640
tgtcaagacc gttctagaca ttactgccgc tggtctcaag tctgtgactg ttcaggtgca    2700
ggatttcgac accctgatgc tgatccaggc cattcgacga ctctaccgac ctcccggaaa    2760
gaagattcct ctgcccatgg ttgtagagct caaccgtcga cttgtatacg cctacaacca    2820
ctacaaggac gatccccgta tcgaggagat gaagcaggag attcgaaagt acaacaagtt    2880
cctgcaggcc atgggtctca aggaccatca ggtagagaag gcccgaatct ccaagattga    2940
gattctgggc cggcttctgt accggtccat caagcttgtg ttcttgtcca ttggctgtct    3000
ccccggtctg cttttgtttt ctcccatctt catcattcct aagtccattt ccaaaaccaa    3060
ggccaaggag gctctcaagg cctccagtgt caaaatcaag gctaacgatg tggttgccac    3120
ttggaaggtc ctggttgcaa tgggtctgac cccagttctt tacattctct attcactggt    3180
tggatctgtg gtgattcgaa agctcgatct catctcctgg ttccccacaa ttcttcttcc    3240
cggcctcgtt ttaagcatca tcatcacaac ctcatacgcc gccctggcta tgggagaggc    3300
cggtatggac attttcaagt ctcttcgacc acttgcattg gctctcaacc cttccaccaa    3360
aaactctctg ctcaagctgc aaaatgaacg aaagcgactt gtgctcaagt cttccgagct    3420
cgttacctct ttgggccctg agctgttccc cgacttcccc gagaactcca ttctgcaggg    3480
aagcgataag tttgaggacg aggagaacta cgaaaacgag aagcgatcgc attccagatc    3540
cacttctgcc acttctctat ctgccatgag cgagggagac ggtgatgagc ttgttcggga    3600
ggtccgaaag ggtgctagct acttccctgt gagtaccact tctgaggacg aagaccaagc    3660
catctcgcga gtgggctctg aggcatctct tgctgacatt cctctgtttg gtatgtcccg    3720
atcacaatct ggagcttctc tttcggaagc ctccacacac ggctcttcta ctggagctga    3780
tgccgaggag gctaagacgg aggtgactcg cagaattgca ttggcgatgg aggaaaaacg    3840
```

<210> SEQ ID NO 15
<211> LENGTH: 8953
<212> TYPE: DNA
<213> ORGANISM: Artificial Sequence
<220> FEATURE:
<223> OTHER INFORMATION: Plasmid pY5-30

<400> SEQUENCE: 15

```
ggtggagctc cagcttttgt tccctttagt gagggttaat ttcgagcttg gcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
cccctgacga gcatcacaaa aatcgacgct caagtcagag gtggcgaaac ccgacaggac     540
tataaagata ccaggcgttt ccccctggaa gctccctcgt gcgctctcct gttccgaccc     600
tgccgcttac cggatacctg tccgcctttc tcccttcggg aagcgtggcg ctttctcata     660
gctcacgctg taggtatctc agttcggtgt aggtcgttcg ctccaagctg ggctgtgtgc     720
acgaaccccc cgttcagccc gaccgctgcg ccttatccgg taactatcgt cttgagtcca     780
acccggtaag acacgactta tcgccactgg cagcagccac tggtaacagg attagcagag     840
cgaggtatgt aggcggtgct acagagttct tgaagtggtg gcctaactac ggctacacta     900
gaaggacagt atttggtatc tgcgctctgc tgaagccagt taccttcgga aaaagagttg     960
gtagctcttg atccggcaaa caaaccaccg ctggtagcgg tggtttttttt gtttgcaagc    1020
agcagattac gcgcagaaaa aaaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt taaatcaatc taagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
```

```
caaaaaaggg aataagggcg acacggaaat gttgaatact catactcttc cttttcaat    2100 attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcggtg tggtggttac gcgcagcgtg accgctacac     2280
ttgccagcgc cctagcgccc gctccttcg ctttcttccc ttcctttctc gccacgttcg     2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
cctgatagac ggttttcgc cctttgacgt tggagtccac gttctttaat agtggactct     2520
tgttccaaac tggaacaaca ctcaacccta tctcggtcta ttcttttgat ttataaggga    2580
ttttgccgat tcggcctat tggttaaaaa atgagctgat ttaacaaaaa tttaacgcga     2640
attttaacaa atattaacg cttacaattt ccattcgcca ttcaggctgc gcaactgttg     2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatccccc tcgttcagtg tcaactgtaa tggtaggaaa ttaccatact     3900
tttgaagaag caaaaaaat gaaagaaaaa aaaaatcgta tttccaggtt agacgttccg     3960
cagaatctag aatgcggtat gcggtacatt gttcttcgaa cgtaaaagtt gcgctccctg    4020
agatattgta cattttgct tttacaagta caagtacatc gtacaactat gtactactgt     4080
tgatgcatcc acaacagttt gttttgtttt tttttgtttt ttttttttct aatgattcat    4140
taccgctatg tataccactg tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
```

```
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620 tccaccccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc ttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagagggggg    5640
ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagaccctgc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300 gcactttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aataaatgat gtcgactcag gcgacgacgg aattcctgca gcccatctgc agaattcagg    6540
agagaccggg ttggcggcgt atttgtgtcc caaaaacag ccccaattgc cccaattgac    6600
cccaaattga cccagtagcg ggcccaaccc cggcgagagc ccccttcacc ccacatatca    6660
aacctccccc ggttcccaca cttgccgtta agggcgtagg gtactgcagt ctggaatcta    6720
cgcttgttca gactttgtac tagtttcttt gtctggccat ccgggtaacc catgccggac    6780
```

-continued

```
gcaaaataga ctactgaaaa ttttttttgct ttgtggttgg gactttagcc aagggtataa    6840
aagaccaccg tccccgaatt acctttcctc ttcttttctc tctctccttg tcaactcaca    6900
cccgaaatcg ttaagcattt ccttctgagt ataagaatca ttcaccatgg atggtacgtc    6960
ctgtagaaac cccaacccgt gaaatcaaaa aactcgacgg cctgtgggca ttcagtctgg    7020
atcgcgaaaa ctgtggaatt gatcagcgtt ggtgggaaag cgcgttacaa gaaagccggg    7080
caattgctgt gccaggcagt tttaacgatc agttcgccga tgcagatatt cgtaattatg    7140
cgggcaacgc ctggtatcag cgcgaagtct ttataccgaa aggttgggca ggccagcgta    7200
tcgtgctgcg tttcgatgcg gtcactcatt acggcaaagt gtgggtcaat aatcaggaag    7260
tgatggagca tcagggcggc tatacgccat ttgaagccga tgtcacgccg tatgttattg    7320
ccgggaaaag tgtacgtatc accgtttgtg tgaacaacga actgaactgg cagactatcc    7380
cgccgggaat ggtgattacc gacgaaaacg caagaaaaa gcagtcttac ttccatgatt    7440
tctttaacta tgccgggatc catcgcagcg taatgctcta caccacgccg aacacctggg    7500
tggacgatat caccgtggtg acgcatgtcg cgcaagactg taaccacgcg tctgttgact    7560
ggcaggtggt ggccaatggt gatgtcagcg ttgaactgcg tgatgcggat caacaggtgg    7620
ttgcaactgg acaaggcact agcgggactt gcaagtggt gaatccgcac ctctggcaac    7680
cgggtgaagg ttatctctat gaactgtgcg tcacagccaa aagccagaca gagtgtgata    7740
tctacccgct tcgcgtcggc atccggtcag tggcagtgaa gggcgaacag ttcctgatta    7800
accacaaacc gttctacttt actggctttg gtcgtcatga agatgcggac ttacgtggca    7860
aaggattcga taacgtgctg atggtgcacg accacgcatt aatggactgg attggggcca    7920
actcctaccg tacctcgcat tacccttacg ctgaagagat gctcgactgg gcagatgaac    7980
atggcatcgt ggtgattgat gaaactgctg ctgtcggctt taacctctct ttaggcattg    8040
gtttcgaagc gggcaacaag ccgaaagaac tgtacagcga agaggcagtc aacggggaaa    8100
ctcagcaagc gcacttacag gcgattaaag agctgatagc gcgtgacaaa aaccacccaa    8160
gcgtggtgat gtggagtatt gccaacgaac cggatacccg tccgcaagtg cacgggaata    8220
tttcgccact ggcggaagca acgcgtaaac tcgacccgac gcgtccgatc acctgcgtca    8280
atgtaatgtt ctgcgacgct cacaccgata ccatcagcga tctctttgat gtgctgtgcc    8340
tgaaccgtta ttacggatgg tatgtccaaa gcggcgattt ggaaacggca gagaaggtac    8400 tggaaaaga acttctggcc tggcaggaga aactgcatca gccgattatc atcaccgaat    8460
acggcgtgga tacgttagcc gggctgcact caatgtacac cgacatgtgg agtgaagagt    8520
atcagtgtgc atggctggat atgtatcacc gcgtctttga tcgcgtcagc gccgtcgtcg    8580
gtgaacaggt atggaatttc gccgattttg cgacctcgca aggcatattg cgcgttggcg    8640
gtaacaagaa agggatcttc actcgcgacc gcaaaccgaa gtcggcggct tttctgctgc    8700
aaaaacgctg gactggcatg aacttcggtg aaaaaccgca gcaggaggc aaacaatgat    8760 taattaacta gagcggccgc caccgcggcc cgagattccg gcctcttcgg ccgccaagcg    8820
acccgggtgg acgtctagag gtacctagca attaacagat agtttgccgg tgataattct    8880
cttaacctcc cacactcctt tgacataacg atttatgtaa cgaaactgaa atttgaccag    8940
atattgtgtc cgc                                                       8953
```

<210> SEQ ID NO 16
<211> LENGTH: 995
<212> TYPE: DNA

<213> ORGANISM: Yarrowia lipolytica
<220> FEATURE:
<221> NAME/KEY: misc_feature
<223> OTHER INFORMATION: Promoter FBAIN

<400> SEQUENCE: 16

```
agtgtacgca gtactataga ggaacaattg ccccggagaa gacggccagg ccgcctagat      60
gacaaattca acaactcaca gctgactttc tgccattgcc actagggggg ggcctttta     120
tatggccaag ccaagctctc cacgtcggtt gggctgcacc caacaataaa tgggtagggt    180
tgcaccaaca aagggatggg atgggggggta aagatacga ggataacggg gctcaatggc    240
acaaataaga acgaatactg ccattaagac tcgtgatcca gcgactgaca ccattgcatc    300
atctaagggc ctcaaaacta cctcggaact gctgcgctga tctggacacc acagaggttc    360
cgagcacttt aggttgcacc aaatgtccca ccaggtgcag gcagaaaacg ctggaacagc    420
gtgtacagtt tgtcttaaca aaaagtgagg gcgctgaggt cgagcagggt ggtgtgactt    480
gttatagcct ttagagctgc gaaagcgcgt atggatttgg ctcatcaggc cagattgagg    540
gtctgtggac acatgtcatg ttagtgtact tcaatcgccc cctggatata gccccgacaa    600
taggccgtgg cctcattttt ttgccttccg cacatttcca ttgctcggta cccacacctt    660
gcttctcctg cacttgccaa ccttaatact ggtttacatt gaccaacatc ttacaagcgg    720
ggggcttgtc tagggtatat ataaacagtg gctctcccaa tcggttgcca gtctcttttt    780
tcctttcttt ccccacagat tcgaaatcta aactacacat cacacaatgc ctgttactga    840
cgtccttaag cgaaagtccg gtgtcatcgt cggcgacgat gtccgagccg tgagtatcca    900
cgacaagatc agtgtcgaga cgacgcgttt tgtgtaatga cacaatccga aagtcgctag    960
caacacacac tctctacaca aactaaccca gctct                               995
```

<210> SEQ ID NO 17
<211> LENGTH: 1130
<212> TYPE: DNA
<213> ORGANISM: Yarrowia lipolytica
<220> FEATURE:
<221> NAME/KEY: misc_feature
<223> OTHER INFORMATION: Promoter GPAT ("GPATPro")

<400> SEQUENCE: 17

```
caacttttct tgtcgacctg agataccgag gttgcgcagg ggatcaactt ttgtgtctca      60
gagggaccca agtgcgtacg gagagtacag tacatactgt agctaacggt agcaggcgaa    120
ctactggtac atacctcccc cggaatatgt acaggcataa tgcgtatctg tgggacatgt    180
ggtcgttgcg ccattatgta agcagcgtgt actcctctga ctgtccatat ggtttgctcc    240
atctcacccct catcgttttc attgttcaca ggcggccaca aaaaaactgt cttctctcct    300
tctctcttcg ccttagtcta ctcggaccag ttttagttta gcttggcgcc actggataaa    360
tgagacctca ggccttgtga tgaggagtc acttatgaag catgttagga ggtgcttgta    420
tggatagaga agcacccaaa ataataagaa taataataaa acaggggggcg ttgtcatttc    480
atatcgtgtt tcaccatca atacacctcc aaacaatgcc cttcatgtgg ccagccccaa    540
tattgtcctg tagttcaact ctatgcagct cgtatcttat tgagcaagta aaactctgtc    600
agccgatatt gcccgacccg cgacaagggt caacaaggtg gtgtaaggcc ttcgcagaag    660
tcaaaactgt gccaaacaaa catctagagt ctctttggtg tttctcgcat atatttaatc    720
ggctgtctta cgtatttggc ctcggtaccg gactaatttc ggatcatccc caatacgctt    780
tttcttcgca gctgtcaaca gtgtccatga tctatccacc taaatgggtc atatgaggcg    840
```

```
tataatttcg tggtgctgat aataattccc atatatttga cacaaaactt ccccccctag    900
acatacatct cacaatctca cttcttgtgc ttctgtcaca catctcctcc agctgacttc    960
aactcacacc tctgcccag ttggtctaca gcggtataag gtttctccgc atagaggtgc   1020
accactcctc ccgatacttg tttgtgtgac ttgtgggtca cgacatatat atctacacac   1080
attgcgccac cctttggttc ttccagcaca acaaaaacac gacacgctaa             1130
```

<210> SEQ ID NO 18
<211> LENGTH: 22
<212> TYPE: DNA
<213> ORGANISM: Artificial Sequence
<220> FEATURE:
<223> OTHER INFORMATION: Primer GPAT-5-1

<400> SEQUENCE: 18

```
caacttttct tgtcgacctg ag                                             22
```

<210> SEQ ID NO 19
<211> LENGTH: 34
<212> TYPE: DNA
<213> ORGANISM: Artificial Sequence
<220> FEATURE:
<223> OTHER INFORMATION: Primer GPAT-5-2

<400> SEQUENCE: 19

```
gatcccatgg ttagcgtgtc gtgttttgt tgtg                                 34
```

<210> SEQ ID NO 20
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 20

```
taaccctcac taaagggaac aaaagctgga gctccaccgc ggacacaata tctggtcaaa     60
tttcagtttc gttacataaa tcgttatgtc aaaggagtgt gggaggttaa gagaattatc    120
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc aggtaggact ggacaaagaa gttgccgaac agagcgagca gggtgatcat    300
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccaccag gatagcctgt cggatggtct cgacgcacat    780
```

```
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca   1020
gacagaggag ttggccatgg tgaatgattc ttatactcag aaggaaatgc ttaacgattt   1080
cgggtgtgag ttgacaagga gagagagaaa agaaggagaa aggtaattcg gggacggtgg   1140
tcttttatac ccttggctaa agtcccaacc acaaagcaaa aaaattttca gtagtctatt   1200
ttgcgtccgg catgggttac ccggatggcc agacaaagaa actagtacaa agtctgaaca   1260
agcgtagatt ccagactgca gtaccctacg cccttaacgg caagtgtggg aaccggggga   1320
ggtttgatat gtgggtgaa gggggctctc gccggggttg ggcccgctac tgggtcaatt    1380
tggggtcaat tggggcaatt ggggctgttt tttgggacac aaatacgccg ccaacccggt   1440
ctctcctgaa ttctgcatcg atcgaggaag aggacaagcg gctgcttctt aagtttgtga   1500
catcagtatc caaggcacca ttgcaaggat tcaaggcttt gaacccgtca tttgccattc   1560
gtaacgctgg tagacaggtt gatcggttcc ctacggcctc cacctgtgtc aatcttctca   1620
agctgcctga ctatcaggac attgatcaac ttcgaagaa acttttgtat gccattcgat    1680
cacatgctgt tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcgggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcg    3120 cagactcaga atccgtcaca gtagttgagg tgacggtgcg tctaagcgca gggttctgct   3180
```

-continued

```
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420 gaaaaagag actggcaacc gattgggaga gccactgttt atatataccc tagacaagcc     3480
ccccgcttgt aagatgttgg tcaatgtaaa ccagtattaa ggttggcaag tgcaggagaa    3540
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata   3720
acaagtcaca ccaccctgct cgacctcagc gccctcactt tttgttaaga caaactgtac    3780
acgctgttcc agcgttttct gcctgcacct gtgggacat ttggtgcaac ctaaagtgct     3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctacccccc atcccatccc tttgttggtg    4020
caaccctacc catttattgt tgggtgcagc ccaaccgacg tggagagctt ggcttggcca    4080
tataaaaagg cccccccccta gtggcaatgg cagaaagtca gctgtgagtt gttgaatttg   4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgccccaa    4320
ttgaccccaa attgacccag tagcgggccc aaccccggcg agagccccct tcaccccaca    4380
tatcaaacct cccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catggctgcc    4680
gctccctctg tgcgaacctt tacccgagcc gaggttctga acgctgaggc tctgaacgag    4740
ggcaagaagg acgctgaggc tcccttcctg atgatcatcg acaacaaggt gtacgacgtc    4800
cgagagttcg tccctgacca tcctggaggc tccgtgattc tcacccacgt tggcaaggac    4860
ggcaccgacg tctttgacac ctttcatccc gaggctgctt gggagactct cgccaacttc    4920
tacgttggag acattgacga gtccgaccga gacatcaaga acgatgactt tgccgctgag    4980
gtccgaaagc tgcgaaccct gttccagtct ctcggctact acgactcctc taaggcctac    5040
tacgccttca aggtctcctt caacctctgc atctggggac tgtccaccgt cattgtggcc    5100 aagtgggtc agacctccac cctcgccaac gtgctctctg ctgccctgct cggcctgttc     5160
tggcagcagt gcggatggct ggctcacgac tttctgcacc accaggtctt ccaggaccga    5220 ttctgggggtg atctcttcgg agccttcctg ggaggtgtct gccagggctt ctcctcttcc    5280
tggtggaagg acaagcacaa cactcaccat gccgctccca acgtgcatgg cgaggatcct    5340
gacattgaca cccaccctct cctgacctgg tccgagcacg ctctggagat gttctccgac    5400
gtccccgatg aggagctgac ccgaatgtgt tctcgattca tggtcctgaa ccagacctgg    5460
ttctacttcc ccattctctc cttcgctcga ctgtcttggt gcctccagtc cattctcttt    5520
```

```
gtgctgccca acggtcaggc tcacaagccc tccggagctc gagtgcccat ctccctggtc    5580
gagcagctgt ccctcgccat gcactggacc tggtacctcg ctaccatgtt cctgttcatc    5640
aaggatcctg tcaacatgct cgtgtacttc ctggtgtctc aggctgtgtg cggaaacctg    5700
ctcgccatcg tgttctccct caaccacaac ggtatgcctg tgatctccaa ggaggaggct    5760
gtcgacatgg atttctttac caagcagatc atcactggtc gagatgtcca tcctggactg    5820
ttcgccaact ggttcaccgg tggcctgaac taccagatcg agcatcacct gttcccttcc    5880
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg ggcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctggggaaa ggttctatat acactttccg gaataccgta gtttccgatg ttatcaatgg    6240
gggcagccag gatttcaggc acttcggtgt ctcggggtga atggcgttc ttggcctcca     6300 tcaagtcgta ccatgtcttc atttgcctgt caaagtaaaa cagaagcaga tgaagaatga    6360
acttgaagtg aaggaattta aattgccccg gagaagacgg ccaggccgcc tagatgacaa    6420
attcaacaac tcacagctga ctttctgcca ttgccactag ggggggggcct ttttatatgg    6480 ccaagccaag ctctccacgt cggttgggct gcacccaaca ataaatgggt agggttgcac    6540
caacaaaggg atgggatggg gggtagaaga tacgaggata acggggctca atggcacaaa    6600
taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840
agcctttaga gctgcgaaag cgcgtatgga tttggctcat caggccagat tgagggtctg    6900
tggacacatg tcatgttagt gtacttcaat cgccccctgg atatagcccc gacaataggc    6960
cgtggcctca tttttttgcc ttccgcacat ttccattgct cggtacccac accttgcttc    7020
tcctgcactt gccaacctta atactggttt acattgacca acatcttaca agcgggggc     7080 ttgtctaggg tatatataaa cagtggctct cccaatcggt tgccagtctc tttttttcctt    7140 tctttcccca cagattcgaa atctaaacta cacatcacac aatgcctgtt actgacgtcc    7200
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgccct    7380
ccaagatgcc tcaggacctg ttcatggacc tcgccagcgc tatcggtgtc cgagctgctc    7440
cctacgtcga tccctggag gctgcctgg ttgcccaggc cgagaagtac attcccacca     7500
ttgtccatca cactcgaggc ttcctggttg ccgtggagtc tccctggct cgagagctgc     7560 ctctgatgaa ccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
```

```
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga agaacgcca agctcgccaa gcaggccaag gctgacgctg     8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatggtt ttgatcatgc acacataagg tccgaccttg tcggcaagct     8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaacttttta    8880
tcggaacctt atctggggca gtgaagtata tgttatggta atagttacga gttagttgaa    8940
cttatagata gactggacta tacggctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgaccttttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gtttttccat aggctccgcc ccctgacga gcatcacaaa aatcgacgct caagtcagag      9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct tgaagtggtg   10080
gcctaactac ggctacacta gaagaacagt atttggtatc tgcgctctgc tgaagccagt   10140
taccttcgga aaaagagttg gtagctcttg atccggcaaa caaaccaccg ctggtagcgg   10200
tggttttttt gtttgcaagc agcagattac gcgcagaaaa aaggatctc aagaagatcc     10260
```

```
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagttt   10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatca ctcatggtta tggcagcact   10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040
acgggataat accgcgccac atagcagaac tttaaaagtg ctcatcattg gaaaacgttc   11100
ttcgggcga aaactctcaa ggatcttacc gctgttgaga tccagttcga tgtaacccac   11160
tcgtgcaccc aactgatctt cagcatcttt tactttcacc agcgtttctg ggtgagcaaa   11220
aacaggaagg caaaatgccg caaaaaaggg aataagggcg acacggaaat gttgaatact   11280
catactcttc ctttttcaat attattgaag catttatcag ggttattgtc tcatgagcgg   11340
atacatattt gaatgtattt agaaaaataa acaaataggg gttccgcgca catttccccg   11400
aaaagtgcca cctgatgcgg tgtgaaatac cgcacagatg cgtaaggaga aaataccgca   11460
tcaggaaatt gtaagcgtta atattttgtt aaaattcgcg ttaaattttt gttaaatcag   11520
ctcattttt aaccaatagg ccgaaatcgg caaaatccct tataaatcaa agaatagac   11580
cgagataggg ttgagtgttg ttccagtttg gaacaagagt ccactattaa agaacgtgga   11640
ctccaacgtc aaagggcgaa aaaccgtcta tcagggcgat ggcccactac gtgaaccatc   11700
accctaatca agttttttgg ggtcgaggtg ccgtaaagca ctaaatcgga acctaaaagg   11760
gagcccccga tttagagctt gacggggaaa gccggcgaac gtggcgagaa aggaagggaa   11820
gaaagcgaaa ggagcgggcg ctagggcgct ggcaagtgta gcggtcacgc tgcgcgtaac   11880
caccacaccc gccgcgctta atgcgccgct acagggcgcg tccattcgcc attcaggctg   11940
cgcaactgtt gggaagggcg atcggtgcgg gcctcttcgc tattacgcca gctggcgaaa   12000
gggggatgtg ctgcaaggcg attaagttgg gtaacgccag ggttttccca gtcacgacgt   12060
tgtaaaacga cggccagtga attgtaatac gactcactat agggcgaatt gggcccgacg   12120
tcgcatgcag tggtggtatt gtgactgggg atgtagttga gaataagtca tacacaagtc   12180
agctttcttc gagcctcata taagtataag tagttcaacg tattagcact gtacccagca   12240
tctccgtatc gagaaacaca acaacatgcc ccattggaca gatcatgcgg atacacaggt   12300
tgtgcagtat catacatact cgatcagaca ggtcgtctga ccatcataca agctgaacaa   12360
gcgctccata cttgcacgct ctctatatac acagttaaat tacatatcca tagtctaacc   12420
tctaacagtt aatcttctgg taagcctccc agccagcctt ctggtatcgc ttggcctcct   12480
caataggatc tcggttctgg ccgtacagac ctcggccgac aattatgata tccgttccgg   12540
tagacatgac atcctcaaca gttcggtact gctgtccgag agcgtctccc ttgtcgtcaa   12600
gaccccacccc gggggtcaga ataagccagt cctcagagtc gcccttaat              12649
```

<210> SEQ ID NO 21
<211> LENGTH: 957
<212> TYPE: DNA
<213> ORGANISM: Mortierella alpina
<220> FEATURE:
<221> NAME/KEY: misc_feature
<223> OTHER INFORMATION: synthetic elongase 1 (codon-optimized)

<400> SEQUENCE: 21

```
atggagtcca ttgctcccct cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca gaccttctc cctcctgcac aacttctgtc tggtctccat ctccgcctac     360
atgtgcggtg gcatcctgta cgaggcttat caggccaact atggactgtt tgagaacgct     420
gccgatcaca ccttcaaggg tctccctatg gctaagatga tctggctctt ctacttctcc     480
aagatcatgg agtttgtcga caccatgatc atggtcctca gaagaacaa ccgacagatt     540
tcctttctgc acgtgtacca ccactcttcc atcttcacca tctggtggct ggtcaccttc     600
gttgctccca acggtgaagc ctacttctct gctgccctga actccttcat ccacgtcatc     660
atgtacggct actactttct gtctgccctg ggcttcaagc aggtgtcgtt catcaagttc     720
tacatcactc gatcccagat gacccagttc tgcatgatgt ctgtccagtc ttcctgggac     780
atgtacgcca tgaaggtcct tggccgacct ggatacccct tcttcatcac cgctctgctc     840
tggttctaca tgtggaccat gctcggtctc ttctacaact tttaccgaaa gaacgccaag     900
ctcgccaagc aggccaaggc tgacgctgcc aaggagaagg ccagaaagct ccagtaa      957
```

<210> SEQ ID NO 22
<211> LENGTH: 318
<212> TYPE: PRT
<213> ORGANISM: Mortierella alpina AX464731

<400> SEQUENCE: 22

```
Met Glu Ser Ile Ala Pro Phe Leu Pro Ser Lys Met Pro Gln Asp Leu
  1               5                  10                  15

Phe Met Asp Leu Ala Thr Ala Ile Gly Val Arg Ala Ala Pro Tyr Val
                 20                  25                  30

Asp Pro Leu Glu Ala Ala Leu Val Ala Gln Ala Glu Lys Tyr Ile Pro
             35                  40                  45

Thr Ile Val His His Thr Arg Gly Phe Leu Val Ala Val Glu Ser Pro
     50                  55                  60

Leu Ala Arg Glu Leu Pro Leu Met Asn Pro Phe His Val Leu Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
                100                 105                 110

Cys Leu Val Ser Ile Ser Ala Tyr Met Cys Gly Gly Ile Leu Tyr Glu
            115                 120                 125

Ala Tyr Gln Ala Asn Tyr Gly Leu Phe Glu Asn Ala Ala Asp His Thr
        130                 135                 140
```

| | | | | | | | | | | | | |
|---|---|---|---|---|---|---|---|---|---|---|---|---|
| Phe | Lys | Gly | Leu | Pro | Met | Ala | Lys | Met | Ile | Trp | Leu | Phe | Tyr | Phe | Ser |
| 145 | | | | 150 | | | | | 155 | | | | | 160 |

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 23
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 23

```
atggctgccg ctccctctgt gcgaaccttt acccgagccg aggttctgaa cgctgaggct      60
ctgaacgagg gcaagaagga cgctgaggct cccttcctga tgatcatcga caacaaggtg     120
tacgacgtcc gagagttcgt ccctgaccat cctggaggct ccgtgattct cacccacgtt     180
ggcaaggacg gcaccgacgt cttttgacacc tttcatcccg aggctgcttg ggagactctc     240
gccaacttct acgttggaga cattgacgag tccgaccgag acatcaagaa cgatgacttt     300
gccgctgagg tccgaaagct gcgaacccctg ttccagtctc tcggctacta cgactccttct     360
aaggcctact acgccttcaa ggtctccttc aacctctgca tctggggact gtccaccgtc     420
attgtggcca gtggggtca gacctccacc ctcgccaacg tgctctctgc tgccctgctc     480
ggcctgttct ggcagcagtg cggatggctg gctcacgact tctgcacca ccaggtcttc     540
caggaccgat tctggggtga ctcttcgga gccttcctgg aggtgtctg ccagggcttc     600
tcctcttcct ggtggaagga caagcacaac actcaccatg ccgctcccaa cgtgcatggc     660
gaggatcctg acattgacac ccaccctctc ctgacctggt ccgagcacgc tctggagatg     720
ttctccgacg tccccgatga ggagctgacc cgaatgtggt ctcgattcat ggtcctgaac     780
cagacctggt tctacttccc cattctctcc ttcgctcgac tgtcttggtg cctccagtcc     840
attctctttg tgctgcccaa cggtcaggct cacaagcct ccggagctcg agtgcccatc     900
tccctggtcg agcagctgtc cctcgccatg cactggacct ggtacctcgc taccatgttc     960
ctgttcatca aggatcctgt caacatgctc gtgtacttcc tggtgtctca ggctgtgtgc    1020
ggaaacctgc tcgccatcgt gttctccctc aaccacaacg gtatgcctgt gatctccaag    1080
```

-continued

```
gaggaggctg tcgacatgga tttctttacc aagcagatca tcactggtcg agatgtccat   1140
cctggactgt tcgccaactg gttcaccggt ggcctgaact accagatcga gcatcacctg   1200
ttcccttcca tgcctcgaca caacttctcc aagatccagc ctgccgtcga gaccctgtgc   1260
aagaagtaca acgtccgata ccacaccact ggtatgatcg agggaactgc cgaggtcttc   1320
tcccgactga acgaggtctc caaggccacc tccaagatgg gcaaggctca gtaa         1374
```

<210> SEQ ID NO 24
<211> LENGTH: 457
<212> TYPE: PRT
<213> ORGANISM: Mortierella alpina AF465281

<400> SEQUENCE: 24

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320
```

```
Leu Phe Ile Lys Asp Pro Val Asn Met Leu Val Tyr Phe Leu Val Ser
            325                 330                 335

Gln Ala Val Cys Gly Asn Leu Leu Ala Ile Val Phe Ser Leu Asn His
            340                 345                 350

Asn Gly Met Pro Val Ile Ser Lys Glu Ala Val Asp Met Asp Phe
            355                 360                 365

Phe Thr Lys Gln Ile Ile Thr Gly Arg Asp Val His Pro Gly Leu Phe
370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
            435                 440                 445

Ala Thr Ser Lys Met Gly Lys Ala Gln
450                 455

<210> SEQ ID NO 25
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 25
taaacagtgt acgcagtact atagaggaac aattgccccg gagaagacgg ccaggccgcc      60
tagatgacaa attcaacaac tcacagctga cttttctgcca ttgccactag gggggggcctt    120 tttatatggc caagccaagc tctccacgtc ggttgggctg cacccaacaa taaatgggta    180
gggttgcacc aacaaaggga tgggatgggg ggtagaagat acgaggataa cggggctcaa    240
tggcacaaat aagaacgaat actgccatta agactcgtga tccagcgact gacaccattg    300
catcatctaa gggcctcaaa actacctcgg aactgctgcg ctgatctgga caccacagag    360
gttccgagca ctttaggttg caccaaatgt cccaccaggt gcaggcagaa aacgctggaa    420
cagcgtgtac agtttgtctt aacaaaaagt gagggcgctg aggtcgagca gggtggtgtg    480
acttgttata gcctttagag ctgcgaaagc gcgtatggat ttggctcatc aggccagatt    540
gagggtctgt ggacacatgt catgttagtg tacttcaatc gcccctgga tatagccccg    600 acaataggcc gtggcctcat tttttgcct ccgcacatt tccattgctc ggtacccaca    660
ccttgcttct cctgcacttg ccaaccttaa tactggttta cattgaccaa catcttacaa    720 gcgggggct tgtctagggt atatataaac agtggctctc ccaatcggtt gccagtctct    780
tttttccttt ctttccccac agattcgaaa tctaaactac acatcacaca atgcctgtta    840
ctgacgtcct taagcgaaag tccggtgtca tcgtcggcga cgatgtccga gccgtgagta    900
tccacgacaa gatcagtgtc gagacgacgc gttttgtgta atgacacaat ccgaaagtcg    960
ctagcaacac acactctcta cacaaactaa cccagctctc c                        1001

<210> SEQ ID NO 26
<211> LENGTH: 1434
<212> TYPE: DNA
<213> ORGANISM: Fusarium monoliforme
<220> FEATURE:
<221> NAME/KEY: misc_feature
```

-continued

<223> OTHER INFORMATION: delta-12 desaturase

<400> SEQUENCE: 26

```
atggcgtcca cttcggctct gcccaagcag aaccctgcgc ttagacgcac cgtcacctca    60
actactgtga cggattctga gtctgccgcc gtctctcctt cagactctcc ccgccactcg   120
gcctcttcca catcgctctc gtccatgtcc gaggttgata tcgccaagcc caagtccgag   180
tatggtgtca tgctcgacac ctacggcaac cagttcgagg ttcccgactt taccatcaag   240
gacatctaca atgccatccc taagcactgc ttcaagcgct ccgctctcaa gggatacggt   300
tatatcctcc gcgacattgt cctcctgact accactttca gcatctggta caactttgtg   360
accccccgaat atatcccctc caccccccgcc cgcgctggtc tgtgggccgt gtacaccgtt   420
cttcagggtc ttttcggtac tggtctctgg gttattgccc atgagtgcgg tcacggtgct   480
ttctccgatt ctcgcatcat caacgacatt actggctggg ttcttcactc ttccctcctt   540
gtcccctact tcagctggca aatctcccac cgaaagcacc acaaggccac tggcaacatg   600
gagcgtgaca tggtcttcgt tccccgaacc cgcgagcagc aggctactcg tctcggaaag   660
atgacccacg agtcgctcca tcttactgag gagaccccccg ctttcactct tctcatgctc   720
gtccttcagc agctcgttgg ctggcccaac tacctcatca ccaatgttac cggccacaac   780
taccacgagc gccagcgtga gggtcgcggc aagggcaagc ataacggcct cggcggtggt   840
gttaaccact cgatccccg cagccctctg tacgagaaca gtgacgctaa gctcatcgtc   900
ctcagcgata ttggtatcgg tctgatggcc actgctctgt acttcctcgt tcagaagttc   960
ggtttctaca acatggccat ctggtacttt gttccctacc tctgggttaa ccactggctc  1020
gttgccatca ccttcctcca gcacaccgac cctaccccttc cccactacac caacgacgag  1080
tggaacttcg tccgtggtgc cgctgctacc attgaccgtg agatgggctt catcggccgc  1140
caccttctcc acggcatcat cgagactcat gtcctccacc actacgtcag cagcatcccc  1200
ttctacaacg cggacgaggc caccgaggcc attaagccca tcatgggcaa gcactaccgg  1260
gctgatgtcc aggatggtcc tcgtggcttc atccgcgcca tgtaccgcag tgcgcgtatg  1320
tgccagtggg ttgagcccag cgctggtgcc gagggtgctg gtaagggtgt tctgttcttc  1380
cgcaaccgca caacgtggg cacccccccc gctgttatca agcccgttgc ttaa         1434
```

<210> SEQ ID NO 27
<211> LENGTH: 477
<212> TYPE: PRT
<213> ORGANISM: Fusarium monoliforme

<400> SEQUENCE: 27

```
Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
```

```
            100                 105                 110
Phe Ser Ile Trp Tyr Asn Phe Val Thr Pro Glu Tyr Ile Pro Ser Thr
            115                 120                 125

Pro Ala Arg Ala Gly Leu Trp Ala Val Tyr Thr Val Leu Gln Gly Leu
130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
            195                 200                 205

Arg Thr Arg Glu Gln Gln Ala Thr Arg Leu Gly Lys Met Thr His Glu
210                 215                 220

Leu Ala His Leu Thr Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
            275                 280                 285

Pro Leu Tyr Glu Asn Ser Asp Ala Lys Leu Ile Val Leu Ser Asp Ile
            290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Pro Tyr Leu Trp Val
                325                 330                 335

Asn His Trp Leu Val Ala Ile Thr Phe Leu Gln His Thr Asp Pro Thr
                340                 345                 350

Leu Pro His Tyr Thr Asn Asp Glu Trp Asn Phe Val Arg Gly Ala Ala
            355                 360                 365

Ala Thr Ile Asp Arg Glu Met Gly Phe Ile Gly Arg His Leu Leu His
370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
            435                 440                 445

Gly Ala Glu Gly Ala Gly Lys Gly Val Leu Phe Phe Arg Asn Arg Asn
            450                 455                 460

Asn Val Gly Thr Pro Pro Ala Val Ile Lys Pro Val Ala
465                 470                 475

<210> SEQ ID NO 28
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)
```

```
<400> SEQUENCE: 28
atggccaact cctctgtctg ggacgacgtg gtcggacgag tcgagaccgg tgtcgaccag      60
tggatggacg gagctaagcc ctacgctctg accgacggtc tgcccatgat ggacgtctcc     120
accatgctcg ccttcgaggt cggctacatg gccatgctgc tcttcggcat tcccatcatg     180
aagcagatgg agaagccctt cgagctgaag accatcaagc tgctccacaa cctgttcctc     240
ttcggactgt ccctctacat gtgcgtcgag accatccgac aggctatcct gggtggctac     300
aaggtcttcg gcaacgacat ggagaagggc aacgagtccc acgctcaggg catgtcccga     360
atcgtctacg tgttctacgt ctccaaggcc tacgagttcc tggacaccgc tatcatgatc     420
ctgtgcaaga agttcaacca ggtctccttc ctgcacgtgt accacgctca ccatcttc       480
gccatctggt gggctattgc caagtacgct cctggtggcg acgcctactt ctccgtcatc     540
ctcaactcct cgtccacac cgtcatgtac gcctactact tcttttcctc tcagggcttc      600
ggcttcgtca agcccatcaa gccctacatc accactctgc agatgaccca gttcatggct     660
atgctggtgc agtccctgta cgactacctc ttcccctgcg actaccctca ggctctggtc     720
cagctgctcg gcgtgtacat gatcaccctg ctcgctctgt tcggcaactt ctttgtccag     780
tcctacctga agaagcccaa gaagtccaag accaactaa                            819

<210> SEQ ID NO 29
<211> LENGTH: 272
<212> TYPE: PRT
<213> ORGANISM: Thraustochytrium aureum

<400> SEQUENCE: 29

Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
```

```
                     210                 215                 220
Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
                260                 265                 270

<210> SEQ ID NO 30
<211> LENGTH: 13006
<212> TYPE: DNA
<213> ORGANISM: Artificial Sequence
<220> FEATURE:
<223> OTHER INFORMATION: Plasmid pDMW236

<400> SEQUENCE: 30
aaacagtgta cgcagtacta tagaggaaca attgccccgg agaagacggc caggccgcct      60
agatgacaaa ttcaacaact cacagctgac tttctgccat tgccactagg ggggggcctt     120
tttatatggc caagccaagc tctccacgtc ggttgggctg cacccaacaa taaatgggta     180
gggttgcacc aacaaaggga tgggatgggg ggtagaagat acgaggataa cggggctcaa     240
tggcacaaat aagaacgaat actgccatta agactcgtga tccagcgact gacaccattg     300
catcatctaa gggcctcaaa actacctcgg aactgctgcg ctgatctgga caccacagag     360
gttccgagca ctttaggttg caccaaatgt cccaccaggt gcaggcagaa aacgctggaa     420
cagcgtgtac agtttgtctt aacaaaaagt gagggcgctg aggtcgagca gggtggtgtg     480
acttgttata gcctttagag ctgcgaaagc gcgtatggat ttggctcatc aggccagatt     540
gagggtctgt ggacacatgt catgttagtg tacttcaatc gcccctgga tatagccccg      600
acaataggcc gtggcctcat ttttttgcct tccgcacatt tccattgctc ggtacccaca     660
ccttgcttct cctgcacttg ccaaccttaa tactggttta cattgaccaa catcttacaa     720
gcggggggct tgtctagggt atatataaac agtggctctc ccaatcggtt gccagtctct     780
tttttccttt ctttcccccac agattcgaaa tctaaactac acatcacaca atgcctgtta     840
ctgacgtcct taagcgaaag tccggtgtca tcgtcggcga cgatgtccga gccgtgagta     900
tccacgacaa gatcagtgtc gagacgacgc gttttgtgta atgacacaat ccgaaagtcg     960
ctagcaacac acactctcta cacaaactaa cccagctctc catggctgag ataagacca    1020
aggtcgagtt ccctaccctg actgagctga agcactctat ccctaacgct tgctttgagt    1080
ccaacctcgg actctcgctc tactacactg cccgagcgat cttcaacgca tctgcctctg    1140
ctgctctgct ctacgctgcc cgatctactc ccttcattgc cgataacgtt ctgctccacg    1200
ctctggtttg cgccacctac atctacgtgc agggtgtcat cttctggggt ttctttaccg    1260
tcggtcacga ctgtggtcac tctgccttct cccgatacca ctccgtcaac ttcatcattg    1320
gctgcatcat gcactctgcc attctgactc ccttcgagtc ctggcgagtg acccaccgac    1380
accatcacaa gaacactggc aacattgata aggacgagat cttctaccct catcggtccg    1440
tcaaggacct ccaggacgtg cgacaatggg tctacaccct cggaggtgct tggtttgtct    1500
acctgaaggt cggatatgct cctcgaacca tgtcccactt tgaccctgg accctctcc     1560
tgcttcgacg agcctccgct gtcatcgtgt ccctcggagt ctgggctgcc ttcttcgctg    1620
cctacgccta cctcacatac tcgctcggct ttgccgtcat gggcctctac tactatgctc    1680
ctctctttgt ctttgcttcg ttcctcgtca ttactacctt cttgcatcac aacgacgaag    1740
```

```
ctactccctg gtacggtgac tcggagtgga cctacgtcaa gggcaacctg agctccgtcg    1800
accgatcgta cggagctttc gtggacaacc tgtctcacca cattggcacc caccaggtcc    1860
atcacttgtt ccctatcatt ccccactaca agctcaacga agccaccaag cactttgctg    1920
ccgcttaccc tcacctcgtg agacgtaacg acgagcccat cattactgcc ttcttcaaga    1980
ccgctcacct ctttgtcaac tacgagctg tgcccgagac tgctcagatt ttcaccctca    2040
aagagtctgc cgctgcagcc aaggccaaga gcgactaagc ggccgcattg atgattggaa    2100
acacacacat gggttatatc taggtgagag ttagttggac agttatatat aaatcagct    2160 atgccaacgg taacttcatt catgtcaacg aggaaccagt gactgcaagt aatatagaat    2220
ttgaccacct tgccattctc ttgcactcct ttactatatc tcatttattt cttatataca    2280
aatcacttct tcttcccagc atcgagctcg aaacctcat gagcaataac atcgtggatc     2340
tcgtcaatag agggctttt ggactccttg ctgttggcca ccttgtcctt gctgtctggc     2400
tcattctgtt tcaacgcctt ttaattaacg gagtaggtct cggtgtcgga agcgacgcca    2460
gatccgtcat cctcctttcg ctctccaaag tagatacctc cgacgagctc tcggacaatg    2520
atgaagtcgg tgccctcaac gtttcggatg ggggagagat cggcgagctt gggcgacagc    2580
agctggcagg gtcgcaggtt ggcgtacagg ttcaggtcct ttcgcagctt gaggagaccc    2640
tgctcgggtc gcacgtcggt tcgtccgtcg ggagtggtcc atacggtgtt ggcagcgcct    2700
ccgacagcac cgagcataat agagtcagcc tttcggcaga tgtcgagagt agcgtcggtg    2760
atgggctcgc cctccttctc aatgcagct cctccaatga gtcggtcctc aaacacaaac     2820
tcggtgccgg aggcctcagc aacagacttg agcaccttga cggcctcggc aatcacctcg    2880
gggccacaga gtcgccgcc gagaagaaca atcttcttgg agtcagtctt ggtcttctta     2940
gtttcgggtt ccattgtgga tgtgtgtggt tgtatgtgtg atgtggtgtg tggagtgaaa    3000
atctgtggct ggcaaacgct cttgtatata tacgcacttt tgcccgtgct atgtggaaga    3060
ctaaacctcc gaagattgtg actcaggtag tgcggtatcg gctagggacc caaaccttgt    3120
cgatgccgat agcatgcgac gtcgggccca attcgcccta tagtgagtcg tattacaatt    3180
cactggccgt cgttttacaa cgtcgtgact gggaaaaccc tggcgttacc caacttaatc    3240
gccttgcagc acatcccct ttcgccagct ggcgtaatag cgaagaggcc cgcaccgatc     3300
gcccttccca acagttgcgc agcctgaatg gcgaatggac gcgccctgta gcggcgcatt    3360
aagcgcggcg ggtgtggtgg ttacgcgcag cgtgaccgct acacttgcca gcgccctagc    3420
gcccgctcct ttcgctttct tcccttcctt tctcgccacg ttcgccggct ttccccgtca    3480
agctctaaat cggggctcc ctttaggggtt ccgatttagt gctttacggg acctcgaccc    3540
caaaaaactt gattagggtg atggttcacg tagtgggcca tcgccctgat agacggtttt    3600
tcgccctttg acgttggagt ccacgttctt taatagtgga ctcttgttcc aaactggaac    3660
aacactcaac cctatctcgg tctattcttt tgatttataa gggattttgc cgatttcggc    3720
ctattggtta aaaatgagc tgatttaaca aaaatttaac gcgaatttta acaaaatatt     3780
aacgcttaca atttcctgat gcggtatttt ctccttacgc atctgtgcgg tatttcacac    3840
cgcatcaggt ggcacttttc ggggaaatgt gcgcggaacc cctatttgtt tatttttcta    3900
aatacattca aatatgtatc cgctcatgag acaataaccc tgataaatgc ttcaataata    3960
ttgaaaaagg aagagtatga gtattcaaca tttccgtgtc gcccttattc ccttttttgc    4020
ggcattttgc cttcctgttt ttgctcaccc agaaacgctg gtgaaagtaa aagatgctga    4080
agatcagttg ggtgcacgag tgggttacat cgaactggat ctcaacagcg gtaagatcct    4140
```

```
tgagagtttt cgccccgaag aacgttttcc aatgatgagc acttttaaag ttctgctatg    4200
tggcgcggta ttatcccgta ttgacgccgg gcaagagcaa ctcggtcgcc gcatacacta    4260
ttctcagaat gacttggttg agtactcacc agtcacagaa aagcatctta cggatggcat    4320
gacagtaaga gaattatgca gtgctgccat aaccatgagt gataacactg cggccaactt    4380
acttctgaca acgatcggag gaccgaagga gctaaccgct tttttgcaca acatggggga    4440
tcatgtaact cgccttgatc gttgggaacc ggagctgaat gaagccatac caaacgacga    4500
gcgtgacacc acgatgcctg tagcaatggc aacaacgttg cgcaaactat taactggcga    4560
actacttact ctagcttccc ggcaacaatt aatagactgg atggaggcgg ataaagttgc    4620
aggaccactt ctgcgctcgg cccttccggc tggctggttt attgctgata atctggagc    4680 cggtgagcgt gggtctcgcg gtatcattgc agcactgggg ccagatggta gccctcccg    4740 tatcgtagtt atctcacgac cggggagtca ggcaactatg gatgaacgaa atagacagat    4800
cgctgagata ggtgcctcac tgattaagca ttggtaactg tcagaccaag tttactcata    4860
tatactttag attgatttaa aacttcattt ttaatttaaa aggatctagg tgaagatcct    4920
ttttgataat ctcatgacca aaatccctta acgtgagttt cgttccact gagcgtcaga    4980 ccccgtagaa aagatcaaag gatcttcttg agatcctttt tttctgcgcg taatctgctg    5040
cttgcaaaca aaaaaaccac cgctaccagc ggtggtttgt ttgccggatc aagagctacc    5100
aactcttttt ccgaaggtaa ctggcttcag cagagcgcag ataccaaata ctgttcttct    5160
agtgtagccg tagttaggcc accacttcaa gaactctgta gcaccgccta catacctcgc    5220
tctgctaatc ctgttaccag tggctgctgc cagtggcgat aagtcgtgtc ttaccgggtt    5280
ggactcaaga cgatagttac cggataaggc gcagcggtcg ggctgaacgg ggggttcgtg    5340
cacacagccc agcttggagc gaacgaccta caccgaactg agatacctac agcgtgagct    5400
atgagaaagc gccacgcttc ccgaagggag aaaggcggac aggtatccgg taagcggcag    5460
ggtcggaaca ggagagcgca cgagggagct tccaggggga aacgcctggt atctttatag    5520
tcctgtcggg tttcgccacc tctgacttga gcgtcgattt ttgtgatgct cgtcaggggg    5580
gcggagccta tggaaaaacg ccagcaacgc ggccttttta cggttcctgg ccttttgctg    5640
gccttttgct cacatgttct ttcctgcgtt atcccctgat tctgtggata accgtattac    5700
cgcctttgag tgagctgata ccgctcgccg cagccgaacg accgagcgca gcgagtcagt    5760
gagcgaggaa gcggaagagc gcccaatacg caaaccgcct ctccccgcgc gttggccgat    5820
tcattaatgc agctggcgcg cccactgagc tcgtctaacg gacttgatat acaaccaatt    5880
aaaacaaatg aaaagaaata cagttctttg tatcatttgt aacaattacc ctgtacaaac    5940
taaggtattg aaatcccaca atattcccaa gtccaccccc tttccaaatt gtcatgccta    6000
caactcatat accaagcact aacctaccaa acaccactaa aacccacaa aatatatctt    6060 accgaatata cagtaacaag ctaccaccac actcgttggg tgcagtcgcc agcttaaaga    6120
tatctatcca catcagccac aactcccttc ctttaataaa ccgactacac ccttggctat    6180
tgaggttatg agtgaatata ctgtagacaa gacactttca agaagactgt ttccaaaacg    6240
taccactgtc ctcccactaca aacacaccca atctgcttct tctagtcaag gttgctacac    6300
cggtaaatta taaatcatca tttcattagc agggcagggc ccttttttata gagtcttata    6360 cactagcgga ccctgccggt agaccaaccc gcaggcgcgt cagtttgctc cttccatcaa    6420
tgcgtcgtag aaacgactta ctccttcttg agcagctcct tgaccttgtt ggcaacaagt    6480
```

```
ctccgacctc ggaggtggag gaagagcctc cgatatcggc ggtagtgata ccagcctcga    6540
cggactcctt gacggcagcc tcaacagcgt caccggcggg cttcatgtta agagagaact    6600
tgagcatcat ggcggcagac agaatggtgg cgtacgcaac taacatgaat gaatacgata    6660
tacatcaaag actatgatac gcagtattgc acactgtacg agtaagagca ctagccactg    6720
cactcaagtg aaaccgttgc ccgggtacga gtatgagtat gtacagtatg tttagtattg    6780
tacttggaca gtgcttgtat cgtacattct caagtgtcaa acataaatat ccgttgctat    6840
atcctcgcac caccacgtag ctcgctatat ccctgtgttg aatccatcca tcttggattg    6900
ccaattgtgc acacagaacc gggcactcac ttccccatcc acacttgcgg ccgcttagct    6960
gcctactctt ccttgggacg gagtccaaga acacgcaagt gctccaaatg tgaagcaaat    7020
gcttgccaaa acgtatcctt gacaaggtat ggaaccttgt actcgctgca ggtgttcttg    7080
atgatggcca gaatatcggg ataatggtgc tgcgacacgt ggggaacag atggtgcaca    7140
gcctggtagt tcaagctgcc agtgatgctg gtccagaggt gcgaatcgtg tgcgtaatcc    7200
tgcgtagtct cgacctgcat agctgcccag tccttttgga tgatcccgtt ctcgtcaggc    7260
aacgccact gaacttcctc aacaacgtgg ttcgcctgga aggtcagcgc cagccagtaa    7320
gacgacacca tgtccgcgac cgtgaacaag agcagcacct tgcccagggg cagatactgc    7380
aggggaacaa tcaggcgata ccagacaaag aaagccttgc cgcccagaa catcacagtg    7440
tgccatgtcg agatgggatt gacacgaata gcgtcattgg tcttgacaaa gtacaaaatg    7500
ttgatgtcct gaatgcgcac cttgaacgcc agcagtccgt acaggaaagg aacaaacatg    7560
tgctggttga tgtggttgac aaaccacttt tggttgggct tgatacgacg aacatcgggc    7620
tcagacgtcg acacgtcggg atctgctcca gcaatgttgg tgtaggggtg atggccgagc    7680
atatgttggt acatccacac caggtacgat gctccgttga aaaagtcgtg cgtggctccc    7740
agaatcttcc agacagtggg gttgtgggtc actgaaaagt gagacgcatc atgaagaggg    7800
ttgagtccga cttgtgcgca cgcaaatccc atgatgattg caaacaccac ctgaagccat    7860
gtgcgttcga caacgaaagg cacaaagagc tgcgcgtagt aggaagcgat caaggatcca    7920
aagataagag cgtatcgtcc ccagatctct ggtctattct tgggatcaat gttccgatcc    7980
gtaaagtagc cctcgactct cgtcttgatg gttttgtgga acaccgttgg ctccgggaag    8040
atgggcagct cattcgagac cagtgtaccg acatagtact tcttcataat ggcatctgca    8100
gccccaaacg cgtgatacat ctcaaagacc ggagtaacat ctcggccagc tccgagcagg    8160
agagtgtcca ctccaccagg atggcggctc aagaactttg tgcatcgta caccctgccg    8220
cggatggcca agagtaggtc gtccttggtg ttatgggccg ccagctcttc ccaggtgaag    8280
gtttttcctt ggtccgttcc catggagagc tgggttagtt tgtgtagaga gtgtgtgttg    8340
ctagcgactt tcggattgtg tcattacaca aaacgcgtcg tctcgacact gatcttgtcg    8400
tggatactca cggctcggac atcgtcgccg acgatgacac cggactttcg cttaaggacg    8460
tcagtaacag gcattgtgtg atgtgtagtt tagatttcga atctgtgggg aagaaagga    8520
aaaagagac tggcaaccga ttgggagagc cactgtttat atatacccta gacaagcccc    8580
ccgcttgtaa gatgttggtc aatgtaaacc agtattaagg ttggcaagtg caggagaagc    8640
aaggtgtggg taccgagcaa tggaaatgtg cggaaggcaa aaaatgagg ccacggccta    8700
ttgtcggggc tatatccagg gggcgattga agtacactaa catgacatgt gtccacagac    8760
cctcaatctg gcctgatgag ccaaatccat acgcgctttc gcagctctaa aggctataac    8820
aagtcacacc accctgctcg acctcagcgc cctcacttt tgttaagaca aactgtacac    8880
```

-continued

```
gctgttccag cgttttctgc ctgcacctgg tgggacattt ggtgcaacct aaagtgctcg    8940
gaacctctgt ggtgtccaga tcagcgcagc agttccgagg tagttttgag gcccttagat    9000
gatgcaatgg tgtcagtcgc tggatcacga gtcttaatgg cagtattcgt tcttatttgt    9060
gccattgagc cccgttatcc tcgtatcttc tacccccat cccatccctt tgttggtgca     9120
accctaccca tttattgttg ggtgcagccc aaccgacgtg gagagcttgg cttggccata    9180
taaaaaggcc ccccctagt ggcaatggca gaaagtcagc tgtgagttgt tgaatttgtc     9240
atctaggcgg cctggccgtc ttctccgggg caatttaaat tccttcactt caagttcatt    9300
cttcatctgc ttctgtttta ctttgacagg caaatgaaga catggtacga cttgatggag    9360
gccaagaacg ccatttcacc ccgagacacc gaagtgcctg aaatcctggc tgcccccatt    9420
gataacatcg gaaactacgg tattccggaa agtgtatata gaacctttcc ccagcttgtg    9480
tctgtggata tggatggtgt aatccccttt gagtactcgt cttggcttct ctccgagcag    9540
tatgaggctc tctaatctag cgcatttaat atctcaatgt atttatatat ttatcttctc    9600
atgcggccgc ttagctgcct actcttcctt gggacggagt ccaagaacac gcaagtgctc    9660
caaatgtgaa gcaaatgctt gccaaaacgt atccttgaca aggtatggaa ccttgtactc    9720
gctgcaggtg ttcttgatga tggccagaat atcgggataa tggtgctgcg acacgttggg    9780
gaacagatgg tgcacagcct ggtagttcaa gctgccagtg atgctggtcc agaggtgcga    9840
atcgtgtgcg taatcctgcg tagtctcgac ctgcatagct gcccagtcct tttggatgat    9900
cccgttctcg tcaggcaacg gccactgaac ttcctcaaca acgtggttcg cctggaaggt    9960
cagcgccagc cagtaagacg acaccatgtc cgcgaccgtg aacaagagca gcaccttgcc    10020
caggggcaga tactgcaggg gaacaatcag gcgataccag acaaagaaag ccttgccgcc    10080
ccagaacatc acagtgtgcc atgtcgagat gggattgaca cgaatagcgt cattggtctt    10140
gacaaagtac aaaatgttga tgtcctgaat gcgcaccttg aacgccagca gtccgtacag    10200
gaaaggaaca acatgtgct ggttgatgtg gttgacaaac cacttttggt tgggcttgat     10260
acgacgaaca tcgggctcag acgtcgacac gtcgggatct gctccagcaa tgttggtgta    10320
ggggtgatgg ccgagcatat gttggtacat ccacaccagg tacgatgctc cgttgaaaaa    10380
gtcgtgcgtg gctcccagaa tcttccgac agtgggttg tgggtcactg aaaagtgaga      10440
cgcatcatga agagggttga gtccgacttg tgcgcacgca atcccatga tgattgcaaa     10500 caccacctga agccatgtgc gttcgacaac gaaaggcaca aagagctgcg cgtagtagga    10560
agcgatcaag gatccaaaga taagagcgta tcgtcccag atctctggtc tattcttggg    10620
atcaatgttc cgatccgtaa agtagccctc gactctcgtc ttgatggttt tgtgaacac     10680 cgttggctcc gggaagatgg gcagctcatt cgagaccagt gtaccgacat agtacttctt    10740
cataatggca tctgcagccc caaacgcgtg atacatctca aagaccggag taacatctcg    10800
gccagctccg agcaggagag tgtccactcc accaggatgg cggctcaaga actttgtgac    10860
atcgtacacc ctgccgcgga tggccaagag taggtcgtcc ttggtgttat gggccgccag    10920
ctcttcccag gtgaaggttt ttccttggtc cgttcccatg gtgaatgatt cttatactca    10980
gaaggaaatg cttaacgatt tcgggtgtga gttgacaagg agagagagaa aagaaggaga    11040 aggtaattc ggggacggtg gtcttttata ccctggcta aagtcccaac cacaaagcaa       11100
aaaaattttc agtagtctat tttgcgtccg gcatgggtta cccggatggc cagacaaaga    11160
aactagtaca aagtctgaac aagcgtagat tccagactgc agtaccctac gcccttaacg    11220
```

```
gcaagtgtgg gaaccggggg aggtttgata tgtggggtga aggggctct cgccggggtt    11280 gggcccgcta ctgggtcaat ttggggtcaa ttggggcaat tggggctgtt ttttgggaca    11340
caaatacgcc gccaacccgg tctctcctga tcgatgggct gcaggaattc tacaatacgt    11400
gagtcagaag ggctgacggt ggtggttccc aaggaaaagg tcgacgagta tctgtctgac    11460
tcgtcattgc cgcctttgga gtacgactcc aactatgagt gtgcttggat cactttgacg    11520
atacattctt cgttggaggc tgtgggtctg acagctgcgt tttcggcgcg gttggccgac    11580
aacaatatca gctgcaacgt cattgctggc tttcatcatg atcacatttt tgtcggcaaa    11640
ggcgacgccc agagagccat tgacgttctt tctaatttgg accgatagcc gtatagtcca    11700
gtctatctat aagttcaact aactcgtaac tattaccata acatatactt cactgcccca    11760
gataaggttc cgataaaaag ttctgcagac taaatttatt tcagtctcct cttcaccacc    11820
aaaatgccct cctacgaagc tcgagctaac gtccacaagt ccgcctttgc cgctcgagtg    11880
ctcaagctcg tggcagccaa gaaaaccaac ctgtgtgctt ctctggatgt taccaccacc    11940
aaggagctca ttgagcttgc cgataaggtc ggaccttatg tgtgcatgat caaaacccat    12000
atcgacatca ttgacgactt cacctacgcc ggcactgtgc tccccctcaa ggaacttgct    12060
cttaagcacg gtttcttcct gttcgaggac agaaagttcg cagatattgg caacactgtc    12120
aagcaccagt accggtgtca ccgaatcgcc gagtggtccg atatcaccaa cgcccacggt    12180
gtacccggaa ccggaatcat tgctggcctg cgagctggtg ccgaggaaac tgtctctgaa    12240
cagaagaagg aggacgtctc tgactacgag aactcccagt acaaggagtt cctagtcccc    12300
tctcccaacg agaagctggc cagaggtctg ctcatgctgg ccgagctgtc ttgcaagggc    12360
tctctggcca ctggcgagta ctccaagcag accattgagc ttgcccgatc cgaccccgag    12420
tttgtggttg gcttcattgc ccagaaccga cctaagggcg actctgagga ctggcttatt    12480
ctgacccccg gggtgggtct tgacgacaag ggagacgctc tcggacagca gtaccgaact    12540
gttgaggatg tcatgtctac cggaacggat atcataattg tcggccgagg tctgtacggc    12600
cagaaccgag atcctattga ggaggccaag cgataccaga aggctggctg ggaggcttac    12660
cagaagatta actgttagag gttagactat ggatatgtaa tttaactgtg tatatagaga    12720
gcgtgcaagt atggagcgct tgttcagctt gtatgatggt cagacgacct gtctgatcga    12780
gtatgtatga tactgcacaa cctgtgtatc cgcatgatct gtccaatggg gcatgttgtt    12840
gtgtttctcg atacggagat gctgggtaca gtgctaatac gttgaactac ttatacttat    12900
atgaggctcg aagaaagctg acttgtgtat gacttattct caactacatc cccagtcaca    12960
ataccaccac tgcactacca ctacaccaga tctgcgtaca ctgttt                    13006
```

<210> SEQ ID NO 31
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 31

```
aagcagtggt atcaacgcag agtggccatt acggccggg                              39
```

<210> SEQ ID NO 32
<211> LENGTH: 59
<212> TYPE: DNA
<213> ORGANISM: Artificial Sequence
<220> FEATURE:
<223> OTHER INFORMATION: CDSIII/3'PCR primer

```
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 32
attctagagg ccgaggcggc cgacatgttt tttttttttt tttttttttt tttttttvn      59

<210> SEQ ID NO 33
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 33
aagcagtggt atcaacgcag agt                                            23

<210> SEQ ID NO 34
<211> LENGTH: 86
<212> TYPE: DNA
<213> ORGANISM: Artificial Sequence
<220> FEATURE:
<223> OTHER INFORMATION: Primer YL421

<400> SEQUENCE: 34
tttccatggc tacctctgac ccttccgtcc gagctttcac acgatctgaa gtcttgcacg    60
ccgatgcctt gaacgagggc aaaaag                                         86

<210> SEQ ID NO 35
<211> LENGTH: 81
<212> TYPE: DNA
<213> ORGANISM: Artificial Sequence
<220> FEATURE:
<223> OTHER INFORMATION: Primer YL422

<400> SEQUENCE: 35
tttgcggccg ctcaagcaga cttgccgagc ttggaggcag cctgagagac ctcgttcagt    60
cgcgaaaaga cctctgcggt g                                              81

<210> SEQ ID NO 36
<211> LENGTH: 1377
<212> TYPE: DNA
<213> ORGANISM: Artificial Sequence
<220> FEATURE:
<223> OTHER INFORMATION: Delta 6B desaturase in pT-6BC

<400> SEQUENCE: 36
atggctacct ctgacccttc cgtccgagct ttcacacgat ctgaagtctt gcacgccgat    60
gccttgaacg agggcaaaaa gaatgctgaa gccccgttcc tcatgatcat tgacaacaaa   120
gtctacgatg tgcgcgagtt tgtccccgac catcctggcg gtagtgtcat tttgacccac   180
gtaggcaagg acggcacgga cgtcttcgag accttccatc ccgaggccgc gtgggaaacg   240
ctcgccaact tttatgtcgg cgacattgca gaatccgatc gtgcgattga gaatgacgag   300
tttgcagccg aagtccgcaa gctgcgtact tgttccagt ctctgggata ttacaactca   360
tccaaaacct actacgcctt caaggtctca ttcaacctct gcatctgggg cctgtcggcg   420
tttatggttg ccaagtgggg ccagacctcg accctcgcca acgtggtgtc tgcgtcgctt   480
```

```
ctgggtgtct tttggcaaca gtgtggttgg ctcgcccatg acttcttaca ccaccaggtc    540
tttcacgatc ggttctgggg tgatttgttt ggtgccttcc tcggcggagt ctgtcagggg    600
ttctcctctt cctggtggaa ggacaaacac aacacccacc acgcggcgcc caatgtccat    660
ggagaggatc ccgatatcga cacgcaccca ctgttgacat ggagcgaaca tgcgctcgag    720
atgttttcgg atgtgcccga tgaggagttg gcccaaatgt ggtcccggtt tatggttgtg    780
aaccagacct ggttttactt tcccattctg tcgttcgccc ggttgtcgtg gtgcattcaa    840
tcgattcttt ttgtgctccc gaacggacag gcacacaagc ctgcgggagc ccgggtcccc    900
atctcgctgg tggagcaatt gtcgctggcg atgcattgga cctggtatct ggcgaccatg    960
ttcttgttta tcaaggatcc tgtcaacata atggtgtatt tcttggtctc gcaagcggtc   1020
tgtggcaacc tgttggcgat tgtgttctct ctgaaccata acggcatgcc tgtgatctct   1080
caggaagaag cggtcgagat ggatttcttt acaaagcaga tcattacggg ccgtgatgtc   1140
cacccaggct ggttcgcaga ctggttcacg ggcggattga actatcaaat tgagcaccac   1200
ctgttcccgt cgatgcctcg ccactatttc tcaaagatcc aaccaacggt cgaatcattg   1260
tgcaaaaagt acggggtccg atatcacacg acggggatga tagatggcac cgcagaggtc   1320
ttttcgcgac tgaacgaggt ctctcaggct gcctccaagc tcggcaagtc tgcttga      1377
```

```
<210> SEQ ID NO 37
<211> LENGTH: 38
<212> TYPE: DNA
<213> ORGANISM: Artificial Sequence
<220> FEATURE:
<223> OTHER INFORMATION: Primer YL475

<400> SEQUENCE: 37
acgcggcgcc caatgtccat ggagaggatc ccgatatc                              38

<210> SEQ ID NO 38
<211> LENGTH: 38
<212> TYPE: DNA
<213> ORGANISM: Artificial Sequence
<220> FEATURE:
<223> OTHER INFORMATION: Primer YL476

<400> SEQUENCE: 38
gatatcggga tcctctccgt ggacattggg cgccgcgt                              38

<210> SEQ ID NO 39
<211> LENGTH: 37
<212> TYPE: DNA
<213> ORGANISM: Artificial Sequence
<220> FEATURE:
<223> OTHER INFORMATION: Primer YL477

<400> SEQUENCE: 39
ctctctgaac cataacggaa tgcctgtgat ctctcag                               37

<210> SEQ ID NO 40
<211> LENGTH: 37
<212> TYPE: DNA
<213> ORGANISM: Artificial Sequence
<220> FEATURE:
<223> OTHER INFORMATION: Primer YL478

<400> SEQUENCE: 40
ctgagagatc acaggcattc cgttatggtt cagagag                               37
```

<210> SEQ ID NO 41
<211> LENGTH: 41
<212> TYPE: DNA
<213> ORGANISM: Artificial Sequence
<220> FEATURE:
<223> OTHER INFORMATION: Primer YL479

<400> SEQUENCE: 41
gttgtcgtgg tgcattcagt ccattctttt tgtgctcccg a                41

<210> SEQ ID NO 42
<211> LENGTH: 41
<212> TYPE: DNA
<213> ORGANISM: Artificial Sequence
<220> FEATURE:
<223> OTHER INFORMATION: Primer YL480

<400> SEQUENCE: 42
tcgggagcac aaaaagaatg gactgaatgc accacgacaa c                41

<210> SEQ ID NO 43
<211> LENGTH: 39
<212> TYPE: DNA
<213> ORGANISM: Artificial Sequence
<220> FEATURE:
<223> OTHER INFORMATION: Primer YL497

<400> SEQUENCE: 43
gccatttaaa tgtagctaac ggtagcaggc gaactactg                   39

<210> SEQ ID NO 44
<211> LENGTH: 34
<212> TYPE: DNA
<213> ORGANISM: Artificial Sequence
<220> FEATURE:
<223> OTHER INFORMATION: Primer YL498

<400> SEQUENCE: 44
tttccatggt tagcgtgtcg tgttttttgtt gtgc                       34

<210> SEQ ID NO 45
<211> LENGTH: 324
<212> TYPE: DNA
<213> ORGANISM: Yarrowia lipolytica (GenBank Accession No. AF054613)

<400> SEQUENCE: 45
gcggccgcaa gtgtggatgg ggaagtgagt gcccggttct gtgtgcacaa ttggcaatcc    60
aagatggatg gattcaacac agggatatag cgagctacgt ggtggtgcga ggatatagca   120
acggatattt atgtttgaca cttgagaatg tacgatacaa gcactgtcca agtacaatac   180
taaacatact gtacatactc atactcgtac ccgggcaacg gtttcacttg agtgcagtgg   240
ctagtgctct tactcgtaca gtgtgcaata ctgcgtatca tagtctttga tgtatatcgt   300
attcattcat gttagttgcg tacg                                          324

<210> SEQ ID NO 46
<211> LENGTH: 32
<212> TYPE: DNA
<213> ORGANISM: Artificial Sequence
<220> FEATURE:
<223> OTHER INFORMATION: Primer YL259

<400> SEQUENCE: 46
tttgcggccg caagtgtgga tggggaagtg ag                          32

<210> SEQ ID NO 47
<211> LENGTH: 30
<212> TYPE: DNA
<213> ORGANISM: Artificial Sequence
<220> FEATURE:
<223> OTHER INFORMATION: Primer YL260

<400> SEQUENCE: 47
tttcgtacga ttgacgcaac taacatgaat                                      30

<210> SEQ ID NO 48
<211> LENGTH: 1936
<212> TYPE: DNA
<213> ORGANISM: Yarrowia lipolytica
<220> FEATURE:
<221> NAME/KEY: misc_feature
<223> OTHER INFORMATION: delta-12 desaturase
<220> FEATURE:
<221> NAME/KEY: CDS
<222> LOCATION: (283)..(1539)

<400> SEQUENCE: 48
cgtagttata tacaagaggt agatgcgtgc tggtgttaga ggggctctca ggattaggag     60
gaaaatttga cattggccct caacatataa cctcgggtgt gcctctgttt accctcagct    120
tttgcttgtc cccaagtcag tcacgccagg ccaaaaaggt tggtggattg acagggagaa    180
aaaaaaaagc ctagtgggtt taaactcgag gtaagacatt gaaatatata ccggtcggca    240
tcctgagtcc ctttctcgta ttccaacaga ccgaccatag aa atg gat tcg acc       294
                                                Met Asp Ser Thr
                                                  1 acg cag acc aac acc ggc acc ggc aag gtg gcc gtg cag ccc ccc acg       342
Thr Gln Thr Asn Thr Gly Thr Gly Lys Val Ala Val Gln Pro Pro Thr
  5                  10                  15                  20 gcc ttc att aag ccc att gag aag gtg tcc gag ccc gtc tac gac acc       390
Ala Phe Ile Lys Pro Ile Glu Lys Val Ser Glu Pro Val Tyr Asp Thr
                 25                  30                  35 ttt ggc aac gag ttc act cct cca gac tac tct atc aag gat att ctg       438
Phe Gly Asn Glu Phe Thr Pro Pro Asp Tyr Ser Ile Lys Asp Ile Leu
             40                  45                  50 gat gcc att ccc cag gag tgc tac aag cgg tcc tac gtt aag tcc tac       486
Asp Ala Ile Pro Gln Glu Cys Tyr Lys Arg Ser Tyr Val Lys Ser Tyr
         55                  60                  65 tcg tac gtg gcc cga gac tgc ttc ttt atc gcc gtt ttt gcc tac atg       534
Ser Tyr Val Ala Arg Asp Cys Phe Phe Ile Ala Val Phe Ala Tyr Met
     70                  75                  80 gcc tac gcg tac ctg cct ctt att ccc tcg gct tcc ggc cga gct gtg       582
Ala Tyr Ala Tyr Leu Pro Leu Ile Pro Ser Ala Ser Gly Arg Ala Val
 85                  90                  95                 100 gcc tgg gcc atg tac tcc att gtc cag ggt ctg ttt ggc acc ggt ctg       630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac       678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc       726
Thr Val Asn Asn Val Thr Gly Trp Val Leu His Ser Ser Met Leu Val
        135                 140                 145 cct tac tac gcc tgg aag ctg acc cac tcc atg cac cac aag tcc act       774
Pro Tyr Tyr Ala Trp Lys Leu Thr His Ser Met His His Lys Ser Thr
    150                 155                 160

| | | |
|---|---|---|
| ggt cac ctc acc cgt gat atg gtg ttt gtg ccc aag gac cga aag gag<br>Gly His Leu Thr Arg Asp Met Val Phe Val Pro Lys Asp Arg Lys Glu<br>165                      170                    175                    180 | 822 |
| ttt atg gag aac cga ggc gcc cat gac tgg tct gag ctt gct gag gac<br>Phe Met Glu Asn Arg Gly Ala His Asp Trp Ser Glu Leu Ala Glu Asp<br>                    185                    190                    195 | 870 |
| gct ccc ctc atg acc ctc tac ggc ctc atc acc cag cag gtg ttt gga<br>Ala Pro Leu Met Thr Leu Tyr Gly Leu Ile Thr Gln Gln Val Phe Gly<br>200                      205                    210 | 918 |
| tgg cct ctg tat ctg ctg tct tac gtt acc gga cag aag tac ccc aag<br>Trp Pro Leu Tyr Leu Leu Ser Tyr Val Thr Gly Gln Lys Tyr Pro Lys<br>           215                    220                    225 | 966 |
| ctc aac aaa tgg gct gtc aac cac ttc aac ccc aac gcc ccg ctg ttt<br>Leu Asn Lys Trp Ala Val Asn His Phe Asn Pro Asn Ala Pro Leu Phe<br>230                      235                    240 | 1014 |
| gag aag aag gac tgg ttc aac atc tgg atc tct aac gtc ggt att ggt<br>Glu Lys Lys Asp Trp Phe Asn Ile Trp Ile Ser Asn Val Gly Ile Gly<br>245                      250                    255                    260 | 1062 |
| atc acc atg tcc gtc atc gca tac tcc atc aac cga tgg ggc ctg gct<br>Ile Thr Met Ser Val Ile Ala Tyr Ser Ile Asn Arg Trp Gly Leu Ala<br>                        265                    270                    275 | 1110 |
| tcc gtc acc ctc tac tac ctg atc ccc tac ctg tgg gtc aac cac tgg<br>Ser Val Thr Leu Tyr Tyr Leu Ile Pro Tyr Leu Trp Val Asn His Trp<br>280                      285                    290 | 1158 |
| ctc gtg gcc atc acc tac ctg cag cac acc gac ccc act ctg ccc cac<br>Leu Val Ala Ile Thr Tyr Leu Gln His Thr Asp Pro Thr Leu Pro His<br>           295                    300                    305 | 1206 |
| tac cac gcc gac cag tgg aac ttc acc cga gga gcc gcc gcc acc atc<br>Tyr His Ala Asp Gln Trp Asn Phe Thr Arg Gly Ala Ala Ala Thr Ile<br>310                      315                    320 | 1254 |
| gac cga gag ttt ggc ttc atc ggc tcc ttc tgc ttc cat gac atc atc<br>Asp Arg Glu Phe Gly Phe Ile Gly Ser Phe Cys Phe His Asp Ile Ile<br>325                      330                    335                    340 | 1302 |
| gag acc cac gtt ctg cac cac tac gtg tct cga att ccc ttc tac aac<br>Glu Thr His Val Leu His His Tyr Val Ser Arg Ile Pro Phe Tyr Asn<br>                        345                    350                    355 | 1350 |
| gcc cga atc gcc act gag aag atc aag aag gtc atg ggc aag cac tac<br>Ala Arg Ile Ala Thr Glu Lys Ile Lys Lys Val Met Gly Lys His Tyr<br>                    360                    365                    370 | 1398 |
| cga cac gac gac acc aac ttc atc aag tct ctt tac act gtc gcc cga<br>Arg His Asp Asp Thr Asn Phe Ile Lys Ser Leu Tyr Thr Val Ala Arg<br>375                      380                    385 | 1446 |
| acc tgc cag ttt gtt gaa ggt aag gaa ggc att cag atg ttt aga aac<br>Thr Cys Gln Phe Val Glu Gly Lys Glu Gly Ile Gln Met Phe Arg Asn<br>390                      395                    400 | 1494 |
| gtc aat gga gtc gga gtt gct cct gac ggc ctg cct tct aaa aag<br>Val Asn Gly Val Gly Val Ala Pro Asp Gly Leu Pro Ser Lys Lys<br>405                      410                    415 | 1539 |
| tagagctaga aatgttattt gattgtgttt taactgaaca gcaccgagcc cgaggctaag | 1599 |
| ccaagcgaag ccgaggggtt gtgtagtcca tggacgtaac gagtaggcga tatcaccgca | 1659 |
| ctcggcactg cgtgtctgcg ttcatgggcg aagtcacatt acgctgacaa ccgttgtagt | 1719 |
| ttccctttag tatcaatact gttacaagta ccggtctcgt actcgtactg atacgaatct | 1779 |
| gtgggaagaa gtcacccctta tcagaccttc atactgatgt ttcggatatc aatagaactg | 1839 |
| gcatagagcc gttaaagaag tttcacttaa tcactccaac cctcctactt gtagattcaa | 1899 |
| gcagatcgat aagatggatt tgatggtcag tgctagc | 1936 |

<210> SEQ ID NO 49
<211> LENGTH: 419
<212> TYPE: PRT
<213> ORGANISM: Yarrowia lipolytica

<400> SEQUENCE: 49

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380
```

```
Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 50
<211> LENGTH: 25
<212> TYPE: DNA
<213> ORGANISM: Artificial Sequence
<220> FEATURE:
<223> OTHER INFORMATION: Primer P147

<400> SEQUENCE: 50
tcatgccatg gattcgacca cgcag                                    25

<210> SEQ ID NO 51
<211> LENGTH: 26
<212> TYPE: DNA
<213> ORGANISM: Artificial Sequence
<220> FEATURE:
<223> OTHER INFORMATION: Primer P148

<400> SEQUENCE: 51
acatgcggcc gcctactttt tagaag                                   26

<210> SEQ ID NO 52
<211> LENGTH: 35
<212> TYPE: DNA
<213> ORGANISM: Artificial Sequence
<220> FEATURE:
<223> OTHER INFORMATION: Primer YL242

<400> SEQUENCE: 52
cctttagtga gggtttaaac ttcgagcttg gcgta                         35

<210> SEQ ID NO 53
<211> LENGTH: 35
<212> TYPE: DNA
<213> ORGANISM: Artificial Sequence
<220> FEATURE:
<223> OTHER INFORMATION: Primer YL243

<400> SEQUENCE: 53
tacgccaagc tcgaagttta aaccctcact aaagg                         35

<210> SEQ ID NO 54
<211> LENGTH: 32
<212> TYPE: DNA
<213> ORGANISM: Artificial Sequence
<220> FEATURE:
<223> OTHER INFORMATION: Primer YL226

<400> SEQUENCE: 54
tgtggccaac tggtatttaa atgatgtcga cg                            32

<210> SEQ ID NO 55
<211> LENGTH: 32
<212> TYPE: DNA
<213> ORGANISM: Artificial Sequence
<220> FEATURE:
<223> OTHER INFORMATION: Primer YL227

<400> SEQUENCE: 55
cgtcgacatc atttaaatac cagttggcca ca                            32
```

<210> SEQ ID NO 56
<211> LENGTH: 2744
<212> TYPE: DNA
<213> ORGANISM: Artificial Sequence
<220> FEATURE:
<223> OTHER INFORMATION: GPAT::Delta 6B desaturase::Pex20 chimeric gene

<400> SEQUENCE: 56

| | | | | | |
|---|---|---|---|---|---|
| atttaaatgt | agctaacggt | agcaggcgaa | ctactggtac | atacctcccc | cggaatatgt | 60 |
| acaggcataa | tgcgtatctg | tgggacatgt | ggtcgttgcg | ccattatgta | agcagcgtgt | 120 |
| actcctctga | ctgtccatat | ggtttgctcc | atctcaccct | catcgttttc | attgttcaca | 180 |
| ggcggccaca | aaaaaactgt | cttctctcct | tctctcttcg | ccttagtcta | ctcggaccag | 240 |
| ttttagttta | gcttggcgcc | actggataaa | tgagacctca | ggccttgtga | tgaggaggtc | 300 |
| acttatgaag | catgttagga | ggtgcttgta | tggatagaga | agcacccaaa | ataataagaa | 360 |
| taataataaa | acaggggggcg | ttgtcatttc | atatcgtgtt | tcaccatca | atacacctcc | 420 |
| aaacaatgcc | cttcatgtgg | ccagccccaa | tattgtcctg | tagttcaact | ctatgcagct | 480 |
| cgtatcttat | tgagcaagta | aaactctgtc | agccgatatt | gcccgacccg | cgacaagggt | 540 |
| caacaaggtg | gtgtaaggcc | ttcgcagaag | tcaaaactgt | gccaaacaaa | catctagagt | 600 |
| ctctttggtg | tttctcgcat | atatttwatc | ggctgtctta | cgtatttgcg | cctcggtacc | 660 |
| ggactaattt | cggatcatcc | ccaatacgct | ttttcttcgc | agctgtcaac | agtgtccatg | 720 |
| atctatccac | ctaaatgggt | catatgaggc | gtataatttc | gtggtgctga | taataattcc | 780 |
| catatatttg | acacaaaact | tccccccccta | gacatacatc | tcacaatctc | acttcttgtg | 840 |
| cttctgtcac | acatctcctc | cagctgactt | caactcacac | ctctgcccca | gttggtctac | 900 |
| agcggtataa | ggtttctccg | catagaggtg | caccactcct | cccgatactt | gtttgtgtga | 960 |
| cttgtgggtc | acgacatata | tatctacaca | cattgcgcca | cccttttggtt | cttccagcac | 1020 |
| aacaaaaaca | cgacacgcta | accatggcta | cctctgaccc | ttccgtccga | gctttcacac | 1080 |
| gatctgaagt | cttgcacgcc | gatgccttga | acgagggcaa | aaagaatgct | gaagcccgt | 1140 |
| tcctcatgat | cattgacaac | aaagtctacg | atgtgcgcga | gtttgtcccc | gaccatcctg | 1200 |
| gcggtagtgt | cattttgacc | cacgtaggca | aggacggcac | ggacgtcttc | gagaccttcc | 1260 |
| atcccgaggc | cgcgtgggaa | acgctcgcca | acttttatgt | cggcgacatt | gcagaatccg | 1320 |
| atcgtgcgat | tgagaatgac | gagtttgcag | ccgaagtccg | caagctgcgt | actttgttcc | 1380 |
| agtctctggg | atattacaac | tcatccaaaa | cctactacgc | cttcaaggtc | tcattcaacc | 1440 |
| tctgcatctg | gggcctgtcg | gcgtttatgg | ttgccaagtg | gggccagacc | tcgaccctcg | 1500 |
| ccaacgtggt | gtctgcgtcg | cttctggggtg | tcttttggca | acagtgtggt | tggctcgccc | 1560 |
| atgacttctt | acaccaccag | gtcttttcacg | atcggttctg | gggtgatttg | tttggtgcct | 1620 |
| tcctcggcgg | agtctgtcag | gggttctcct | cttcctggtg | gaaggacaaa | cacaacaccc | 1680 |
| accacgcggc | gcccaatgtc | cacggagagg | atcccgatat | cgacacgcac | ccactgttga | 1740 |
| catggagcga | acatgcgctc | gagatgtttt | cggatgtgcc | cgatgaggag | ttggcccaaa | 1800 |
| tgtggtcccg | gttatggtt | gtgaaccaga | cctggttta | cttcccatt | ctgtcgttcg | 1860 |
| cccggttgtc | gtggtgcatt | cagtccattc | tttttgtgct | cccgaacgga | caggcacaca | 1920 |
| agcctgcggg | agcccgggtc | ccatctcgc | tggtggagca | attgtcgctg | gcgatgcatt | 1980 |
| ggacctggta | tctggcgacc | atgttcttgt | ttatcaagga | tcctgtcaac | ataatggtgt | 2040 |

-continued

| | | | | |
|---|---|---|---|---|
| atttcttggt | ctcgcaagcg | gtctgtggca | acctgttggc | gattgtgttc tctctgaacc | 2100 |
| ataacggaat | gcctgtgatc | tctcaggaag | aagcggtcga | gatggatttc tttacaaagc | 2160 |
| agatcattac | gggccgtgat | gtccacccag | gctggttcgc | agactggttc acgggcggat | 2220 |
| tgaactatca | aattgagcac | cacctgttcc | cgtcgatgcc | tcgccactat ttctcaaaga | 2280 |
| tccaaccaac | ggtcgaatca | ttgtgcaaaa | agtacgggt | ccgatatcac acgacgggga | 2340 |
| tgatagatgg | caccgcagag | gtcttttcgc | gactgaacga | ggtctctcag gctgcctcca | 2400 |
| agctcggcaa | gtctgcttga | gcggccgcaa | gtgtggatgg | ggaagtgagt gcccggttct | 2460 |
| gtgtgcacaa | ttggcaatcc | aagatggatg | gattcaacac | agggatatag cgagctacgt | 2520 |
| ggtggtgcga | ggatatagca | acggatattt | atgtttgaca | cttgagaatg tacgatacaa | 2580 |
| gcactgtcca | agtacaatac | taaacatact | gtacatactc | atactcgtac ccgggcaacg | 2640 |
| gtttcacttg | agtgcagtgg | ctagtgctct | tactcgtaca | gtgtgcaata ctgcgtatca | 2700 |
| tagtctttga | tgtatatcgt | attcattcat | gttagttgcg | tacg | 2744 |

GLYCEROL-3-PHOSPHATE O-ACYLTRANSFERASE PROMOTER FOR GENE EXPRESSION IN OLEAGINOUS YEAST

This application claims the benefit of U.S. Provisional Application No. 60/610,060, filed Sep. 15, 2004.

FIELD OF THE INVENTION

This invention is in the field of biotechnology. More specifically, this invention pertains to a promoter region isolated from *Yarrowia lipolytica* that is useful for gene expression in oleaginous yeast.

BACKGROUND OF THE INVENTION

Oleaginous yeast are defined as those organisms that are naturally capable of oil synthesis and accumulation, wherein oil accumulation ranges from at least about 25% up to about 80% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

The technology for growing oleaginous yeast with high oil content is well developed (for example, see EP 0 005 277B1; Ratledge, C., *Prog. Ind. Microbiol.* 16:119-206 (1982)). And, these organisms have been commercially used for a variety of purposes in the past. For example, various strains of *Yarrowa lipolytica* have historically been used for the manufacture and production of: isocitrate lyase; lipases; polyhydroxy-alkanoates; citric acid; erythritol; 2-oxoglutaric acid; γ-decalactone; γ-dodecalactone; and pyruvic acid. More recently, however, the natural abilities of oleaginous yeast have been enhanced by advances in genetic engineering, resulting in organisms capable of producing polyunsaturated fatty acids ("PUFAs"). Specifically, Picataggio et al. have demonstrated that *Y. lipolytica* can be engineered for production of ω-3 and ω-6 fatty acids, by introducing and expressing genes encoding the ω-3/ω-6 biosynthetic pathway (see WO 2004/101757).

Recombinant production of any heterologous protein is generally accomplished by constructing an expression cassette in which the DNA coding for the protein of interest is placed under the control of appropriate regulatory sequences (i.e., promoters) suitable for the host cell. The expression cassette is then introduced into the host cell (usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., oleaginous yeast) for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast. For example, U.S. Pat. No. 4,937,189 and EP220864 (Davidow et al.) disclose the sequence of the XPR2 gene (which encodes an inducible alkaline extracellular protease) and upstream promoter region for use in expression of heterologous proteins. U.S. Pat. No. 6,265,185 (Muller et al.) describe promoters for the translation elongation factor EF1-α (TEF) protein and ribosomal protein S7 that are suitable for expression cloning in yeast and heterologous expression of proteins. These promoters were improved relative to the XPR2 promoter, when tested for yeast promoter activity on growth plates (Example 9, U.S. Pat. No. 6,265,185) and based on their activity in the pH range of 4-11. WO 2005/003310 and commonly owned co-pending U.S. patent application Ser. No. 11/183664 describe regulatory sequences (e.g., promoters, introns) of the glyceraldehyde-3-phosphate dehydrogenase (gpd) and phosphoglycerate mutase (gpm) genes; and, WO 2005/049805 describes regulatory sequences (e.g., promoters, introns) of the fructose-bisphosphate aldolase (fba) gene. Similarly, Juretzek et al. (*Biotech. Bioprocess Eng.*, 5:320-326 (2000)) compares the glycerol-3-phosphate dehydrogenase (G3P), isocitrate lyase (ICL1), 3-oxo-acyl-CoA thiolase (POT1) and acyl-CoA oxidase (POX1, POX2 and POX5) promoters with respect to their regulation and activities during growth on different carbon sources.

Despite the utility of these known promoters, however, there is a need for new improved yeast promoters for metabolic engineering of yeast (oleaginous and non-oleaginous) and for controlling the expression of heterologous genes in yeast. Furthermore, possession of a suite of promoters that are regulatable under a variety of natural growth and induction conditions in yeast will play an important role in industrial settings, wherein it is desirable to express heterologous polypeptides in commercial quantities in said hosts for economical production of those polypeptides. Thus, it is an object of the present invention to provide such promoters that will be useful for gene expression in a variety of yeast cultures, and preferably in *Yarrowia* sp. cultures and other oleaginous yeast.

Applicants have solved the stated problem by identifying the gene (gpat) encoding glycerol-3-phosphate O-acyltransferase (GPAT) from *Yarrowia lipolytica* and the promoter responsible for driving expression of this native gene. The promoter is useful for expression of heterologous genes in *Yarrowia* and has improved activity with respect to the TEF promoter.

SUMMARY OF THE INVENTION

The present invention relates to the isolation of a gene encoding a glycerol-3-phosphate O-acyltransferase (GPAT) enzyme from *Yarrowia* and methods for the expression of a coding region of interest in a transformed yeast, using a promoter of the glycerol-3-phosphate O-acyltransferase (gpat) gene.

Accordingly the invention provides a method for the expression of a coding region of interest in a transformed yeast comprising:
  a) providing a transformed yeast having a chimeric gene comprising:
    (i) a promoter region of a *Yarrowia* gpat gene; and,
    (ii) a coding region of interest expressible in the yeast;
  wherein the promoter region is operably linked to the coding region of interest; and,
  b) growing the transformed yeast of step (a) under conditions whereby the chimeric gene of step (a) is expressed.

In similar fashion the invention provides mutant gpat promoter regions having enhanced promoter activity relative to the wild type promoter.

In a preferred embodiment the invention provides a method for the production of an ω-3 or an ω-6 fatty acid comprising:

a) providing a transformed oleaginous yeast comprising a chimeric gene, comprising:
   (i) a promoter region of a *Yarrowia* gpat gene; and,
   (ii) a coding region encoding at least one enzyme of the ω-3/ω-6 fatty acid biosynthetic pathway;
   wherein the promoter region and coding region are operably linked;
b) culturing the transformed oleaginous yeast of step (a) under conditions whereby the at least one enzyme of the ω-3/ω-6 fatty acid biosynthetic pathway is expressed and a ω-3 or ω-6 fatty acid is produced; and,
c) optionally recovering the ω-3 or ω-6 fatty acid;

wherein the preferred ω-3/ω-6 fatty acid biosynthetic pathway enzymes include, but are not limited to: Δ9 desaturase, Δ12 desaturase, Δ6 desaturase, Δ5 desaturase, Δ17 desaturase, Δ15 desaturase, Δ8 desaturase and Δ4 desaturase; and wherein the preferred ω-3 or ω-6 fatty acid includes, but is not limited to: linoleic acid, α-linolenic acid, γ-linolenic acid, stearidonic acid, dihomo-γ-linoleic acid, eicosatetraenoic acid, arachidonic acid, eicosapentaenoic acid, docosapentaenoic acid, docosahexaenoic acid, eicosadienoic acid and eicosatrienoic acid.

Additionally the invention provides an isolated nucleic acid molecule comprising a gpat promoter selected from the group consisting of SEQ ID NOs:13 and 17.

BRIEF DESCRIPTION OF THE DRAWINGS AND SEQUENCE DESCRIPTIONS

FIG. 1 graphically represents the relationship between SEQ ID NOs:3, 4, 13, 14 and 17, each of which relates to glycerol-3-phosphate O-acyltransferase (GPAT) in *Y. lipolytica*.

FIG. 2 provides plasmid maps for the following: (A) pY5-30; (B) pDMW214; and (C) pYGPAT-GUS.

FIG. 3A diagrams the development of *Y. lipolytica* ATCC #20362 derivative pDMW236-#18. FIG. 3B provides a plasmid map for pKUNF12T6E; and FIG. 3C provides a plasmid map for pDMW236.

Figure 4:
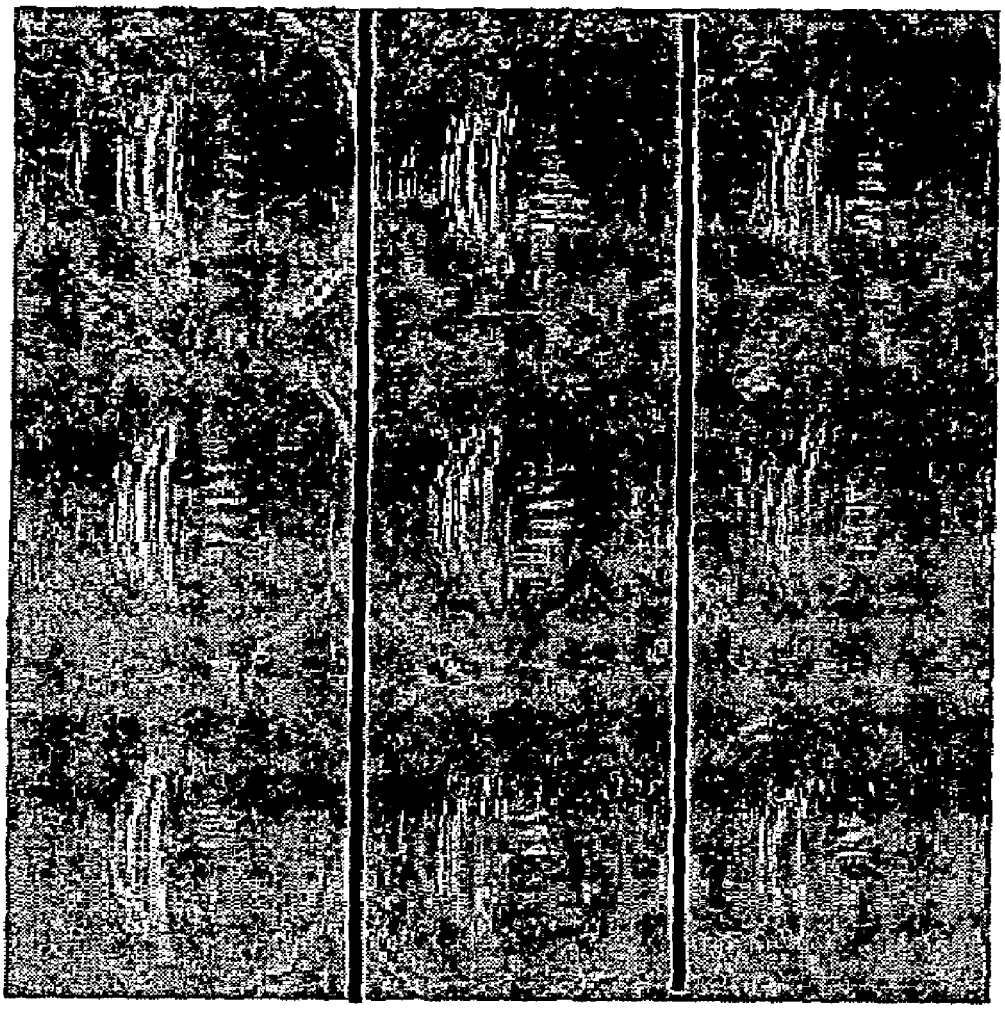

FIG. 4 illustrates the relative promoter activities of TEF, GPAT and FBAIN in *Y. lipolytica* as determined by histochemical staining.

FIG. 5 provides plasmid maps for the following: (A) pY5-13; (B) pY25-d12d; and (C) pZGP6B, respectively.

Figure 6:
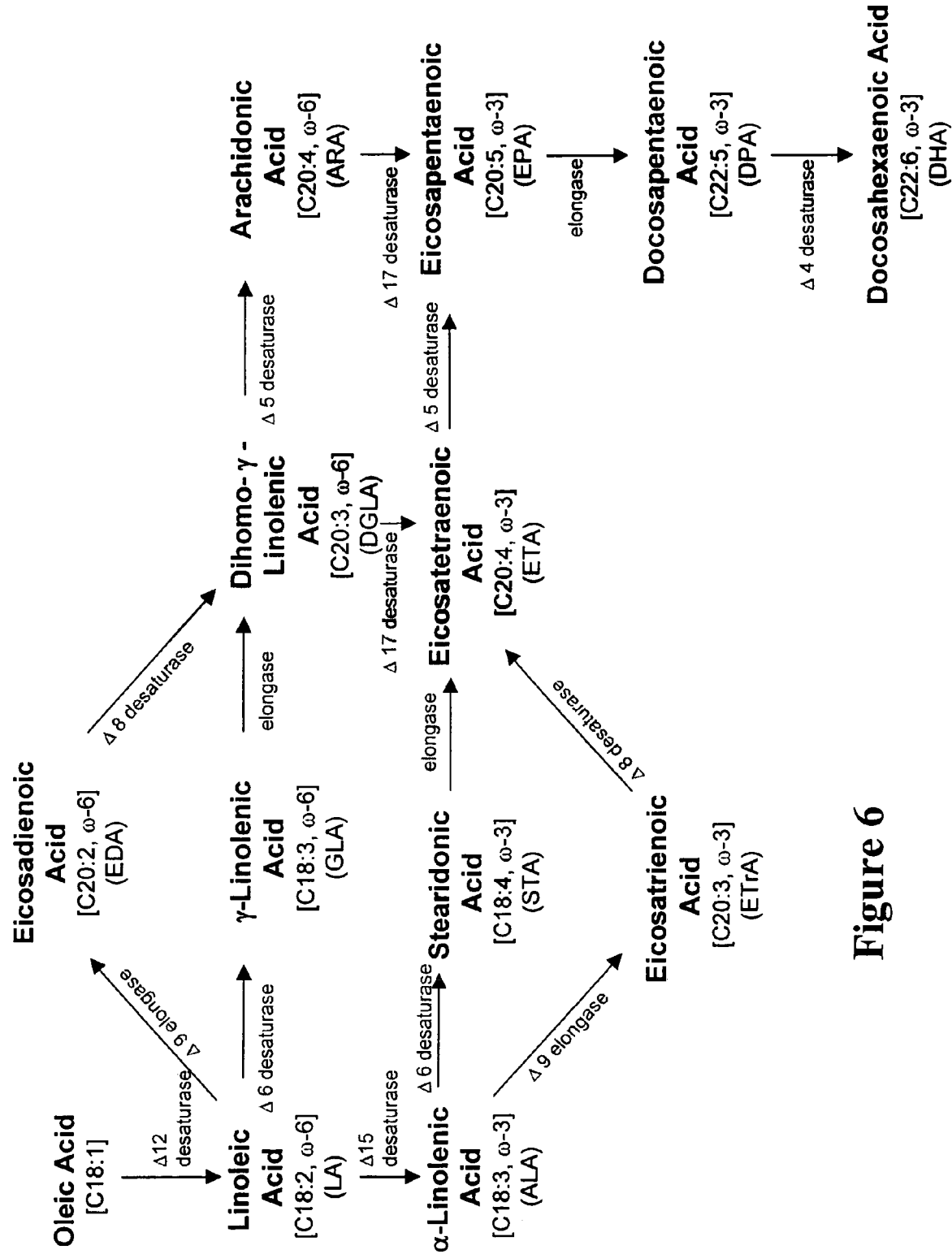

FIG. 6 illustrates the ω-3/ω-6 fatty acid biosynthetic pathway.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-4, 14-17, 20-30, 36, 45, 48-49 and 56 correspond to ORFs (i.e., encoding genes or proteins), promoters, terminators and plasmids, as identified in Table 1.

TABLE 1

Summary Of Nucleotide And Protein SEQ ID Numbers

| Description | Nucleotide SEQ ID NO | Protein SEQ ID NO |
|---|---|---|
| *Saccharomyces cerevisiae* Gat2(SCT1) (GenBank Accession No. AJ314608) | — | 1 (750 AA) |
| *Saccharomyces cerevisiae* Gat1 (GenBank Accession No. AJ311354) | — | 2 (743 AA) |
| *Yarrowia lipolytica* glycerol-3-phosphate O-acyltransferase (gpat) gene | 3 (2184 bp) | — |
| *Yarrowia lipolytica* ORF YALI-CDS1055.1 (GenBank Accession No. CAG81570) | — | 4 (727 AA) |
| *Yarrowia lipolytica* gpat gene: −1678 to +2181 region | 14 (3862 bp) | — |
| Plasmid pY5-30 | 15 (8953 bp) | — |
| FBAIN promoter (WO 2005/049805) | 16 (995 bp) | — |
| GPAT promoter "GPATPro", corresponding to to the −1130 to −1 region of the gpat gene | 17 (1130 bp) | — |
| Plasmid pKUNF12T6E | 20 (12,649 bp) | — |
| Synthetic elongase gene derived from *Mortierella alpina*, codon-optimized for expression in *Yarrowia lipolytica* | 21 (957 bp) | 22 (318 AA) |
| Synthetic Δ6 desaturase, derived from *Mortierella alpina*, codon-optimized for expression in *Yarrowia lipolytica* | 23 (1374 bp) | 24 (457 AA) |
| FBA promoter (WO 2005/049805) | 25 (1001 bp) | — |
| *Fusarium moniliforme* Δ12 desaturase (WO 2005/047485) | 26 (1434 bp) | 27 (477 AA) |
| Synthetic elongase gene derived from *Thraustochytrium aureum*, codon-optimized for expression in *Yarrowia lipolytica* | 28 (819 bp) | 29 (272 AA) |
| Plasmid pDMW236 | 30 (13,006 bp) | — |
| *Mortierella alpina* Δ6 desaturase (GenBank Accession No. AB070555; referred to herein as "Δ6B" in plasmid pT-6BC) | 36 (1377 bp) | — |
| *Yarrowia* Pex20 terminator (GenBank Accession No. AF054613) | 45 (324 bp) | — |
| *Yarrowia lipolytica* Δ12 desaturase (WO 2004/104167) | 48 (1936 bp) | 49 (419 AA) |
| GPAT::Δ6B::Pex20 chimeric gene | 56 (2744 bp) | — |

SEQ ID NOs:5 and 6 correspond to the degenerate primers YGPAT-F and YGPAT-R, respectively, used for amplifying the *Yarrowia lipolytica* ORF YALI-CDS1055.1.

SEQ ID NOs:7 and 8 correspond to the Genome Walker adaptor used to isolate the GPAT promoter region by genome-walking.

SEQ ID NOs:9-12 correspond to the PCR primers used in genome-walking: Adaptor-1, YGPAT-5R-1, Nested Adaptor Primer 2 and YGPAT-5R-2, respectively.

SEQ ID NO:13 corresponds to a 1781 bp fragment contained within plasmid pEcoRV-G-5, the fragment containing a 1678 bp region upstream of the translation initiation codon 'ATG' of the gpat gene (wherein the 'A' position of the 'ATG' translation initiation codon is designated as +1).

SEQ ID NOs:18 and 19 correspond to primers GPAT-5-1 and GPAT-5-2, respectively, used to amplify "GPATPro".

SEQ ID NOs:31-33 correspond to BD-Clontech Creator Smart® cDNA library kit primers SMART IV oligo nucleotide, CDSIII/3' PCR primer and 5'-PCR primer, respectively.

SEQ ID NOs:34 and 35 correspond to primers YL421 and YL422, respectively, used to amplify the *Mortierella alpina* Δ6B desaturase.

SEQ ID NOs:37-42 correspond to primers YL475, YL476, YL477, YL478, YL479 and YL480, respectively, used for in vitro mutagenesis within the *M. alpina* Δ6B desaturase.

SEQ ID NOs:43 and 44 correspond to primers YL497 and YL498, respectively, used to amplify GPATPro.

SEQ ID NOs:46 and 47 correspond to primers YL259 and YL260, respectively, used to amplify the *Yarrowia* Pex20 terminator.

SEQ ID NOs:50 and 51 correspond to primers P147 and P148, used to amplify the *Y. lipolytica* Δ12 desaturase.

SEQ ID NOs:52-55 correspond to primers YL242, YL243, YL226 and YL227, respectively, used for site-directed mutagenesis during generation of plasmid pY25-d12d-PS.

DETAILED DESCRIPTION OF THE INVENTION

All patents, patent applications, and publications cited herein are incorporated by reference in their entirety including not limited to, the following commonly owned copending applications: U.S. patent application Ser. No. 10/840478 (filed May 6, 2004), U.S. patent application Ser. No. 10/840579 (filed May 6, 2004), U.S. patent application Ser. No. 10/840325 (filed May 6, 2004), U.S. patent application Ser. No. 10/869630 (filed Jun. 16, 2004), U.S. patent application Ser. No. 10/987548 (filed Nov. 12, 2004), U.S. patent application Ser. No. 60/624812 (filed Nov. 4, 2004) and U.S. patent application Ser. No. 11/183664 (filed Jul. 18, 2005).

Applicants describe herein the isolation and characterization of a promoter and gene from an oleaginous yeast, *Yarrowia lipolytica*. This promoter region, isolated upstream of the glycerol-3-phosphate O-acyltransferase (gpat) gene, is useful for genetic engineering in *Y. lipolytica* and other yeasts for the production of heterologous polypeptides.

Preferred heterologous polypeptides of the present invention are those that are involved in the synthesis of microbial oils and particularly polyunsaturated fatty acids (PUFAs). PUFAs, or derivatives thereof, made by the methodology disclosed herein can be used in many applications. For example, the PUFAs can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products, and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Thus, the present invention advances the art by providing methods for the expression of a coding region of interest in a transformed yeast comprising: a) providing a transformed yeast having a chimeric gene comprising (i) a promoter region of a *Yarrowia* gpat gene; and, (ii) a coding region of interest expressible in the yeast, wherein the promoter region is operably linked to the coding region of interest; b) growing the transformed yeast of step (a) under conditions whereby the chimeric gene is expressed; and, c) optionally isolating the gene product from the cultivation medium. In preferred embodiments, the GPAT promoter region comprises a sequence selected from the group consisting of SEQ ID NOs:13 and 17.

Definitions

In this disclosure, a number of terms and abbreviations are used. The following definitions are provided.

"Glycerol-3-phosphate O-acyltransferase" is abbreviated GPAT.

"Open reading frame" is abbreviated ORF.

"Polymerase chain reaction" is abbreviated PCR.

"Polyunsaturated fatty acid(s)" is abbreviated PUFA(s).

The term "oleaginous" refers to those organisms that tend to store their energy source in the form of lipid (Weete, In: Fungal Lipid Biochemistry, 2$^{nd}$ Ed., Plenum, 1980). Generally, the cellular PUFA content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeast that can accumulate at least 25% of their dry cell weight as oil. Examples of oleaginous yeast include (but are no means limited to) the following genera: *Yarrowia, Candida, Rhodotorula, Rhodosporidium, Cryptococcus, Trichosporon* and *Lipomyces*. The term "GPAT" refers to a glycerol-3-phosphate O-acyltransferase enzyme (E.C. 2.3.1.15) encoded by the gpat gene and which converts acyl-CoA and sn-glycerol 3-phosphate to CoA and 1-acyl-sn-glycerol 3-phosphate (the first step of phospholipid biosynthesis). Two representative gpat genes from *Saccharomyces cerevisiae* are GenBank Accession No. AJ314608 (Gat2(SCT1); SEQ ID NO:1) and GenBank Accession No. AJ311354 (Gat1; SEQ ID NO:2) (Zheng, Z. and J. Zou. *J. Biol. Chem.* 276(45):41710-41716 (2001)). A gpat gene isolated from *Yarrowia lipolytica* is provided as SEQ ID NO:3, while the corresponding amino acid sequence is provided as SEQ ID NO:4.

The term "GPAT promoter" or "GPAT promoter region" refers to the 5' upstream untranslated region in front of the 'ATG' translation initiation codon of gpat and that is necessary for expression. Examples of suitable GPAT promoter regions are provided as SEQ ID NOs:13 and 17, but these are not intended to be limiting in nature. One skilled in the art will recognize that since the exact boundaries of the GPAT promoter sequence have not been completely defined, DNA fragments of increased or diminished length may have identical promoter activity.

The term "GPD" refers to a glyceraldehyde-3-phosphate dehydrogenase enzyme (E.C. 1.2.1.12) encoded by the gpd gene and which converts D-glyceraldehyde 3-phosphate to 3-phospho-D-glyceroyl phosphate during glycolysis. The term "GPD promoter" or "GPD promoter region" refers to the 5' upstream untranslated region in front of the 'ATG' translation initiation codon of gpd and that is necessary for expression. Examples of suitable *Yarrowia lipolytica* GPD promoter regions are described in U.S. patent application Ser. No. 10/869630.

The term "GPM" refers to a phosphoglycerate mutase enzyme (EC 5.4.2.1) encoded by the gpm gene and which is responsible for the interconversion of 3-phosphoglycerate and 2-phosphoglycerate during glycolysis. The term "GPM promoter" or "GPM promoter region" refers to the 5' upstream untranslated region in front of the 'ATG' translation initiation codon of gpm and that is necessary for expression. Examples of suitable *Yarrowia lipolytica* GPM promoter regions are described in U.S. patent application Ser. No. 10/869630.

The term "FBA1" refers to a fructose-bisphosphate aldolase enzyme (E.C. 4.1.2.13) encoded by the fba1 gene and which converts D-fructose 1,6-bisphosphate into glycerone phosphate and D-glyceraldehyde 3-phosphate. The term "FBA promoter" or "FBA promoter region" refers to the 5' upstream untranslated region in front of the 'ATG' translation initiation codon of fba1 and that is necessary for expression. An example of a suitable FBA promoter region is provided as SEQ ID NO:25, but this is not intended to be limiting in nature (see WO 2005/049805). The term "FBAIN promoter" or "FBAIN promoter region" refers to the 5' upstream untranslated region in front of the 'ATG' translation initiation codon of fba1 and that is necessary for expression, plus a portion of 5' coding region comprising an intron of the fba1 gene. An example of a suitable FBAIN promoter region is provided as SEQ ID NO:16, but this is not intended to be limiting in nature (see WO 2005/049805).

The term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The instant specification teaches partial or complete amino acid and nucleotide sequences encoding one or more particular microbial proteins and promoters. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "oligonucleotide" refers to a nucleic acid, generally of at least 18 nucleotides, that is hybridizable to a genomic DNA molecule, a cDNA molecule, or an mRNA molecule. In one embodiment, a labeled oligonucleotide can be used as a "probe" to detect the presence of a nucleic acid according to the invention. Thus, the term "probe" refers to a single-stranded nucleic acid molecule that can base pair with a complementary single-stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

Likewise, suitable promoter regions (isolated polynucleotides of the present invention) encode promoter regions that are at least about 70% identical, preferably at least about 75% identical, and more preferably at least about 80% identical to the nucleotide sequences reported herein. Preferred nucleic acid fragments are about 85% identical to the nucleotide sequences reported herein, more preferred nucleic acid fragments are at least about 90% identical, and most preferred are nucleic acid fragments at least about 95% identical to the nucleotide sequences reported herein. Suitable promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the instant microbial polypeptide as set forth in SEQ ID NO:4. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise a GPAT promoter region operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to transcriptional and translational nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "mutant promoter" is defined herein as a promoter having a nucleotide sequence comprising a substitution, deletion, and/or insertion of one or more nucleotides relative to the parent promoter, wherein the mutant promoter has more or less promoter activity than the corresponding parent promoter. The term "mutant promoter" will encompass natural variants and in vitro generated variants obtained using methods well known in the art (e.g., classical mutagenesis, site-directed mutagenesis and "DNA shuffling").

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a coding sequence. Expression may also refer to translation of mRNA into a polypeptide.

"Introns" are sequences of non-coding DNA found in gene sequences (either in the coding region, 5' non-coding region, or 3' non-coding region) in most eukaryotes. Their full function is not known; however, some enhancers are located in the introns (Giacopelli F. et al., *Gene Expr.* 11:95-104 (2003)). These intron sequences are transcribed, but removed from within the pre-mRNA transcript before the mRNA is translated into a protein. This process of intron removal occurs by self-splicing of the sequences (exons) on either side of the intron.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); and 4.) the FASTA program incorporating the Smith-Waterman algorithm (W. R. Pearson, *Comput. Methods Genome Reis.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Identification of GPAT in *Yarrowia lipolytica*

GPAT encodes a glycerol-3-phosphate O-acyltransferase that is responsible for carrying out the initial step of phospholipid biosynthesis in yeast. Specifically, the enzyme acylates glycerol 3-phosphate (G-3-P) and dihydroxyacetone phosphate at the sn-1 position; this permits formation of lysophosphatidic acid (LPA) and acyl-dihydroxyacetone (acyl-DHAP). LPA acyltransferase then catalyzes the acylation of LPA at the sn-2 position to generate phosphatidic acid, which serves as a general precursor for all glycerophospholipids (e.g., triacylglycerols). Although it was widely accepted that multiple isoforms of G-3-P acyltransferases were present in yeast, it was not until the work of Zheng and Zou (*J. Biol. Chem.* 276(45):41710-41716 (2001); WO 02/08391 A2) that two genes encoding this enzyme were identified and sequenced from *Saccharomyces cerevisiae* (i.e., Gat1 [GenBank Accession No. AJ311354] and Gat2(SCT1) [GenBank Accession No. AJ314608]).

The present invention identifies the complete nucleotide sequence encoding a *Yarrowia lipolytica* glycerol-3-phosphate O-acyltransferase (GPAT) contained within ORF YALI-CDS1055.1 (Genolevures project, sponsored by the Center for Bioinformatics, LaBRI, bâtiment A30, Universite Bordeaux 1, 351, cours de la Libération, 33405 Talence Cedex, France; see also GenBank Accession No. CAG81570). The amino acid sequence of this ORF was publicly available prior to the Applicants' invention and the ORF was annotated as having similarity to the *Saccharomyces cerevisiae* GPATs. Based on sequence comparison to the *S. cerevisiae* Gat1 and Gat2(SCT1) genes (supra), the Applicants hypothesized that ORF YALI-CDS1055.1 likely encoded the *Y. lipolytica* GPAT. Subsequently, sequencing of the *Y. lipolytica* ORF confirmed the Applicants' deduction and permitted annotation of the gene within ORF YALI-CDS1055.1 (also GenBank Accession No. CAG81570) as the *Y. lipolytica* GPAT.

As expected, comparison of the gpat nucleotide base (SEQ ID NO:3) and deduced amino acid sequence to the Genolevures database of *Y. lipolytica* ORFs reveals that the amino acid sequence of gpat reported herein over a length of 727 amino acids has 100% identity to the *Y. lipolytica* ORF identified as YALI-CDS1055.1 (SEQ ID NO:4).

Identification of the GPAT Promoter Region in *Yarrowia lipolytica*

Although numerous studies have examined GPAT and its ability to affect triacylglyceride and phospholipid synthesis (e.g., WO 00/78974 A2; WO 02/08391 A2; Mishra, S. and Kamisaka, Y. *Biochem. J.* 355:315-322 (2001)), few have investigated the GPAT promoter. One exception is the work of Jerkins et al. (*J. Biol. Chem.* 270(3):1416-1421 (1995)), wherein the murine mitochondrial GPAT promoter (GenBank Accession No. U11680) was characterized.

In the present invention, it was desirable to identify the putative promoter region that naturally regulates gpat in the oleaginous yeast, *Yarrowia lipolytica*, following isolation of the gene encoding GPAT. And, based on the work described herein, this putative promoter region has been identified as useful for driving expression of any suitable coding region of interest in a transformed yeast.

In general, a promoter useful in an oleaginous yeast should meet the following criteria:

1.) Strength. A strong yeast promoter is a necessary premise for a high expression level, and the low copy number of the ars18 (Fournier, P. et al., *Yeast* 7:25-36 (1991)) based expression vectors or chimeric genes integrated into the genome makes this demand even more important when *Y. lipolytica* is used as the host organism.

2.) Activity in a medium suitable for expression of the coding region of interest, and high enzymatic activity of that coding region of interest.

3.) pH Tolerance. If the coding region of interest is known to be produced only in e.g., an acidic environment, then the promoter operably linked to said coding region of interest must function at the appropriate pH. pH tolerance is of course limited by the tolerance of the host organism.

4.) Inducibility. A tightly regulated yeast promoter makes it possible to separate the growth stage from the expression stage, thereby enabling expression of products that are known to inhibit cell growth.

5.) Activity in the stationary phase of growth in oleaginous yeast hosts for accumulation of PUFAs.

Additionally, it is preferable for novel yeast promoters to possess differences in activity with respect to the known *Y. lipolytica* TEF (U.S. Pat. No. 6,265,185), XPR2 (U.S. Pat. No. 4,937,189; EP220864; EP832258), GPD (WO 2005/003310), GPDIN (U.S. patent application Ser. No. 11/183664), GPM (WO 2005/003310), FBA (WO 2005/049805) and FBAIN (WO 2005/049805) promoters and/or the G3P, ICL1, POT1, POX1, POX2 and POX5 promoters (Juretzek et al., *Biotech. Bioprocess Eng.*, 5:320-326 (2000)). A comparative study of the TEF and FBAIN promoters and the GPAT promoter of the instant invention is provided in Example 7. It is shown that the yeast promoter of the present invention has improved activity compared to the TEF promoter, and diminished activity with respect to FBAIN.

An example of a suitable GPAT promoter region is provided as SEQ ID NO:17 (comprising the −1130 to −1 region of the *Y. lipolytica* gpat gene (wherein the 'A' position of the 'ATG' translation initiation codon is designated as +1)), but this is not intended to be limiting in nature. One skilled in the art will recognize that since the exact boundaries of the GPAT promoter sequence have not been completely defined, DNA fragments of increased or diminished length may have identical promoter activity. For example, in an alternate embodiment, the GPAT promoter will comprise nucleotides −500 to −1 of SEQ ID NO:17, thereby permitting relatively strong promoter activity; in another embodiment, the −100 to −1 region of SEQ ID NO:17 should be sufficient for basal activity of the promoter. Likewise, the promoter region of the invention may comprise additional nucleotides to those specified above. For example, the promoter sequences of the invention may be constructed on the basis of the −1678 to +1 region of the gpat1 gene (based on SEQ ID NO:13).

In alternate embodiments mutant promoters may be constructed, wherein the DNA sequence of the promoter has one or more nucleotide substitutions (i.e., deletions, insertions, substitutions, or addition of one or more nucleotides in the sequence) which do not effect (in particular impair) the yeast promoter activity. Regions that can be modified without significantly affecting the yeast promoter activity can be identified by deletion studies. A mutant promoter of the present invention is at least about 20%, preferably at least about 40%, more preferably at least about 60%, more preferably at least about 80%, more preferably at least about 90%, more preferably at least about 100%, more preferably at least about 200%, more preferably at least about 300% and most preferably at least about 400% greater than the promoter activity of the wildtype GPAT promoter region described herein as SEQ ID NO:17.

Methods for mutagenesis are well known in the art and suitable for the generation of mutant promoters. For example, in vitro mutagenesis and selection, PCR based random mutagenesis, site-directed mutagenesis or other means can be employed to obtain mutations of the naturally occurring promoter or gene of the instant invention (wherein such mutations may include deletions, insertions and point mutations, or combinations thereof). This would permit production of a putative promoter having a more desirable level of promoter activity in the host cell. Or, if desired, the regions of a nucleotide of interest important for promoter activity can be determined through routine mutagenesis, expression of the resulting mutant promoters and determination of their activities. An overview of these techniques are described in WO2005/003310. All such mutant promoters that are derived from the instant GPAT promoter described herein are within the scope of the present invention.

Promoter activity is typically measured against the activity of the wild type promoter under similar conditions. Promoter activity is generally measured as a function of gene expression and may be determined in a variety of ways including gene expression profiling, measurement of the level of protein expression by SDS gel or other means, or the measurement of reporter activity where reporter gene fusions have been created.

Isolation of Homologs of the GPAT Putative Promoter Region

It will be appreciated by a person of skill in the art that the promoter regions and gene of the present invention have homologs in a variety of yeast species; and, the use of the promoters and genes for heterologous gene expression are not limited to those promoters and genes derived from *Y. lipolytica*, but extend to homologs in other yeast species. For example, the invention encompasses homologs derived from oleaginous genera including, but not limited to: *Yarrowia, Candida, Rhodotorula, Rhodosporidium, Cryptococcus, Trichosporon* and *Lipomyces*; examples of preferred species within these genera include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*.

Homology typically is measured using sequence analysis software, wherein the term "sequence analysis software" refers to any computer algorithm or software program (commercially available or independently developed) that is useful for the analysis of nucleotide or amino acid sequences. In general, such computer software matches similar sequences by assigning degrees of homology to various substitutions, deletions and other modifications.

As is well known in the art, isolation of homologous promoter regions or genes using sequence-dependent protocols is readily possible using various techniques; and, these techniques can rely on either the direct identification of a promoter having homology to the GPAT promoter of the invention or the indirect identification of a promoter by initial identification of gene having significant homology to the gpat gene and then analysis of the 5' upstream sequence of the homologous gene. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, putative promoter regions or genes encoding similar proteins or polypeptides to those of the instant invention could be isolated by using all or a portion of the instant nucleic acid fragments as DNA hybridization probes to screen libraries from any desired microbe using methodology well known to those skilled in the art. Specific oligonucleotide probes based upon the instant nucleic acid sequences can be designed and synthesized by methods known in the art (Sambrook, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis (Ed.), (1986) pp 33-50 IRL: Herndon, Va.; and Rychlik, W., In *Methods in Molecular Biology*, White, B. A. (Ed.), (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous polynucleotides from DNA or RNA. The PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the instant sequences may be employed as hybridization reagents for the identification of homologs. The basic components of a nucleic acid hybridization test include a probe, a sample suspected of containing the nucleotide sequence of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wtvol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Recombinant Expression in Yeast

Initiation control regions or promoter regions that are useful to drive expression of a coding gene of interest in the desired host cell are selected from those derived from the upstream portion of the gpat gene (SEQ ID NO:3). The promoter regions may be identified from the upstream sequences of gpat and its homologs and isolated according to common methods (Maniatis, supra). Once the promoter regions are identified and isolated (e.g., SEQ ID NOs:13 and 17), they may be operably linked to a coding region of interest to be expressed in a suitable expression vector. These chimeric genes may then be expressed in natural host cells and heterologous host cells, particularly in the cells of oleaginous yeast hosts. Thus, one aspect of the present invention provides a recombinant expression vector comprising a yeast promoter of the invention.

In a further aspect, the invention provides a method of expressing a coding region of interest in a transformed yeast, wherein a transformed yeast is provided having a chimeric gene comprising: (i) a promoter region of a *Yarrowia* gpat gene; and, (ii) a coding region of interest expressible in the yeast, wherein the promoter region is operably linked to the coding region of interest; and the transformed yeast is grown under conditions wherein the chimeric gene is expressed. The polypeptide so produced can optionally be recovered from the culture.

Microbial expression systems and expression vectors are well known to those skilled in the art. Any of these could be used to construct chimeric genes comprising a promoter region derived from the gpat gene for production of any specific coding region of interest suitable for expression in a desirable yeast host cell. These chimeric genes could then be introduced into appropriate microorganisms by integration via transformation to provide high-level expression of the enzymes upon induction. Alternatively, the promoters can be cloned into a plasmid that is capable of transforming and replicating itself in the preferred yeast. The coding region of interest to be expressed can then be cloned downstream from the promoter. Once the recombinant host is established, gene expression can be accomplished by growing the cells under suitable conditions (infra).

Suitable Coding Regions of Interest

Useful chimeric genes will include the promoter region of the gpat gene as defined herein or a mutant promoter thereof, operably linked to a suitable coding region of interest to be expressed in a preferred host cell.

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect or vertebrate coding regions of interest, including mammalian polypeptides. Further, these coding regions of interest may be, for example, structural proteins, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, β-glucanases, β-galactosidases, glucoamylases, α-glucosidases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases or xylanases.

Preferred in the present invention in some embodiments are coding regions of the enzymes involved in the production of microbial oils, including ω-6 and ω-3 fatty acids. These coding regions include desaturases and elongases (e.g., see WO 2004/101757 for a partial review of available genes in GenBank and/or the patent literature and considerations for choosing a specific polypeptide having desaturase or elongase activity).

Components of Vectors/DNA Cassettes

Vectors or DNA cassettes useful for the transformation of suitable host cells are well known in the art. The specific choice of sequences present in the construct is dependent upon the desired expression products (supra), the nature of the host cell, and the proposed means of separating transformed cells versus non-transformed cells. Typically, however, the vector or cassette contains sequences directing transcription and translation of the relevant gene(s), a selectable marker, and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence motif to obtain optimal gene expression. For expression in yeast, this can be done by site-directed mutagenesis of an inefficiently expressed gene to include the favored translation initiation motif.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces*, *Schizosaccharomyces*, *Candida*, *Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a chimeric gene into a cloning vector does not ensure that it will be successfully expressed at the level needed. In response to needs for high expression rates, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) whether the gene is plasmid-borne or integrated into the genome of the host cell and the number of copies of the cloned gene [e.g., additional copies of a particular coding region of interest (operably linked to the promoter of the instant invention) may be introduced into the host to increase expression]; 3.) the final cellular location of the synthesized foreign protein; 4.) the efficiency of translation in the host organism; 5.) the intrinsic stability of the cloned gene protein within the host cell [e.g., expression of the coding region of interest can be increased by removing/deleting destabilizing sequences from either the mRNA or the encoded protein or by adding stabilizing sequences to the mRNA (U.S. Pat. No. 4,910,141)]; and 6.) the codon usage within the cloned gene, such that its frequency approaches the frequency of preferred codon usage of the host cell [e.g. translational efficiency of the encoded mRNAs can be increased by replacement of codons in the native gene with those for optimal gene expression in the selected host microorganism, to thereby substantially enhance the expression of the foreign gene encoding the polypeptide]. Each of these types of modifications are encompassed in the present invention, as means to further optimize expression of a chimeric gene comprising a promoter region of the gpat gene as defined herein or a mutant promoter thereof, operably linked to a suitable coding region of interest.

Transformation of Yeast Cells

Once an appropriate chimeric gene has been constructed that is suitable for high-level expression in a yeast cell, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising a coding region of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in WO 2004/101757 and WO2005/003310. Preferred Hosts Preferred host cells for expression of the instant gene and coding regions of interest operably linked to the instant promoter fragments herein are yeast cells (where oleaginous yeast are most preferred where the desired use is for the production of microbial oils, infra). Oleaginous yeast are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)). The *Y. lipolytica* strain designated as ATCC #20362 was the particular strain from which the GPAT promoter and gene was isolated therefrom.

Industrial Production Using Transformed Yeast Expressing a Suitable Coding Region of Interest In general, media conditions that may be optimized for expression of a particular coding region of interest include the type and amount of carbon source, the type and amount of nitrogen source, the carbon-to-nitrogen ratio, the oxygen level, growth temperature, pH, length of the biomass production phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Host cells comprising a suitable coding region of interest operably linked to the promoters of the present invention may be cultured using methods known in the art. For example, the cell may be cultivated by shake flask cultivation, small-scale or large-scale fermentation in laboratory or industrial fermentors performed in a suitable medium and under conditions allowing expression of the coding region of interest. Furthermore, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process, as is well known in the art (see, e.g., Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), each herein incorporated by reference).

DESCRIPTION OF PREFERRED EMBODIMENTS

Although the promoters of the present invention will be suitable for expression of any suitable coding region of interest in an oleaginous yeast, in a preferred embodiment the promoters will be utilized in the development of an oleaginous yeast that accumulates high levels of oils enriched in PUFAs. Toward this end, it is necessary to introduce and express e.g., desaturases and elongases that allow for the synthesis and accumulation of ω-3 and/or ω-6 fatty acids.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "ω-6 fatty acids" (ω-6 or n-6) versus "ω-3 fatty acids" (ω-3 or n-3) are provided in WO2004/1 01757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids, the abbreviations that will be used throughout the remainder of the specification, and each compounds' chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Microbial Biosynthesis of Omega-3 and Omega-6 Fatty Acids

The process of de novo synthesis of palmitate (16:0) in oleaginous microorganisms is described in WO 2004/101757. This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a Δ9 desaturase; similarly, palmitate is elongated to form stearic acid (18:0), which can be converted to its unsaturated derivative by a Δ9 desaturase to thereby yield oleic (18:1) acid.

The metabolic process that converts LA to GLA, DGLA and ARA (the ω-6 pathway) and ALA to STA, ETA, EPA and DHA (the ω-3 pathway) is well described in the literature and is schematically depicted in FIG. 6 (see also WO2004/101757 and WO2005/003310). Simplistically, this process involves elongation of the carbon chain through the addition of carbon atoms and desaturation of the molecule through the addition of double bonds, via a series of special desaturation and elongation enzymes present in the endoplasmic reticulim membrane (and hereinafter referred to as "PUFA biosynthetic pathway enzymes"). More specifically, "PUFA biosynthetic pathway enzymes" or "ω-3/ω-6 biosynthetic pathway enzymes" will refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s). For further clarity within the present disclosure, the term "desaturase" refers to a polypeptide that can desaturate one or more fatty acids to produce a mono- or polyunsaturated fatty acid or precursor of interest. Thus, despite use of the omega-reference system to refer to specific fatty acids, it is more convenient to indicate the activity of a desaturase by counting from the carboxyl end of the source using the delta-system. For example, a Δ17 desaturase will desaturate a fatty acid between the $17^{th}$ and $18^{th}$ carbon atom numbered from the carboxyl-terminal end of the molecule and can, for example, catalyze the conversion of ARA to EPA and/or DGLA to ETA. In contrast, the term "elongase" refers to a polypeptide that can elongate a fatty acid carbon chain to produce a mono- or polyunsaturated fatty acid that is 2 carbons longer than the fatty acid source that the elongase acts upon. This process of elongation occurs in a multi-step mechanism in association with fatty acid synthase, whereby CoA is the acyl carrier (Lassner et al., *The Plant Cell* 8:281-292 (1996)).

As will be understood by one skilled in the art, the particular functionalities required to be introduced into a host organism for production of a particular PUFA final product will depend on the host cell (and its native PUFA profile and/or desaturase/elongase profile), the availability of substrate and the desired end product(s). As shown in FIG. 6, LA, GLA, EDA, DGLA, ARA, ALA, STA, ETrA, ETA, EPA, DPA and DHA may all be produced in oleaginous yeast, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s). One skilled in the art will be able to identify various candidate genes encoding each of the above enzymes, according to publicly available literature (e.g., GenBank), the patent literature, and experimental analysis of microorganisms having the ability to produce PUFAs. Thus, a variety of desaturases and elongases are suitable as coding regions of interest in the present invention. These coding regions of interest could be operably linked to the GPAT promoters of the present invention or mutant promoters thereof, and used as chimeric genes for expression of various ω-6 and ω-3 fatty acids, using techniques well known to those skilled in the art (e.g., see WO 2004/101757). As such, the invention provides a method for the production of ω-3 and/or ω-6 fatty acids comprising:

a) providing a transformed oleaginous yeast comprising a chimeric gene, said gene comprising:
1) a promoter region of a *Yarrowia* gpat gene; and,
2) a coding region of interest encoding at least one enzyme of the ω-3/ω-6 fatty acid biosynthetic pathway;
wherein the promoter region and coding region are operably linked;

b) culturing the transformed oleaginous yeast of step (a) under conditions whereby the at least one enzyme of the ω-3/ω-6 fatty acid biosynthetic pathway is expressed and a ω-3 or ω-6 fatty acid is produced; and, c) optionally recovering the ω-3 or ω-6 fatty acid.

In preferred embodiments, the nucleic acid sequence of the promoter region is selected from the group consisting of: SEQ ID NOs:13 and 17, and subsequences and mutant promoters thereof; and the coding region of interest is any desaturase or elongase suitable for expression in the oleaginous yeast for the production of ω-3 or ω-6 fatty acids.

For production of the greatest and the most economical yield of PUFAs, the transformed oleaginous yeast host cell is grown under conditions that optimize desaturase and elongase activities by optimizing expression of the chimeric genes of the present invention, wherein these chimeric genes comprise a promoter region of a gpat gene and a coding region of interest encoding a PUFA biosynthetic pathway enzyme.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil. Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

Additionally, particular attention is given to several metal ions (e.g., $Mn^{+2}$, $Co^{+2}$, $Zn^{+2}$, $Mg^{+2}$) that promote synthesis of lipids and PUFAs in the fermentation media (Nakahara, T. et al. *Ind. Appl. Single Cell Oils*, D. J. Kyle and R. Colin, eds. pp 61-97 (1992)).

Purification of PUFAs

The PUFAs produced in a host microorganism as described herein may be found as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of fatty acids (including PUFAs) may include extraction with organic solvents, sonication, supercritical fluid extraction (e.g., using carbon dioxide), saponification and physical means such as presses, or combinations thereof. One is referred to the teachings of WO 2004/101757.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (hereinafter "Maniatis"); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

General molecular cloning was performed according to standard methods (Sambrook et al., supra). Oligonucleotides were synthesized by Sigma-Genosys (Spring, Tex.). Site-directed mutagenesis was performed using Stratagene's QuikChange™ Site-Directed Mutagenesis kit (San Diego, Calif.), per the manufacturer's instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains ATCC #20362 and ATCC #76982 were purchased from the American Type Culture Collection (Rockville, Md.). Strains were usually grown at 28° C. on YPD agar (1% yeast extract, 2% bactopeptone, 2% glucose, 2% agar) or in YPD liquid medium (2% bacto-yeast extract, 3% bactopeptone, 2% glucose).

Transformation of *Y. lipolytica* was performed according to the method of Chen, D. C. et al. (*Appl. Microbiol Biotechnol.* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1 and 20 g/L agar. Supplements of uracil were added as appropriate to a final concentration of 0.01% (thereby producing "MMU" selection media).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

"SD" media comprises: 0.67% yeast nitrogen base with ammonium sulfate, without amino acids and 2% glucose. And finally, to promote conditions of oleaginy, High Glucose Media ("HGM") was prepared as follows: 14 g/L $KH_2PO_4$, 4 g/L $K_2HPO_4$, 2 g/L $MgSO_4.7H_2O$, 80 g/L glucose (pH 6.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276 (1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Isolation of the *Yarrowia lipolytica* Gene Encoding GPAT

The present Example describes work performed to determine the nucleotide sequence (SEQ ID NO:3) of the *Yarrowia lipolytica* gene encoding GPAT (SEQ ID NO:4). This was possible by identifying an ORF in the Genolevures database of *Y. lipolytica* ORFs (sponsored by the Center for Bioinformatics, LaBRI, bâtiment A30, Universite Bordeaux 1, 351, cours de la Libération, 33405 Talence Cedex, France) and then designing degenerate primers to amplify the putative gene.

Identification of a Putative *Yarrowia lipolytica* GPAT

Based on the gene sequences encoding two isozymes of GPAT in *Saccharomyces cerevisiae* (GAT1 [GenBank Accession No. AJ311354; SEQ ID NO:2] and GAT2(SCT1) [GenBank Accession No. AJ314608; SEQ ID NO:1]; see also Zheng and Zou. *J. Biol. Chem.* 276(45):41710-41716 (2001) and WO 02/08391 A2), BLAST (Basic Local Alignment Search Tool; Altschul, S. F., et al., *J. Mol. Biol.* 215:403-410 (1993)) searches were conducted against the Genolevures genome database of *Y. lipolytica* ORFs (supra) to identify any similar sequences contained therein. The results of the BLAST comparisons identified one homolog (*Yarrowia lipolytica* ORF YAL1-CDS1055.1, a protein of 727 amino acids; SEQ ID NO:4; also GenBank Accession No. CAG81570) annotated as a protein having similarity to *S. cerevisiae* GPATs.

Following the tentative identification of ORF YAL1-CDS1055.1, this amino acid sequence (SEQ ID NO:4) was BLASTed against the *S. cerevisiae* isozymes encoding GPAT. The results of these BLAST comparisons are shown below and are reported according to the % identity, % similarity, and Expectation value.

TABLE 3

Comparison Of *Yarrowia lipolytica* ORF YAL1-CDS1055.1 To *Saccharomyces cerevisiae* GAT1 And GAT2(SCT1)

| Similarity Identified | % Identity[a] | % Similarity[b] | E-value[c] |
|---|---|---|---|
| GAT1 [GenBank Accession No. AJ311354; SEQ ID NO: 2] | 35 | 54 | 1.2e-113 |
| GAT2(SCT1) [GenBank Accession No. AJ314608; SEQ ID NO: 1] | 43 | 59 | 3.4e-141 |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Thus, it was hypothesized that ORF YALI-CDS1055.1 encoded a *Y. lipolytica* GPAT.

Amplification and Sequencing of the Putative *Yarrowia lipolytica* GPAT

Degenerate oligonucleotides, as shown below, were designed to amplify the entire coding region of ORF YALI-CDS1055.1.

```
Degenerate oligonucleotide YGPAT-F    (SEQ ID NO:5)
ATGTCNGAGACYGACCAYCTNCTN Degenerate oligonucleotide YGPAT-R    (SEQ ID NO:6)
YTCYTCRTCYTGYTCTCGYCGYTT
[Note:
The nucleic acid degeneracy code used for SEQ ID
NOs: 5 and 6 was as follows: R = A/G; Y = C/T; and
N = A/C/T/G.]
```

The PCR amplification was carried out in a 50 µl total volume using a 1:1 dilution of a premixed 2× PCR solution (TaKaRa Bio Inc., Otsu, Shiga, 520-2193, Japan). The final composition contained 25 mM TAPS, pH 9.3, 50 mM KCl, 2 mM $MgCl_2$, 1 mM 2-mercaptoethanol, 200 µM each deoxyribonucleotide triphosphate, 10 pmole of each primer, 50 ng genomic DNA of *Y. lipolytica* (ATCC #20362) and 1.25 units of TaKaRa Ex Taq™ DNA polymerase (Takara Mirus Bio, Madison, Wis.). The thermocycler conditions were set for 30 cycles at 94° C. for 2.5 min, 55° C. for 30 sec and 72° C. for 2.5 min, followed by a final extension at 72° C. for 6 min.

The PCR products were separated by gel electrophoresis in 1% (w/v) agarose. A 2.2 kB DNA fragment was excised and purified using a QiaexII gel purification kit (Qiagen, Valencia, Calif.). Subsequently, the purified 2.2 kB DNA fragment was cloned into the pGEM-T-easy vector (Promega, Madison, Wis.). The ligated DNA was used to transform cells of *E. coli* Top10 and transformants were selected on LB (1% bacto-tryptone, 0.5% bacto-yeast extract and 1% NaCl) agar containing ampicillin (100 μg/mL). Analysis of the plasmid DNA from one transformant confirmed the presence of a plasmid of the expected size, designated as "pGPAT-1".

Sequence analyses of pGPAT-1 showed that it contained a 2184 bp fragment of *Y. lipolytica* DNA encoding GPAT (SEQ ID NO:3). Specifically, identity of this gene sequence was determined by conducting BLAST searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266-272 (1993)) provided by the NCBI. The BLAST searches revealed that the translated product of SEQ ID NO:3 (comprising the putative gpat gene) had the highest BLAST hits to annotated GPATs from: (1) *Saccharomyces cerevisiae* (SwissPro P36148, Entrez CAA82146): 43% identity, 59% similarity, E-146; and (2) *Schizosaccharomyces pombe* SCT1 (GAT2) homolog (GPAT): 48% identity, 66% similarity, E-148.

Furthermore, the translated product of SEQ ID NO:3 was 100% identical to the amino acid sequence of ORF YAL1-CDS1055.1 (SEQ ID NO:4; also GenBank Accession No. CAG81570).

Example 2

Isolation of the 5' Upstream Region of GPAT from *Yarrowia lipolytica*

To isolate the GPAT promoter region upstream of the gene identified in Example 1, a genome-walking technique (Universal GenomeWalker, ClonTech, Calif.) was utilized, following the manufacturer's protocol.

Briefly, genomic DNA of *Y. lipolytica* was digested with DraI, EcoRV, PvuII or StuI individually, and the digested DNA samples were ligated with Genome Walker adaptor (SEQ ID NOs:7 [top strand] and 8 [bottom strand]), as shown below:
5'-GTAATACGACTCACTAT-
AGGGCACGCGTGGTCGACGGCCCGGGCTGGT-3'
3'-H2N-CCCGACCA-5'

PCR reactions were then carried out using the ligation products as templates and Adaptor-1 and YGPAT-5R-1 (SEQ ID NOs:9 and 10) as primers. The PCR amplification was carried out in a 50 μl total volume using the components and conditions described in Example 1, with the exception that the template used was 1 μl of ligation product (versus 50 ng genomic DNA). Second PCR reactions were then carried out using 1 μl of 1:50 diluted first PCR product as template, and Nested Adaptor Primer 2 and YGPAT-5R-2 (SEQ ID NOs:11 and 12) as primers. The PCR amplifications were carried out as described above.

A 1.7 kB DNA fragment, amplified from the EcoRV digested sample, was purified using a Qiagen PCR purification kit and cloned into the pGEM-T-easy vector (Promega, Madison, Wis.). The ligated DNA was used to transform *E. coli* Top10 and transformants were selected on LB agar containing ampicillin (100 μg/mL).

Analysis of the plasmid DNA from one transformant confirmed the presence of the expected plasmid, designated "pEcoRV-G-5". Sequence analyses showed that pEcoRV-G-5 contained a fragment of 1781 bp (SEQ ID NO:13), which included 1678 bp of 5' upstream sequence from the nucleotide 'A' (designated as +1) of the translation initiation codon 'ATG' of the GPAT gene. Assembly of DNA corresponding to overlapping SEQ ID NOs:3 and 13 yielded a single contig of DNA represented as SEQ ID NO:14 (FIG. 1; 3862 bp total length). This contig therefore contained the −1678 to +2181 region of the GPAT gene, wherein the 'A' position of the 'ATG' translation initiation codon was designated as +1.

Example 3

Synthesis of PY5-30 and pDMW214

Two plasmids were created, each comprising a different chimeric gene consisting of either the native *Y. lipolytica* TEF or FBAIN promoter and the "GUS" reporter gene, wherein "GUS" corresponds to the *E. coli* gene encoding β-glucuronidase (Jefferson, R. A. *Nature*. 342(6251):837-838 (1989)). This was required for comparative studies investigating the promoter activity of TEF, FBAIN and GPAT, as described in Example 7.

Synthesis of Plasmid PY5-30 (TEF::GUS::XPR)

The synthesis of plasmid pY5-30, comprising a TEF:: GUS::XPR chimeric gene, is described in WO2005/003310. More specifically, plasmid pY5-30 (FIG. 2A; SEQ ID NO:15) contained: a *Yarrowia* autonomous replication sequence (ARS18); a ColE1 plasmid origin of replication; an ampicillin-resistance gene (Amp$^R$) for selection in *E. coli*; a *Yarrowia* LEU2 gene for selection in *Yarrowia*; and the chimeric TEF::GUS::XPR gene.

Synthesis of Plasmid DDMW214 (FBAIN::GUS::XPR)

The synthesis of plasmid pDMW214, comprising a FBAIN::GUS::XPR chimeric gene, is described in WO 2005/049805. Briefly, however, the FBAIN promoter region (SEQ ID NO:16; which includes both an upstream DNA sequence and a downstream sequence from the putative 'ATG' translation initiation codon of the fructose-bisphosphate aldolase (fba1) gene [wherein the downstream region comprises an intron]) was amplified by PCR, digested with NcoI and SalI, and then purified following gel electrophoresis. The NcoI/SalII-digested PCR products were ligated to NcoI/SalI digested pY5-30 vector to produce plasmid "pDMW214" (FIG. 2B).

Example 4

Synthesis of pYGPAT-GUS

The present Example describes the synthesis of pYGPAT-GUS (comprising a GPAT::GUS::XPR chimeric gene). Synthesis of this plasmid first required amplification of the putative GPAT promoter region. Then, the putative promoter region was cloned into a derivative of pY5-30 (Example 3).

Identification and Amplification of the GPAT Putative Promoter Region

The region upstream of the gpat gene's 'ATG' start site was considered to represent the putative GPAT promoter region. This corresponded to the nucleotide region between the −1130 position and the 'ATG' translation initiation site of the gpat gene (wherein the 'A' nucleotide of the 'ATG' translation initiation codon was designated as +1). This promoter region is provided as SEQ ID NO:17 and was designated herein as "GPAT-Pro".

GPAT-Pro was amplified by PCR using primers GPAT-5-1 and GPAT-5-2 (SEQ ID NOs:18 and 19), and pEcoRV-G-5 (Example 2) as template. The PCR amplification was carried out as described in Example 1. The PCR product was then purified using a Qiagen PCR purification kit and was completely digested with SalI and NcoI. The digestion product was again purified with a Qiagen PCR purification kit and ligated to NcoI/SalI digested pY5-30 vector (Example 3, wherein the NcoI/SalI digestion had excised the TEF promoter from the pY5-30 vector backbone). Ligated DNA was then used to individually transform *E. coli* Top10. Transformants were selected on LB agar containing ampicillin (100 µg/mL).

Analysis of the plasmid DNA from one transformant containing GPAT-Pro confirmed the presence of the expected plasmid, designated "pYGPAT-GUS". Thus, this plasmid contained a chimeric gene comprising a GPAT promoter, GUS reporter gene and the 3' region of the XPR gene (FIG. 2C).

Example 5

Generation of *Yarrowia lipolytica* ATCC #20362 Derivative PDMW236-#18

The present Example describes the construction of *Y. lipolytica* ATCC #20362 derivative pDMW236-#18. Although originally intended to enable high production of EPA relative to the total lipids, this strain possessed a "dead Δ17 desaturase chimeric gene" that inhibited this conversion. However, the strain was useful for the purposes described herein, as a result of the engineered Leu-marker. Comparison of the TEF, GPAT and FBAIN promoters was examined in this strain based on analysis of GUS expression, as described in Example 7 (infra).

The development of *Y. lipolytica* ATCC #20362 derivative pDMW236-#18 required the construction of strain M4 (producing 8% DGLA), followed by transformation with plasmid pDMW236 (FIG. 3A).

Construction of Strain M4 Producing 8% DGLA

Construct pKUNF12T6E (FIG. 3B; SEQ ID NO:20) was generated to integrate four chimeric genes (comprising a Δ12 desaturase, a Δ6 desaturase and 2 elongases) into the Ura3 loci of wild type *Yarrowia* strain ATCC #20362, to thereby enable production of DGLA. The pKUNF12T6E plasmid contained the following components:

TABLE 4

Description of Plasmid pKUNF12T6E (SEQ ID NO: 20)

| RE Sites And Nucleotides Within SEQ ID NO: 20 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S:Pex20, comprising: FBAIN: *Yarrowia* FBAIN promoter (SEQ ID NO: 16) EL1S: codon-optimized elongase 1 gene (SEQ ID NO: 21), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 23), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: *Yarrowia* FBA promoter (SEQ ID NO: 25) F.Δ12: *Fusarium moniliforme* Δ12 desaturase gene (SEQ ID NO: 26) Lip2: Lip2 terminator sequence from *Yarrowia* Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 28), derived from *Thraustochytrium aureum* (U.S. 6,677,145) XPR: 100 bp of the 3' region of the *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura-strains. Single colonies of Ura-strains were then inoculated into liquid MMU at 30° C. and shaken at 250 rpm/min for 2 days. The cells were collected by centrifugation, lipids were extracted, and fatty acid methyl esters were prepared by trans-esterification and subsequently analyzed with a Hewlett-Packard 6890 GC.

GC analyses showed the presence of DGLA in the transformants containing the 4 chimeric genes of pKUNF12T6E (FIG. 3B), but not in the wild type *Yarrowia* control strain. Most of the selected 32 Ura⁻ strains produced about 6% DGLA of total lipids. There were 2 strains (i.e., strains M4 and 13-8) that produced about 8% DGLA of total lipids.

Transforamtion with Plasmid pDMW236

Construct pDMW236 (SEQ ID NO:30) is shown in FIG. 3C. In a manner similar to that described above, the vector was synthesized, transformed into strain M4 (supra) according to the General Methods and individual colonies were selected and grown. The cells were collected by centrifugation, lipids were extracted, and fatty acid methyl esters were prepared by trans-esterification and subsequently analyzed with a Hewlett-Packard 6890 GC. GC analyses showed no EPA in the total lipids. One clone was designated as *Y. lipolytica* ATCC #20362 derivative pDMW236-#18.

Example 6

Transformation of *Y. lipolytica* with PY5-30, pYGPAT-GUS, and pDMW214

The plasmids pY5-30 (Example 3; comprising a TEF::GUS::XPR chimeric gene), pYGPAT-GUS (Example 4; comprising a GPAT::GUS::XPR chimeric gene) and pDMW214 (Example 3; comprising a FBAIN::GUS::XPR chimeric gene) were transformed separately into *Y. lipolytica* ATCC #20362 derivative pDMW236418, according to the General Methods. Selection was performed on minimal media plates lacking leucine and maintained at 30° C. for 2 to 3 days.

Using this technique, transformants were obtained that contained pY5-30, pYGPAT-GUS and pDMW214, respectively.

Example 7

Comparative Analysis of the TEF, GPAT and FBAIN Promoter Activities in *Yarrowia lipolytica*, as Determined by Histochemical Assay The activity of the TEF, GPAT and FBAIN promoters was determined in *Y. lipolytica* containing the pY5-30, pYGPAT-GUS and pDMW214 constructs, each of which possessed a GUS reporter gene and the 3' region of the *Yarrowia* Xpr gene (from Example 6). GUS activity in each expressed construct was measured by histochemical assays (Jefferson, R. A. *Plant Mol. Biol. Reporter* 5:387-405 (1987)).

Specifically, *Y. lipolytica* strains containing plasmids pY5-30, pYGPAT-GUS and pDMW214, respectively, were grown from single colonies in 3 mL MM with 0.1 g/L L-adenine and 0.1 g/L L-lysine at 30° C. to an $OD_{600}$~1.0. Then, 100 µl of cells were collected by centrifugation, resuspended in 100 µl of histochemical staining buffer and incubated at 30° C. [Staining buffer prepared by dissolving 5 mg of 5-bromo4-chloro-3-indolyl glucuronide (X-Gluc) in 50 µl dimethyl formamide, followed by addition of 5 mL 50 mM $NaPO_4$, pH 7.0.]

The results of histochemical staining showed that the GPAT promoter in construct pYGPAT-GUS was active. Comparatively, the GPAT promoter appeared to be much stronger than the TEF promoter (FIG. 4) and have diminished activity with respect to the FBAIN promoter.

Example 8

Comparative Analysis of the TEF, FBAIN And GPAT Promoter Activities in *Yarrowia lipolytica*, as Determined by Fluorometric Assay A variety of methods are available to compare the activity of various promoters, to thereby facilitate determination of each promoter's strength for use in future applications wherein a suite of promoters would be necessary to construct chimeric genes. Thus, although it may be useful to indirectly quantitate promoter activity based on reporter gene expression using histochemical staining (Example 7), quantification of GUS expression using more quantitative means may be desirable. One suitable method to assay GUS activity is by fluorometric determination of the production of 4-methylumbelliferone (4-MU) from the corresponding substrate, β-glucuronide (4-MUG; see Jefferson, R. A., *Plant Mol. Biol. Reporter* 5:387-405 (1987)).

*Y. lipolytica* strain Y2034 containing plasmids pY5-30, pYGPAT-GUS and pDMW214, respectively (from Example 6), were grown from single colonies in 10 mL SD medium at 30° C. for 48 hrs to an $OD_{600}$~5.0. Two mL of each culture was collected for GUS activity assays, as described below, while 5 mL of each culture was switched into HGM.

Specifically, cells from the 5 mL aliquot were collected by centrifugation, washed once with 5 mL of HGM and resuspended in HGM. The cultures in HGM were then grown in a shaking incubator at 30° C. for 24 hrs. Two mL of each HGM culture were collected for GUS activity assay, while the remaining culture was allowed to grow for an additional 96 hrs before collecting an additional 2 mL of each culture for the assay.

Each 2 mL culture sample in SD medium was resuspended in 1 mL of 0.5× cell culture lysis reagent (Promega). Resuspended cells were mixed with 0.6 mL of glass beads (0.5 mm diameter) in a 2.0 mL screw cap tube with a rubber O-ring. The cells were then homogenized in a Biospec mini beadbeater (Bartlesville, Okla.) at the highest setting for 90 sec. The homogenization mixtures were centrifuged for 2 min at 14,000 rpm in an Eppendof centrifuge to remove cell debris and beads. The supernatant was used for GUS assay and protein determination.

For each fluorometric assay, 200 µl of extract was added to 800 µl of GUS assay buffer (2 mM 4-methylumbelliferyl-β-D-glucuronide ("MUG") in extraction buffer) and placed at 37° C. Aliquots of 100 µl were taken at 0, 30 and 60 min time points and added to 900 µl of stop buffer (1 M $Na_2CO_3$). Each time point was read using a Fluorimeter (CytoFluorR Series 4000, Framingham, Mass.) set to an excitation wavelength of 360 nm and an emission wavelength of 455 nm. Total protein concentration of each sample was determined using 20 µl of extract and 980 µl of BioRad Bradford reagent (Bradford, M. M. *Anal. Biochem.* 72:248-254 (1976)). GUS activity is expressed as nmoles of 4-MU per minute per mg of total protein.

As shown in the Table below, the activity of the GPAT promoter was significantly higher than the TEF promoter but lower than the FBAIN promoter under all the conditions tested.

TABLE 5

Comparison of TEF, FBAIN, And GPAT Promoter Activity Under Various Growth Conditions

| Culture Conditions | Promoter | | |
|---|---|---|---|
| | TEF | FBAIN | GPAT |
| 48 hr, SD | 0.401 | 43.333 | 5.252 |
| 24 hr, HGM | 0.942 | 30.694 | 2.969 |
| 120 hr HGM | 0.466 | 17.200 | 3.050 |

Example 9

Use of the GPAT Promoter for Δ6 Desaturase Expression in *Yarrowia lipolytica*

The present Example describes the construction of a chimeric gene comprising a GPAT promoter, fungal Δ6 desaturase and the Pex20 terminator, and the expression of this chimeric gene in *Y. lipolytica*. Since transformed host cells were able to produce γ-linoleic acid (while wildtype *Y. lipolytica* do not possess any Δ6 desaturase activity), this confirmed the ability of the GPAT promoter to drive expression of heterologous PUFA biosynthetic pathway enzymes in oleaginous yeast such as *Y. lipolytica*.

Construction of Plasmid pZGP6B, Comprising A GPAT::Δ6B1::Pex20 Chimeric Gene

Synthesis of *M. alpina* cDNA

*M. alpina* cDNA was synthesized using the BD-Clontech Creator Smart® cDNA library kit (Mississauga, ON, Canada), according to the manufacturer's protocol.

Specifically, *M. alpina* was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform/isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol (made with RNase-free water) and air-dried. The total RNA sample was then redissolved in 500 μl of water, and the amount of RNA was measured by A260 nm using 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 μl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE were loaded and the columns centrifuged for 2 min at 4500×g. The washing step was repeated once, except that the centrifugation time was extended to 5 min. Total RNA was eluted by applying 250 μl of RNase free water to each column, waiting for 1 min and centrifuging at 4500×g for 3 min.

PolyA(+)RNA was then isolated from the above total RNA sample, following the protocol of Amersham Biosciences' mRNA Purification Kit. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly(A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/μl.

cDNA was generated, using the LD-PCR method specified by BD-Clontech and 0.1 μg of polyA(+) RNA sample. Specifically, for $1^{st}$ strand cDNA synthesis, 3 μl of the poly(A)+RNA sample was mixed with 1 μl of SMART IV oligo nucleotide (SEQ ID NO:31) and 1 μl of CDSIII/3' PCR primer (SEQ ID NO:32). The mixture was heated at 72° C. for 2 min and cooled on ice for 2 min. To the tube was added the following: 2 μl first strand buffer, 1 μl 20 mM DTT, 1 μl 10 mM dNTP mix and 1 μl Powerscript reverse transcriptase. The mixture was incubated at 42° C. for 1 hr and cooled on ice.

The $1^{st}$ strand cDNA synthesis mixture was used as template for the PCR reaction. The reaction mixture contained the following: 2 μl of the $1^{st}$ strand cDNA mixture, 2 μl 5'-PCR primer (SEQ ID NO:33), 2 μl CDSIII/3'-PCR primer (SEQ ID NO:32), 80 μl water, 10 μl 10× Advantage 2 PCR buffer, 2 μl 50× dNTP mix and 2 μl 50× Advantage 2 polymerase mix. The thermocycler conditions were set for 95° C. for 20 sec, followed by 20 cycles of 95° C. for 5 sec and 68° C. for 6 min on a GenAmp 9600 instrument. PCR product was quantitated by agarose gel electrophoresis and ethidium bromide staining.

Cloning a *Morteriella alpina* Δ6 Desaturase

A *M. alpina* Δ6 desaturase gene (referred to herein as "Δ6B") was identified in GenBank (Accession No. AB070555). The Δ6B gene was PCR amplified using the oligonucleotides described below in Table 6 as primers and the cDNA pool of *M. alpina* as template.

TABLE 6

Primers Used For Amplification Of The *M. alpina* Δ6 Desaturase

| Primer | Length | Restriction Enzyme Site | Optimization* | SEQ ID NO |
|---|---|---|---|---|
| YL421 | 86 bp | NcoI around the translation initiation codon | 7 of 14 codons at the N-terminal end | 34 |
| YL422 | 81 bp | NotI immediately after the translation stop codon | 3 of 11 codons at the C-terminal end | 35 |

*Optimization was according to *Yarrowia* codon usage, as described in U.S. Patent Application No. 10/840478.

The PCR amplification were carried out in 50 μl total volume containing: 10 ng cDNA of *M. alpina*, PCR buffer containing 10 mM KCl, 10 mM $(NH_4)_2SO_4$, 20 mM Tris-HCl (pH 8.75), 2 mM $MgSO_4$, 0.1% Triton X-100, 100 μg/mL BSA (final concentration), 200 μM each deoxyribonucleotide triphosphate, 10 pmole of each primer (supra) and 1 μl of PfuTurbo DNA polymerase (Stratagene, San Diego, Calif.). The thermocycler conditions were set for 35 cycles at 95° C. for 1 min, 56° C. for 30 sec, and 72° C. for 1 min, followed by a final extension at 72° C. for 10 min.

The PCR products were purified using a Qiagen PCR purification kit (Valencia, Calif.), and then further purified following gel electrophoresis in 1% (w/v) agarose. Subsequently, the PCR products were cloned into the pGEM-T-easy vector (Promega, Madison, Wis.). The ligated DNA was used to transform cells of *E. coli* DH5α and transformants were selected on LB agar containing ampicillin (100 μg/mL). Analysis of the plasmid DNA from one transformant confirmed the presence of a plasmid of the expected size. The plasmid was desinated as "pT-6Bc".

Sequence analysis showed that pT-6Bc contained a Δ6 coding region sequence (SEQ ID NO:36) that was similar to GenBank Accession No. AB070555 (~90% identity at the DNA sequence level and 97% identity at the amino acid level). It was assumed that the differences in the DNA and amino acid sequence came from variations of the same gene in different strains of *M. alpina*. Additionally, the Δ6B desaturase within pT-6Bc contained the codon-optimized base pairs that were present at the N— and C-terminal end, according to the preferred codon usage in *Yarrowia*.

Using plasmid pT-6BC as template and oligonucleotides YL475 and YL476 (SEQ ID NOs:37 and 38) as primers, the internal NcoI site of Δ6B was eliminated by in vitro mutagenesis (Stratagene, San Diego, Calif.) to produce pT-6BC-N. Using pT-6BC-N as template and oligonucleotides YL477 and YL478 (SEQ ID NOs:39 and 40) as primers, the internal SphI site of Δ6B was eliminated by in vitro mutagenesis to produce pT-6BC-NS. Finally, using pT-6BC-NS as template and oligonucleotides YL479 and YL480 (SEQ ID NOs:41 and 42) as primers, the internal ClaI site of Δ6B was eliminated by in vitro mutagenesis to produce pT-6BC-NSC. The elimination of these three internal sites did not change the amino acid sequence of the Δ6B gene.

PCR Amplification of *Yarrowia* GPAT Promoter

Using plasmid pYGPAT-GUS (Example 4) as template and oligonucleotides YL497 (SEQ ID NO:43, containing a SwaI site) and YL498 (SEQ ID NO:44, containing a NcoI site) as primers, the GPAT promoter was amplified by PCR. Specifically, the PCR amplification was carried out in a 50 µl total volume using the components and conditions described above, with the exception that 10 ng plasmid DNA was used as template.

The PCR products were purified using a Qiagen PCR purification kit (Valencia, Calif.), digested with SwaI/NcoI, and then purified following gel electrophoresis in 1% (w/v) agarose.

PCR Amplification of the *Yarrowia* Pex20 Terminator

The *Yarrowia* PEX20 terminator (SEQ ID NO:45) of the gene encoding peroxin (GenBank Accession No. AF054613) was amplified from *Y. lipolytica* genomic DNA using YL259 (SEQ ID NO:46, containing a NotI site) and YL260 (SEQ ID NO:47, containing a BsiWI site) as primers. The 324 bp PCR product was digested with Not1 and BsiW1 and gel purified.

Construction of the pY25-d12d-PS Plasmid

Figure 5A:
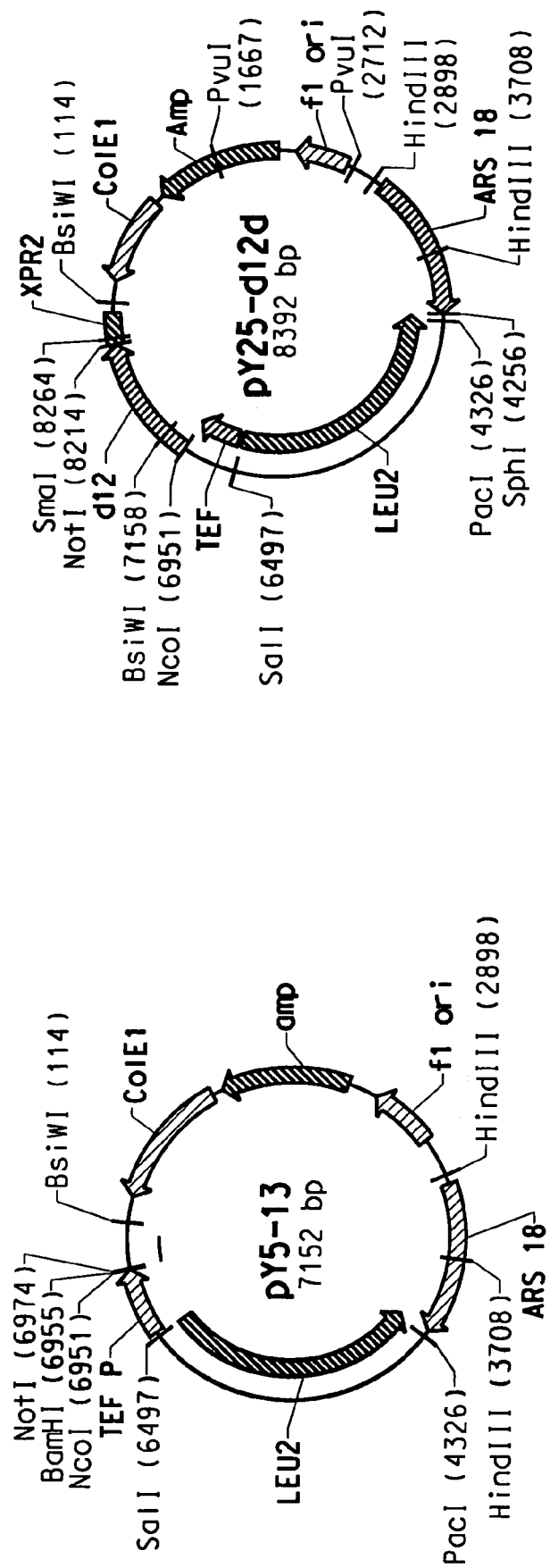

The synthesis of pY5-13 is described in WO2005/003310 and is illustrated in FIG. 5A.

Figure 5B:
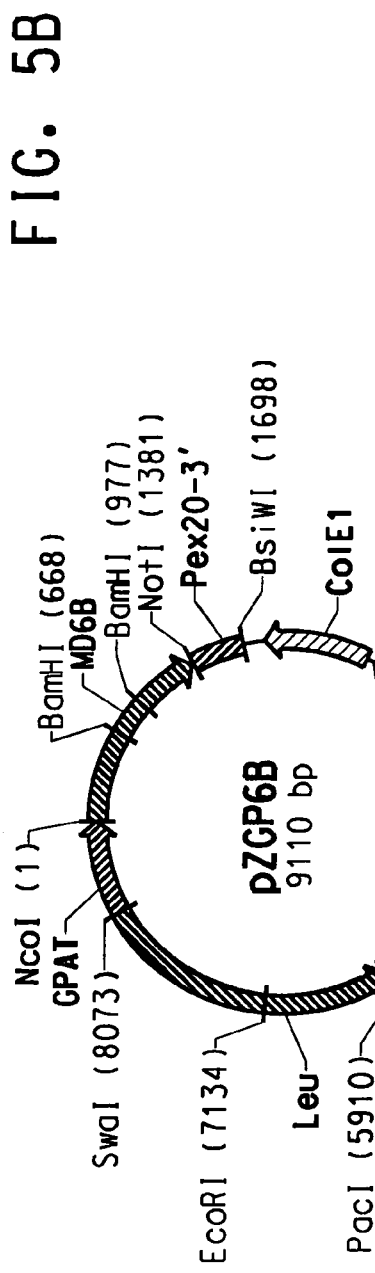
Figure 5C:

The ORF encoding the *Y. lipolytica* Δ12 desaturase (SEQ ID NOs:48 and 49) was PCR amplified using upper primer P147 (SEQ ID NO:50) and lower primer P148 (SEQ ID NO:51) from the genomic DNA of *Y. lipolytica* ATCC #76982 (WO2004/104167). The correct sized (1260 bp) fragment was isolated, purified, digested with Nco I and Not I and cloned into NcoI-Not I cut pY5-13 vector (supra), such that the gene was under the control of the TEF promoter. Correct transformants were confirmed by miniprep analysis and the resultant plasmid was designated "pY25-d12d" (FIG. 5B). Using oligonucleotides YL242 and YL243 (SEQ ID NOs:52 and 53) as primers and pY25-d12d as template, a PmeI site was introduced into pY25-d12d by site-directed mutagenesis to generate pY25-d12d-P. A SwaI site was introduced into pY25-d12d-P by in vitro mutagenesis using YL226 and YL227 (SEQ ID NOs:54 and 55) as primers to generate plasmid pY25-d12d-PS.

Construction of pZGP6B, Comprising a GPAT::Δ6B1::Pex20 Chimeric Gene

Plasmid pY25-d12d-PS was digested with SwaI/BsiMI, and the large fragment was used as vector. The SwaI/BsiWI digested large fragment of plasmid pY25-d12d-PS, the SwaI/NcoI digested GPAT promoter DNA fragment, NcoI/NotI digested Δ6B gene DNA fragment and the NotI/BsiMI digested Pex20 terminator were directionally ligated together. The ligated DNA was used to transform cells of *E. coli* DH5α and transformants were selected on LB agar containing ampicillin (100 µg/mL). Analysis of the plasmid DNA from one transformant confirmed the presence of a plasmid of the expected size. The plasmid was desinated "pZGP6B" and comprised a GPAT::Δ6B::Pex20 terminator chimeric gene (SEQ ID NO:56).

Expression of Plasmid pZGP6B (GPAT::Δ6B::Pex20) in *Yarrowia lipolytica*

Plasmid pZGP6B (FIG. 5C) was transformed into wild type (WT) *Y. lipolytica* ATCC #76892 according to the methodology described above in the General Methods. Transformant cells were plated onto MM plates lacking leucine and maintained at 30° C. for 2 to 3 days. Using this technique, transformants were obtained that contained pZGP6B.

Single colonies of wild type and transformant cells were each grown in 3 mL MM with 0.1 g L-adenine and 0.1 g L-lysine at 30° C. to an $OD_{600}$~1.0. The cells were harvested, washed in distilled water, speed vacuum dried and subjected to direct trans-esterification and GC analysis (according to the methodology of the General Methods).

The fatty acid profile of wildtype *Yarrowia* and the transformant containing pZGP6B are shown below in Table 7. Fatty acids are identified as 16:0 (palmitate), 16:1 (palmitoleic acid), 18:0, 18:1 (oleic acid), 18:2 (LA) and 18:3 (GLA) and the composition of each is presented as a % of the total fatty acids.

TABLE 7

Expression of GPAT::Δ6B::Pex20 In *Yarrowia lipolytica*

| *Y. lipolytica* strain | % 16:0 | % 16:1 | % 18:0 | % 18:1 | % 18:2 | % GLA |
|---|---|---|---|---|---|---|
| WT | 12 | 9 | 4 | 44 | 24 | 0 |
| WT + pZGP6B | 11 | 10 | 4 | 43 | 15 | 10 |

The results above demonstrated that the GPAT promoter is suitable to drive expression of the Δ6 desaturase, leading to production of GLA in *Yarrowia*.

What is claimed is:

1. An isolated nucleic acid molecule comprising a GPAT promoter selected from the group consisting of SEQ ID NOs:13 and 17.

* * * * *